(12) United States Patent
Pilkington et al.

(10) Patent No.: US 10,377,783 B2
(45) Date of Patent: Aug. 13, 2019

(54) METHODS AND COMPOUNDS FOR ENHANCING CONTRAST IN MAGNETIC RESONANCE IMAGING (MRI)

(71) Applicant: Brock University, St. Catharines (CA)

(72) Inventors: Melanie Pilkington, St. Catharines (CA); Emma Louise Stares, Escondido, CA (US)

(73) Assignee: Brock University, St. Catherines (CA)

( * ) Notice: Subject to any disclaimer, the term of this patent is extended or adjusted under 35 U.S.C. 154(b) by 17 days.

(21) Appl. No.: 15/179,139

(22) Filed: Jun. 10, 2016

(65) Prior Publication Data

US 2016/0362434 A1      Dec. 15, 2016

Related U.S. Application Data

(60) Provisional application No. 62/174,752, filed on Jun. 12, 2015.

(51) Int. Cl.

| | |
|---|---|
| *A61K 49/00* | (2006.01) |
| *A61K 49/10* | (2006.01) |
| *C07F 13/00* | (2006.01) |
| *A61K 49/08* | (2006.01) |

(52) U.S. Cl.
CPC ........ *C07F 13/005* (2013.01); *A61K 49/0021* (2013.01); *A61K 49/0052* (2013.01); *A61K 49/085* (2013.01); *A61K 49/106* (2013.01)

(58) Field of Classification Search
CPC .................................................. A61K 49/00
See application file for complete search history.

(56) References Cited

U.S. PATENT DOCUMENTS

2011/0118459 A1    5/2011   Smith et al.

OTHER PUBLICATIONS

Melanie Pilkington et al. Rational Design of a Covalently Tethered Dinuclear [MnII(N3O2)Cl(OH2]2 Macrocyclic Building Block: Synthesis, strudture, and Magnetic Properties, (Inorg. Chem. 46, 4763-4765). (Year: 2007).*
F. Bonadio, M.-C. Senna, J. Ensling, A. Sieber, A. Neels, H. Stoeckli-Evans, S. Decurtins, "Cyano-Bridged Structures Based on [MnII(N3O2-Macrocycle)]2+: A Synthetic, Structural, and Magnetic Study" Inorg. Chem. 2005, 44, 969-978.
D. Zhang, H. Wang, Y. Chen, Z.-H. Ni, L. Tian, J. Jiang, "Rational Design and Assembly of a New Series of Cyanide-Bridged FeIII—MnII One-Dimensional Single Chain Complexes: Synthesis, Crystal Structures, and Magnetic Properties" Inorg. Chem. 2009, 48, 5488-5496.
G. Rombaut, S. Golhen, L. Ouahab, C. Mathonière, O. Kahn, "Structural and photomagnetic studies of a 1-D bimetallic chain [MnII2(L)2(H2O)][MoIV(CN)8].5H2O (L = macrocycle): analogy with the photo-oxidation of K4[MoIV(CN) 8].2H2O" J. Chem. Soc. Dalton Trans. 2000, 3609-3614.
K. Qian, X.-C. Huang, C. Zhou, X.-Z. You, X.-Y. Wang, K. R. Dunbar, "A Single-Molecule Magnet Based on Heptacyanomolybdate with the Highest Energy Barrier for a Cyanide Compound" J. Am. Chem. Soc. 2013, 135, 13302-13305.
A. K. Sra, M. Andruh, O. Kahn, S. Golhen, L. Ouahab, J. V. Yakhmi, "A Mixed-Valence and Mixed-Spin Molecular Magnetic Material: [MnIIL]6[MoIII(CN)7][MoIV(CN)8]2.19.5H2O" Angew. Chem., Int. Ed. 1999, 38, 2606-2609.
X. Y. Wang, A. V. Prosvirin, K. R. Dunbar, "A Docosanuclear {Mo8Mn14} Cluster Based on [Mo(CN)7]4-" Angew. Chem. Int. Ed. 2010, 49, 5081-5084.
M. Rohrer, H. Bauer, J. Mintorovitch, M. Requardt, H.-J. Weinmann, "Comparison of Magnetic Properties of MRI Contrast Media Solutions at Different Magnetic Field Strengths" Invest. Radiol. 2005, 40, 715-724.
S. Aime, P. Caravan, "Biodistribution of Gadolinium-Based Contrast Agents, Including Gadolinium Deposition" J. Magn. Reson. Imaging 2009, 30(6), 1259-1267.
M. Numata, K. Koumoto, M. Mizu, K. Sakurai, S. Shinkai, "Parallel vs. anti-parallel orientation in a curdlan/oligo(dA) complex as estimated by a FRET technique" Org. Biomol. Chem. 2005, 3, 2255-2261.

(Continued)

*Primary Examiner* — Michael G Hartley
*Assistant Examiner* — Jagadishwar R Samala
(74) *Attorney, Agent, or Firm* — Bereskin & Parr LLP/S.E.N.C.R.L., s.r.l.; Patricia Folkins; Andrea Berenbaum

(57) ABSTRACT

The present application relates to methods and compounds for enhancing contrast in magnetic resonance imaging. The methods comprise administering compounds of Formula I(a) or I(b) to a subject and obtaining a magnetic resonance image of the subject. The present application also relates to methods of preparing compounds of the Formula I(a) as well as intermediate compounds used in such a method of preparation.

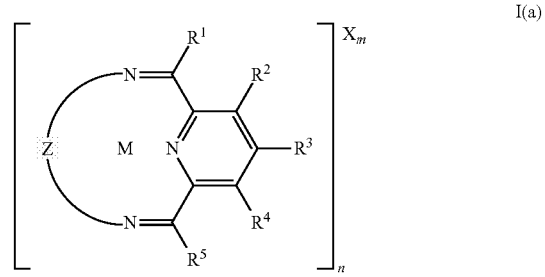

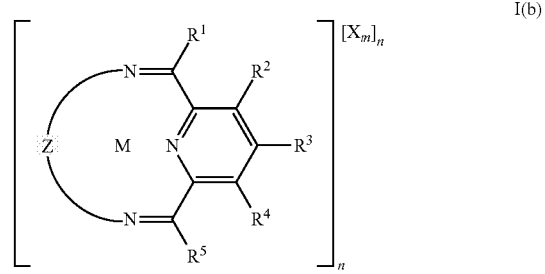

20 Claims, 14 Drawing Sheets

(56) References Cited

OTHER PUBLICATIONS

K. M. Bonger, R. J. B. H. N. van den Berg, L. H. Heitman, A. P. Ijzerman, J. Oosterom, C. M. Timmers, H. S. Overkleeft, G. A. van der Marel, "Synthesis and evaluation of homo-bivalent GnRHR ligands" Bioord. Med. Chem. 2007, 15, 4841-4856.
K. E. Pryor, G. W. Shipps Jr, D. A. Skyler, J. Rebek Jr, "The Activated Core Approach to Combinatorial Chemistry: A Selection of New Core Molecules" Tetrahedron 1998, 54, 4107-4124.
J. Wang, B. Slater, A. Alberola, H. Stoeckli-Evans, F. S. Razavi, M. Pilkington, "Rational Design of a Covalently Tethered Dinuclear [MnII(N3O2)C1(OH2)]22+Macrocyclic Building Block: Synthesis, Structure, and Magnetic Properties" Inorg. Chem. 2007, 46, 4763-4765.
Q. Wang, S. Vanneri, N. Zarrabi, H. Wang, C. Desplanches, J.-F. Letard, T. Seda, M. Pilkington, "Stereochemistry for engineering spin crossover: structures and magnetic properties of a homochiral vs. racemic [Fe(N3O2)(CN)2]complex" Dalton Trans. 2015, 44, 6711-6714.
M. G. B. Drew, A. H. B. Othman, S. G. McFall, P. D. A. McIlroy, S. M. Nelson, "Seven-coordination in metal complexes of quinquedentate macrocyclic ligands. Part 7. Synthesis and properties of metal complexes of an N3O2 macrocycle and crystal structure of {2,13-dimethyl-6,9-dioxa-3,12,18-triazabicyclo[12.3.1]octadeca-1(18),2,12,14,16-pentaene} diisothiocyanatomanganese(II)" J. Chem. Soc., Dalton Trans. 1977, 1173-1180.
D. Zhang, H. Wang, L. Tian, J. Jiang, Z.-H. Ni, "Rational design of cyanide-bridged heterometallic M(I)-Mn(II) (M = Ag, Au) one-dimensional chain complexes: synthesis, crystal structures and magnetic properties" CrystEngComm 2009, 11, 2447-2451.
H. C. Kolb, M. G. Finn, K. B. Sharpless, "Click Chemistry: Diverse Chemical Function from a Few Good Reactions" Angew. Chem. Int. Ed. 2001, 40, 2004-2021.
J. E. Hein, V.V. Fokin, "Copper-catalyzed azide-alkyne cycloaddition (CuAAC) and beyond: new reactivity of copper(I) acetylides" Chem. Soc. Rev. 2010, 39, 1302-1315.
C. Bernhard, C. Goze, Y. Rousselin, F. Denat, "First bodipy-DOTA derivatives as probes for bimodal imaging" Chem. Commun. 2010, 46, 8267-8269.
N. Candelon, N. Hadade, M. Matache, J.-L. Canet, F. Cisnetti, D. P. Funeriu, L. Nauton, A. Gautier, "Luminogenic ""clickable lanthanide complexes for protein labeling" Chem. Commun. 2013, 49(80), 9206-9208.
Z. E. A. Chamas, X. Guo, J.-L. Canet, A. Gautier, D. Boyer, R. Mahiou. "Clicked dipicolinic antennae for lanthanide uminescent probes" Dalton Trans. 2010, 39, 7091-7.
B. Huang, M. A. Prantil, T. L. Gustafson, J. R. Parquette, "The Effect of Global Compaction on the Local Secondary Structure of Folded Dendrimers" J. Am. Chem. Soc. 2003, 125(47), 14518-14530.
M. G. B. Drew, A. H. bin Othman, S. G. McFall, P. D. A. McIlroy, S. M. Nelson. "Seven-coordination in metal complexes of quinquedentate macrocyclic ligands. 5. Properties of pentagonal-bipyramidaland- pyramidal-manganese(II) complexes and crystal structure of {2,15-dimethyl-3,7,10,14,20-pentaazabicyclo-[14.3.1]eicosa-1(20),2,14,16,18-pentaenebis(isothiocyanato)manganese(II)" Dalton Trans. 1977, 438-46.
R. Bastida, A. de Blas, P. Castro, D. E, Fenton, A. Macias, R. Rial, A. Rodriquez, T. Rodriquez-Blas. "Complexes of anthanide(III) ions with macrocyclic ligands containing pyridine head units" Journal of the Chemical Society, Dalton Transactions: Inorganic Chemistry (1996), (8), 1493-7.
D. H. Cook, D. E. Fenton, M. G. B. Drew, A. Rodgers, M. McCann, S. M. Nelson. "Mononuclear and Homobinuclear Lead(II) Complexes of Macrocyclic Schiff Bases" Inorg. Chem., 1979, 414-419.
A. M. Arif, C. J. Gray, F. A. Hart, M. B. Hursthouse. "Synthesis and Structure of Lanthanide Complexes of a Mixed Donor Macrocyclic Ligand" Inorg. Chim. Acta 1985, 109, 179-183.

D. E. Fenton, R. Leonaldi. "Some penta— and hexadentate Macrocyclic Schiff Base Complexes of the Toxic Metals" Inorg. Chim. Acta 1981, 55, L51-L53.
O. Jimenez-Sandoval, D. Ramirez-Rosales, M. d J. Rosales-Hoz, M. E. Sosa-Torres, R. Zamorano-Ulloa, "Magnetostructural behavior of the complex [MnL(H2O)] CI2-4H2O at variable temperature studied by electron spin resonance (L = 2,13-dimethyl1-3,6,9,12,18-pentaazabicyclo[12.3.1]octadeca-1(18),2,12,14,16-pentaene)" Journal of the Chemical Society, Dalton Transactions: Inorganic Chemistry 1998, 10, 1551-1556.
E. B. Fleischer, S. W. Hawkinson, "The structure of two seven-coordinate complexes of iron(III)" Journal of the American Chemical Society 1967, 89(3), 720-1.
S. M. Nelson, D. H. Busch, "Seven-coordination in some mononuclear and binuclear iron(III) complexes containing a pentadentate macrocyclic ring" Inorganic Chemistry 1969, 8(9), 1859-63.
M. G. B. Drew, A. H. Bin Othman, P. D. A. McIlroy, S. M. Nelson, "Seven-coordination in metal complexes of quinquedentate macrocyclic ligands. II. Synthesis, properties, and crystal and molecular structure of iron(III) derivatives of two N5 macrocycles" Journal of the Chemical Society, Dalton Transactions: Inorganic Chemistry (1972-1999) 1975, 23, 2507-16.
M. G. B. Drew, A. H. B. Othman, S. G. McFall, S. M. Nelson, "The Mg2+ion as a template for the synthesis of planar nitrogen-donor macrocyclic ligands. Pentagonal bipyramidal MgII complexes" Journal of the Chemical Society, Chemical Communications 1975, 20, 818-19.
M. G. B. Drew, J. Grimshaw, P. D. A. McIlroy, S. M. Nelson, "Seven-coordination in metal complexes of quinquedentate macrocyclic ligands. III. Iron(II) complexes of 2,13-dimethyl-3,6,9,12,18-pentaazabicyclo[12.3.1] octadeca-1(18),2,12,14,16-pentaene and 2,14-dimethyl-3,6,10,13,19-pentaazabicyclo[13.3.1]nonadeca-1(19),13,15,17-pentaene" Journal of the Chemical Society, Dalton Transactions: Inorganic Chemistry (1972-1999) 1976, 14, 1388-94.
M. G. B. Drew, A. H. Bin Othman, S. M. Nelson, "Seven coordination in metal complexes of quinquedentate macrocycle ligands. Part IV. Crystal and molecular structures of two pentagonal bipyramidal iron(II) complexes" Journal of the Chemical Society, Dalton Transactions: Inorganic Chemistry (1972-1999) 1976, 14, 1394-9.
M. G. B. Drew, A. H. bin Othman, P. McIlroy, S. M. Nelson, "Diaquo-2,13-dimethyl-3,6,9,12,18-pentaazabicyclo [12,3,1] octadeca-1(18),2,12,14,16-pentaeneiron(II) chloride perchlorate" Acta Crystallographica, Section B: Structural Crystallography and Crystal Chemistry 1976, B32(4), 1029-31.
D. H. Cook, D. E. Fenton, M. G. B. Drew, S. G. McFall, S. M. Nelson, "Seven-coordination in metal complexes of quinquedentate macrocyclic ligands. Part 6. Magnesium complexes of macrocyclic ligands containing nitrogen and Oxygen donor atoms" Journal of the Chemical Society, Dalton Transactions: Inorganic Chemistry (1972-1999) 1977, 5, 446-9.
S. M. Nelson, P. D. A. McIlroy, C. S. Stevenson, E. Koenig, G. Ritter, J. Waigel, "Quadridentate versus quinquedentate coordination of some N5 and N3O2 macrocyclic ligands and an unusual thermally controlled quintet singlet spin transition in an iron(II) complex" Journal of the Chemical Society, Dalton Transactions: Inorganic Chemistry (1972-1999) 1986, 991-5.
E. Koenig, G. Ritter, J. Dengler, S. M. Nelson, "Detailed study of a two-step quintet <-> singlet spin transition in an iron (II) complex with a N3O2 macrocyclic ligand and the kinetics of the quintet→singlet relaxation in the temperature range 115-130 K" Inorganic Chemistry 1987, 26(21), 3582-8.
S. Hayami, Z. Gu, Y. Einaga, Y. Kobayasi, Y. Ishikawa, Y. Yamada, A. Fujishima, O. Sato, "A Novel LIESST Iron(II) Complex Exhibiting a High Relaxation Temperature" Inorganic Chemistry 2001, 40(13), 3240-3242.
P. Guionneau, F. Le Gac, A. Kaiba, J. S. Costa, D. Chasseau, J.-F. Letard, "A reversible metal-ligand bond break associated to a spin-crossover" Chemical Communications 2007, 36, 3723-3725.
D. P. Riley, R. H. Weiss, "Manganese macrocyclic ligand complexes as mimics of superoxide dismutase" Journal of the American Chemical Society 1994, 116(1), 387-8.
A. Dees, A. Zahl, R. Puchta, N. J. R. Van Eikema Hommes, F. W. Heinemann, I. Ivanovic-Burmazovic, "Water Exchange on Seven-

(56) References Cited

OTHER PUBLICATIONS

Coordinate Mn(II) Complexes with Macrocyclic Pentadentate Ligands: Insight in the Mechanism of Mn(II) SOD Mimetics" Inorganic Chemistry 2007, 46(7), 2459-2470.

M. R. Filipovic, K. Duerr, M. Mojovic, V. Simeunovic, R. Zimmermann, V. Niketic, I. Ivanovic-Burmazovic, "NO dismutase activity of seven-coordinate manganese (II) pentaazamacrocyclic complexes" Angewandte Chemie, International Edition 2008, 47(45), 8735-8739.

M. Maschke, M. Lieb, N. Metzler-Nolte, "Biologically Active Trifluoromethyl-Substituted Metallocene Triazoles: Characterization, Electrochemistry, Lipophilicity, and Cytotoxicity" European Journal of Inorganic Chemistry 2012, 36, 5953-5959.

W. Radecka-Paryzek, V. Patroniak-Krzyminiewska, "Yttrium(III) complexes of pentadentate Schiff base macrocyclic igands with N3O2 and N5 set of donor atoms" Polyhedron 1995, 14(15/16), 2059-62.

V. Patroniak-Krzyminiewska, W. Radecka-Paryzek, "Azaoxa macrocyclic and acyclic complexes of lanthanides" Collection of Czechoslovak Chemical Communications 1998, 63(3), 363-370.

E. L. Gavey, Y. Beldjoudi, J. M. Rawson, T. C. Stamatatos, M. Pilkington, "Slow relaxation in the first penta-aza Dy(III) macrocyclic complex" Chemical Communications 2014, 50(28), 3741-3743.

E. L. Gavey, M. Pilkington, "Coordination complexes of 15-membered pentadentate aza, oxoaza and thiaaza Schiff base macrocycles Old Complexes Offer New Attractions" Coordination Chemistry Reviews 2015, 296, 125-152.

D. H. Cook, D. E. Fenton, "Calcium, strontium, and barium complexes of pyridyl-containing macrocyclic Schiff bases" Journal of the Chemical Society, Dalton Transactions: Inorganic Chemistry (1972-1999) 1979, 266-72.

D. Lieb, F. C. Friedel, M. Yawer, A. Zahl, M. M. Khusniyarov, F. W. Heinemann, I. Ivanovic-Burmazovic, "Dinuclear Seven-Coordinate Mn(II) Complexes: Effect of Manganese(II)-Hydroxo Species on Water Exchange and Superoxide Dismutase Activity" Inorganic Chemistry 2013, 52(1), 222-236.

C. S. Bonnet et al, "Pyridine-Based Lanthanide Complexes Combining MRI and NIR Luminescence Activities" Chemistry—A European Journal 2012, 18(5), 1419-1431.

B. Drahos, J. Kotek, P. Hermann, I. Lukes, E. Toth, "Mn2+ Complexes with pyridine-containing 15-membered macrocycles: thermodynamic, kinetic, crystallographic, and 1H/17O relaxation studies" Inorganic Chemistry 2010, 49 (7), 3224-3238.

B. Drahos, I. Lukes, E Toth, "Manganese(II) Complexes as Potential Contrast Agents for MRI" European Journal of Inorganic Chemistry 2012, 2012(12), 1975-1986.

P. K. Pal, A. Samii, D. Calne, "Manganese Neurotoxicity: A Review of Clinical Features, Imaging and Pathology" Neurotoxicology 1999, 20, 227-238.

T. Grobner, Nephrol. "Gadolinium — a specific trigger for the development of nephrogenic fibrosing dermopathy and nephrogenic systemic fibrosis?" Dial. Transplant. 2006, 21, 1104-1108.

R. M. Petoral Jr, F. Soderlind, A. Klasson, A. Suska, M. A. Fortin, N. Abrikossova, L. SelegÅard, P.-O Kall, M. Engstrom, K. Uvdal, "Synthesis and Characterization of Tb3+-Doped Gd2O3 Nanocrystals: A Bifunctional Material with Combined Fluorescent Labeling and MRI Contrast Agent Properties" J. Phys. Chem. C 2009, 113, 6913-6920.

L. Frullano, T. Meade, "Multimodal MRI contrast agents" J. Biol. Inorg. Chem. 2007, 12, 939-949.

S. M. Janib, A. S. Moses, J. A. MacKay, "Imaging and drug delivery using theranostic nanoparticles" Adv. Drug Deilv. Rev. 2010, 62, 1052-1063.

D. Pan, S. D. Caruthers, G. Hu, A. Senpan, M. J. Scott, P. J. Gaffney, S. A. Wickline, G. M. Lanza, "Ligand-Directed Nanobialys as Theranostic Agent for Drug Delivery and Manganese-Based Magnetic Resonance Imaging of Vascular Targets" J. Am. Chem. Soc. 2008, 130, 9186-9187.

K. S. Samkoe, S.C. Davis, S. Srinivasan, J.A. O'Hara, T. Hasan, B.W. Pogue, "A Study of MRI-Guided Diffuse Fluorescence Molecular Tomography for Monitoring PDT Effects in Pancreas Cancer". Photodynamic Therapy: Back to the Future, edited by D.H. Kessel, Proc. of SPIE vol. 7380, 73803M, 2009.

P. Ascenzi, A. Bocedic, M. Marino, "Structure—function relationship of estrogen receptor alpha and beta: Impact on human health" Mol. Aspects Med. 2006, 27(4), 299-402.

Kin-Mang Lau, S. C. Mok, S.-M. Ho, "Expression of human estrogen receptor-alpha and-beta, progesterone receptor, and androgen receptor mRNA in normal and malignant ovarian epithelial cells" PNAS, 1999, 96(10), 5722-5727.

E. Weiderpass, I. Persson, H. Melhus, S. Wedréen, A. Kindmark and, J. A. Baron, "Etrogen receptor alpha gene polymorphisms and endometrial cancer risk" Carcinogenesis 2000, 21(4), 623-627.

Y. Arao, K. J. Hamilton, E. H. Goulding, K S. Janardhan, E.M. Eddy, K. S. Korach, "Transactivating function (AF) 2-mediated AF-1 activity of estrogen receptor alpha is crucial to maintain male reproductive tract function" PNAS 2012, 109(51), 21140-21145.

A. Frank, L. M. Brown, D. J. Clegg, "The role of hypothalamic estrogen receptors in metabolic regulation" Front. Neuroendocrin. 2014, 35(4), 550-557.

S. Bord, A. Homer, S. Beavan, J. Compston, "Estrogen Receptors alpha and beta Are Differentially Expressed in Developing Human Bone" JCEM 2001, 86(5), 2309-2314.

A. B. Ropero, M. Eghbali, T. Y. Minosyan, G. Tang, L. Toro, E. Stefani, "Heart estrogen receptor alpha: Distinct membrane and nuclear distribution patterns and regulation by estrogen" J. Mol. Cell. Cardiol. 2006, 41(3), 496-510.

S. Mollerup, K Jǿrgensen, G. Berge, A. Haugen, "Expression of estrogen receptors alpha and beta in human lung tissue and cell lines" Lung Cancer 2002, 37(2), 153-159.

Y. G. Assaraf, C. P. Leamon, J. A. Reddy, "The folate receptor as a rational therapeutic target for personalized cancer treatment" Drug Resist. Update 2014, 17(4-6), 89-95.

P. De, S. Gondi, B. Sumerline, "Folate-Conjugated Thermoresponsive Block Copolymers: Highly Efficient Conjugation and Solution Self-Assembly" Biomacromol. 2008, 9, 1064-1070.

L.D. Lavis, R.T. Raines, "Bright Ideas for Chemical Biology" ACS Chem. Biol. 2008, 3(3), 142-155.

E. Heyer et al., "Highly Fluorescent and Water-Soluble Diketopyrrolopyrrole Dyes for Bioconjugation" Angew. Chem. Int. Ed. 2015, 54, 2995-2999.

V. V. Rostovtsev, L. G. Green, V. V. Fokin, K. B. Sharpless, "A Stepwise Huisgen Cycloaddition Process: Copper(I)-Catalyzed Regioselective Ligation of Azides and Terminal Alkynes" Angew. Chem., Int. Ed. 2002, 41, 2596-2599.

M. Meldal, C. W. Tornoe, "Cu-Catalyzed Azide-Alkyne Cycloaddition" Chem. Rev. 2008, 108, 2952-3015.

V. O. Rodionov, S. I. Presolski, S. Gardinier, Y.-H. Lim, "Benzimidazole and Related Ligands for Cu-Catalyzed Azide-Alkyne Cycloaddition" J. Am. Chem. Soc. 2007, 129(42), 12696-12704.

S. Diez-Gonzé alez, A. Correa, L. Cavallo, S. P. Nolan, "(NHC)Copper(i)-Catalyzed [3+2] Cycloaddition of Azides and Mono- or Disubstituted Alkynes" Chem. Eur. J. 2006, 12(29), 7558-7564.

T. Nakamura, T. Terashima, K. Ogata, S. Fukuzawa, "Copper(I) 1,2,3-Triazol-5-ylidene Complexes as Efficient Catalysts for Click Reactions of Azides with Alkynes" Org. Lett. 2011, 13(4), 620-623.

A. Mirfazaelian, J. W. Fisher, "Organ Growth Functions in Maturing Male Sprague-Dawley Rats Based on a Collective Database" J. Toxicol. Environ. Health 2007, 70, 1052-1063.

H. Takalo, J. Kankare, "Synthesis of dimethyl and diethyl 4-(Phenylethynyl)-2,6-pyridinedicarboxylate" Acta Chem. Scand. B 1987, 41, 219-221.

A. Sidibe, F. Hamon, E. Largy, D. Gomez, M.-P. Teulade-Fichou, C. Trentesaux, J.-F. Riou, "Effects of a halogenated G-quadruplex ligand from the pyridine dicarboxamide series on the terminal sequence of XpYp telomere in HT1080 cells" Biochimie 2012, 94, 2559-2568.

R.-A. Fallahpour, E. C. Constable, "Novel synthesis of substituted 4'-hydroxy-2,2':6',2-terpyridines" J. Chem. Soc. Perkin Trans. 1 1997, 2263-2264.

Y. Oikawa, K. Sugano, O. Yonemitsu, "Meldrum's Acid in Organic Synthesis. 2. A General and Versatile Synthesis of beta-Keto Esters" J. Org. Chem. 1978, 43, 2087-2088.

(56) References Cited

OTHER PUBLICATIONS

O. I. Bol'shakov, I. O. Lebedyeva, A. R. Katritzky, "17alpha-Ethynylestradiol Peptide Labeling by 'Click' Chemistry Synthesis" 2012, 44, 2926-2932.

H.-Y. Kim, J. Sohn, G. T. Wijewickrama, P. Edirisinghe, T. Gherezghiher, M. Hemachandra, P.-Y. Lu, R. E. Chandrasena, M. E. Molloy, D. A. Tonetti, G. R. J. Thatcher, "Click synthesis of estradiol—cyclodextrin conjugates as cell compartment selective estrogens" Bioord. Med. Chem. 2010, 18, 809-821.

K. P. Madeira, R. D. Daltoé, G. M. Sirtoli, A. A. Carvalho, L. B. A. Rangel, I. V. Silva, "Estrogen receptor alpha (ERS1) SNPs c454-397T>C (PvuII) and c454-351A>G (XbaI) are risk biomarkers for breast cancer development" Mol. Biol. Rep. 2014, 41, 5459-5466.

J. Thundimadathil, "Click chemistry in peptide science: a mini-review. Synthesis of clickable peptides and applications" Chemistry Today, vol. 31(2), Mar./Apr. 2013.

R. T. Acha, E. L. Gavey, J. Wang, J. M. Rawson, M. Pilkington, The First 1-D Cyanide-bridged Complex Assembled From a Covalently Tethered [CoII(N3O2)Cl(OH2)]22+Macrocyclic Building Block. Apr. 12, 2014, vol. 76, pp. 122-127.

S. C. Jackels, M. M. Durham, J. E. Newton, T. C. Henninger, Aqueous Proton NMR Relaxation Enhancement by Manganese (II) Macrocyclic Complexes: Structure-Relaxivity Relationships. Inorg. Chem., vol. 31:2, 1992, pp. 234-239.

E.L. Gavey and M. Pilkinton, Schiff-base Macrocycles as a Platform for Small Molecule-Based Targeted MRI Contrast Agents, 98th Canadian Chemistry Conference and Exhibition, Conference Abstract, available online: Apr. 17, 2015.

E.L. Gavey, D. Johnston, and M. Pilkington, 'Click' Chemistry: the CuAAC Reaction as a Means of Functionalization, 10th Annual Brock Chemistry Undergraduate Student Research Day, Poster, Aug. 21, 2014.

E. Gavey, A. Pham, J. Regier, M. Al Hareri, L. Wlodarek and M. Pilkington, Exploiting the "Attractive" Properties of Macrocycles for Quantum Computing and Medical Diagnostics, Brock Research Celebration, Poster, Feb. 10, 2015.

R. D. Cannon, B. Chiswell, L. M. Venanzi, Abstract: Some Complexes of Cobalt (II), Nickel (II), and Palladium(II), with Multidentate Ligands and the Ligand Field Strength of Co-ordinated Ethers and Sulphides. J. Chem. Soc. A, Issue: 0 1967, pp. 1277-1281.

R. Moreno-Corral, H. Höpfl, L. Machi-Lara, K. O. Lara, Synthesis, Structural Characterization and Metal Inclusion Properties of 18 -, 20 - and 22 - Membered Oxaazacyclophanes and Oxaazacallx[4]arene Analogues: Macrocyclic Amine and Schiff Base Receptors with Variable NxOy Donor Sets. Eur. J. Org. Chem., Mar. 7, 2011, pp. 2148-2162.

P. Caravan, J. J. Ellison, T. J. McMurry, R. B. Lauffer, Gadolinium(III) Chelates as MRI Contrast Agents: Structure, Dynamics, and Applications. Chem. Rev., Aug. 20, 1999, vol. 99, pp. 2293-2352.

P. Hermann, J. Kotek, V. Kubíček, I. Lukeš, Gadolinium(III) Complexes as MRI Contrast Agents: Ligand Design and Properties of the Complexes. Dalton Trans., Mar. 27, 2008, pp. 3027-3047.

\* cited by examiner

METHODS AND COMPOUNDS FOR ENHANCING CONTRAST IN MAGNETIC RESONANCE IMAGING (MRI)

CROSS-REFERENCE TO RELATED APPLICATIONS

The present application claims the benefit of priority from U.S. provisional application No. 62/174,752 filed on Jun. 12, 2015, the contents of which are incorporated herein by reference in their entirety.

FIELD

The present application relates to methods and compounds for enhancing contrast in magnetic resonance imaging. The present application also relates to bifunctional contrast agents, methods for their use and preparation as well as to intermediate compounds used in such a method of preparation.

BACKGROUND

Magnetic resonance imaging (MRI) has become increasingly important in the detection, diagnosis and monitoring of diseases due, for example to the flexibility of the method, and the detail of the images produced. For example, this non-invasive technique produces 2- and 3-D images with sub-mm spatial resolution, without the use of ionizing radiation.

The majority of the 1.5 million MRI scans presently performed in Canada each year involve the use of contrast agents; compounds containing paramagnetic metal ions which enhance the contrast, for example, between healthy and diseased tissue. Contrast agents operate by altering the local magnetic field strength of a tissue and changing the relaxation times ($T_1$ and $T_2$, in s) of the surrounding water protons. The effectiveness of a contrast agent is described by its relaxivities, $r_1$ and $r_2$ ($s^{-1} \cdot mM^{-1}$), where $r_1=(1/T_1)/c$ and $r_2=(1/T_2)/c$, and c is the concentration of the contrast agent in a given media.

High values of $r_1$ and $r_2$ are useful. Optimizing relaxivity involves maximizing several parameters. For example, relaxivity increases as the rate of molecular tumbling ($\tau_R$) decreases, and as the rate of water exchange increases. Relaxivity also increases with the number of coordinated water molecules, q. These parameters are depicted in FIG. 1.

There are eight small-molecule contrast agents presently authorized for use in Canada. All are made up of a single $Gd^{III}$ ion and either a chelating diethylenetriaminepentaacetate ($DTPA^{5-}$)-based ligand, or a macrocyclic 1,4,7,10-tetraazacyclododecane-1,4,7,10-tetraacetate ($DOTA^{4-}$)-based ligand (Scheme 1). The $Mn^{II}$-based agent Teslascan™ based on the ligand dipyridoxal diphosphate ($DPDP^{2-}$; Scheme 1) has also been utilized, but was recently removed from the market.

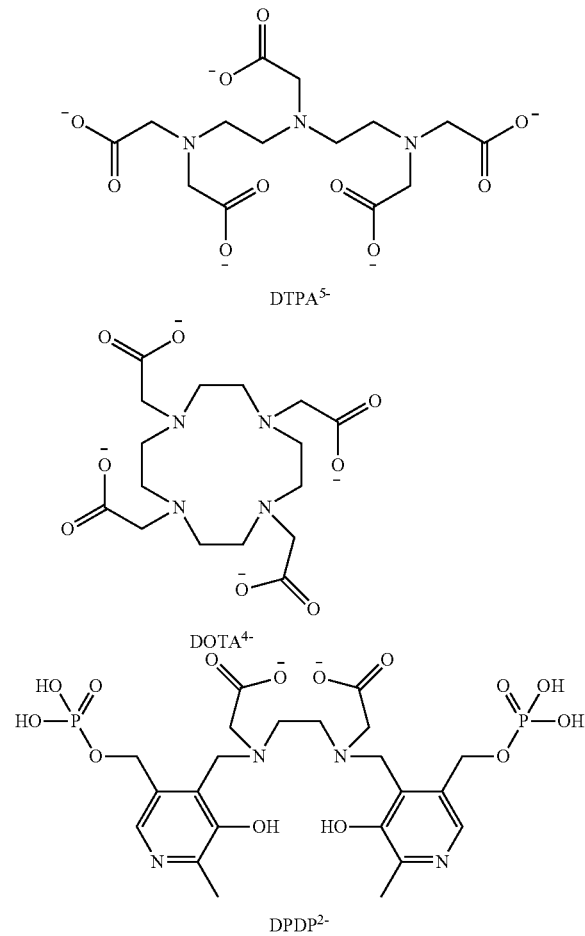

Scheme 1. Base ligands of which derivatives thereof are found in approved contrast agents.

The major drawback to the currently approved $Mn^{II}$- and $Gd^{III}$-based agents is the biotoxicity of the free metal ions. $Mn^{II}$ dissociates quickly from the $DPDP^{2-}$ ligand, and has neurotoxic effects. The ion is readily transported across the blood-brain barrier, where it accumulates and causes Parkinson-like symptoms, including tremors and muscle stiffness.[1] $Gd^{III}$ is strongly associated with nephrogenic systemic fibrosis (NSF), an acquired disorder in patients with suppressed renal function involving a hardening of the skin, the muscles of the heart, and the walls of organs such as the liver.[2] There is thus ongoing research into safer, more effective alternatives to the approved contrast agents.

Dual-property imaging agents; for instance, bi-modality imaging species combining MRI properties with fluorescence[3], or 'theranostic' agents which both image and deliver medicinal benefits[4] have also been disclosed.

The most common techniques used to study the dyes comprising a fluorescent group are co-facial microscopy, optical imaging and fluorescence microscopy. Prior to being used in such techniques, the fluorescence properties of the individual compounds can be first studied with a spectrofluorometer.

In vitro cellular fluorescence imaging is typically carried out using a confocal microscope. In this respect, a confocal microscope is usually used to measure the intensity of the emitted fluorescence signal and create a digital image. In contrast to widefield microscopy, confocal microscopy has an increased optical resolution and contrast. It uses point illumination and a spatial pinhole in front of the detector to restrict passage of light that comes from the plane of focus. Out-of-focus light from specimens that are thicker than the focal plane is thereby eliminated. The thickness of the focal plane is largely determined by the emission wavelength and the numerical aperture of the object lens. In confocal microscopy, only one point in the sample is illuminated at a time. In order to take 2D or even 3D images one must therefore scan over the specimen. Post-processing of images taken by confocal microscopy makes it possible to depict and quantitate the obtained signals.

In MRI-guided fluorescence tomography (in vivo dual-imaging), magnetic resonance (MR) image sequences are collected simultaneously with fluorescence signals using a MR-coupled diffuse optical tomography system. Image reconstruction is generally performed multiple times with varying abdominal organ segmentation in order to obtain an optimal tomographic image. This has been used to follow the treatment/progress of cancer tumours since the fluorescence is greater in the diseased tissue. For example, Samkoe et al. disclose a MR-guided diffuse optical tomography system wherein the fluorescence system is made up of a CW laser (690 nm), rotating source coupling stage, 16 spectrometers and 16 long, bifurcated source-detector optical fibers which are channeled through a conduit in the wall and couple directly into the bore of the MRI[5].

Complexes of the bis-amine macrocycles depicted in Scheme 2 have been investigated as imaging agents. However, the biological activity of these compounds is complicated by their ability to act as superoxide dismutase mimics.

Scheme 2. Bis-amine macrocyclic ligands investigated for use in imaging agents.

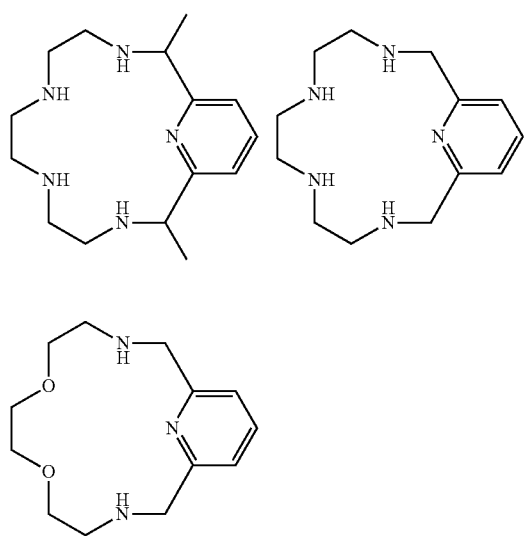

[1+1] Schiff-base macrocycles can be formed by the metal-templated condensation of a diketone and a diamine. The MnCl$_2$-templated formation of macrocycles L1 and L2 is shown in Scheme 3, resulting in complexes 1 and 2 respectively. These two complexes have been previously reported, and studied as building blocks for the synthesis of magnetically interesting chains and clusters.[6]

Scheme 3. Metal-templated Schiff-base macrocycle formation of L1 and L2 around MnCl$_2$, to give complexes 1 and 2.

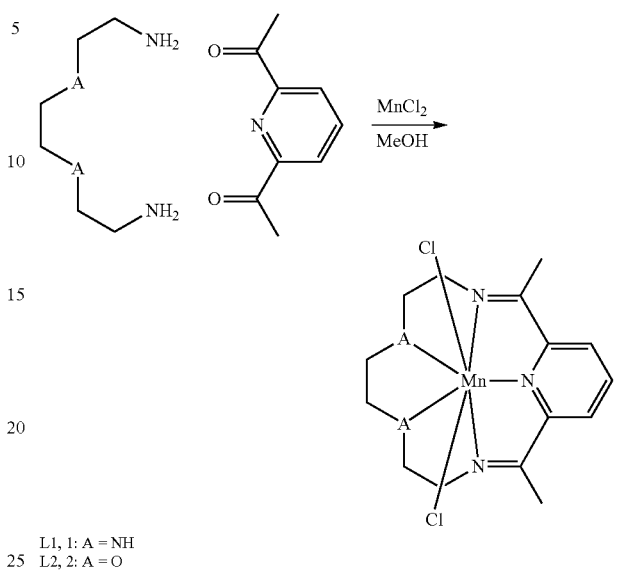

L1, 1: A = NH
L2, 2: A = O

The biodistribution of a small-molecule, non-targeted contrast agent typically follows the sequence: (1) intravenous injection; (2) distribution in the blood; (3) distribution in the extracellular space; and (4) pathway through the excretory organs. Such agents are known as extracellular fluid (ECF) agents.

From the extracellular space, an agent may or may not be taken up into the intracellular environment of an organ or organs, depending on its structure. Uptake may be active or passive.

There are nine small-molecule contrast agents presently approved for use in North America (Table 1)[7]. Magnevist™, Omniscan™, OptiMARK™ Dotarem™, Prohance™, and Gadavist™ are ECF agents, and are used for whole-body and CNS imaging. They are excreted primarily through the kidneys with an average half-life of 1.5 hours.

The agents Primovist™ and Multihance™ are also ECF agents, but their structures contain benzyl groups, so they are taken up by hepatocytes during excretion: thus are useful as liver-specific imaging agents.

In contrast, the approved agent Ablavar™ selectively binds to the blood protein serum albumin, and thus remains in the vascular system as a blood pool agent, suitable for imaging vasculature.

There are a number of parameters which are selected for a given MRI scan, including[8]: magnetic field strength; RF (radiofrequency) pulse timing; TE: echo time (ms); TR: repetition time (ms); RF pulse amplitude; and gradient timing and amplitude. MRI sequences can be classified by the type of sequence (such as spin-echo, gradient-echo, or inversion recovery) but are more commonly described by the image weighting:

$T_1$ weighted: short TE and short TR
$T_2$ weighted: long TE and long TR
Proton density (PD) weighted: short TE, long TR.

A given tissue is usually evaluated by multiple sequences, collectively known as the MRI protocol. The same contrast agent may, for example give rise to different tissue enhancement under a different sequence.

SUMMARY

The $Mn^{II}$- and $Gd^{III}$-based Schiff-base macrocyclic complexes disclosed herein have been shown to be useful as potential contrast agents. The compounds display high relaxivity values, and have useful stability in solution due to the bis-imine character of the macrocyclic ligands. A synthetic pathway to an azido-functionalized pyridine head-unit is also disclosed, providing a useful intermediate for the development of bi-functional contrast agents based on such complexes. Toxicity and imaging studies on three of the prepared complexes show that these agents exhibit low biotoxicity and good imaging potential.

Accordingly, the present application includes a compound of Formula I(a) or a hydrate thereof:

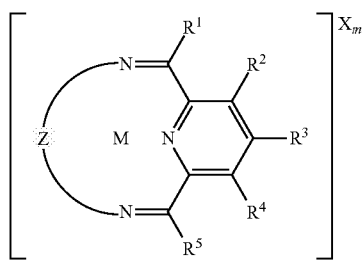

wherein
R$^1$ and R$^5$ are each independently $C_{1-6}$alkyl or aryl;
R$^2$ and R$^4$ are each independently H, —OH, halo, $C_{1-6}$alkyl, aryl or $C_{1-3}$alkyleneC(O)OR$^6$, wherein R$^6$ is H or $C_{1-6}$alkyl;
R$^3$ is

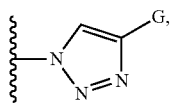

wherein G is a targeting group or a fluorescent probe;
X is a pharmaceutically acceptable counteranion;
Z is —(CR$^7$R$^8$═CR$^9$R$^{10}$-A)$_p$-(CR$^{11}$R$^{12}$═CR$^{13}$R$^{14}$)—;
wherein
A is O or NH;
p is 2, 3 or 4;
═ represents a single or double bond;
when ═ is a double bond, one of R$^7$/R$^8$ and R$^9$/R$^{10}$ or R$^{11}$/R$^{12}$ and R$^{13}$/R$^{14}$, as applicable, is not present; and
R$^7$ to R$^{14}$ are each independently H, $C_{1-6}$alkyl or aryl; or one of R$^7$/R$^8$ and R$^9$/R$^{10}$ and/or R$^{11}$/R$^{12}$ and R$^{13}$/R$^{14}$, together with the carbon atoms to which they are attached, form a 5-6 membered carbocycle;
the N and A atoms in the compound of Formula I(a) form an $N_3A_p$ donor set for coordinating with M;
M is selected from $Fe^{3+}$, $Fe^{2+}$, $Co^{2+}$, $Zn^{2+}$, $Mn^{3+}$, $Mn^{2+}$ and $Gd^{3+}$ and is coordinated in an equatorial fashion by at least three atoms of the $N_3A_p$ donor set;
when M is $Fe^{2+}$, $Co^{2+}$, $Zn^{2+}$ or $Mn^{2+}$, m is 2; and
when M is $Fe^{3+}$, $Mn^{3+}$ or $Gd^{3+}$, m is 3.
In an embodiment, in the compound of Formula I(a) or the hydrate thereof, M is $Mn^{2+}$ or $Gd^{3+}$, when M is $Mn^{2+}$, m is 2 and when M is $Gd^{3+}$, m is 3.

The present application also includes a method of preparing a compound of Formula I(a):

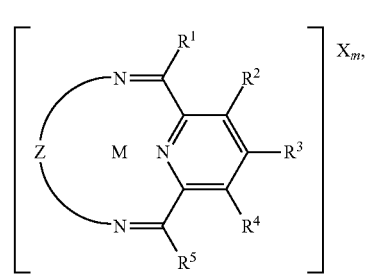

wherein
R$^1$ and R$^5$ are each independently $C_{1-6}$alkyl or aryl;
R$^2$ and R$^4$ are each independently H, —OH, halo, $C_{1-6}$alkyl, aryl or $C_{1-3}$alkyleneC(O)OR$^6$, wherein R$^6$ is H or $C_{1-6}$alkyl;
R$^3$ is

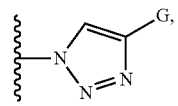

wherein G is a targeting group or a fluorescent probe;
X is a pharmaceutically acceptable counteranion;
Z is —(CR$^7$R$^8$═CR$^9$R$^{10}$-A)$_p$-(CR$^{11}$R$^{12}$═CR$^{13}$R$^{14}$)—;
wherein
A is O or NH;
p is 2, 3 or 4;
═ represents a single or double bond;
when ═ is a double bond, one of R$^7$/R$^8$ and R$^9$/R$^{10}$ or R$^{11}$/R$^{12}$ and R$^{13}$/R$^{14}$, as applicable, is not present; and
R$^7$ to R$^{14}$ are each independently H, $C_{1-6}$alkyl or aryl; or one of R$^7$/R$^8$ and R$^9$/R$^{10}$ and/or R$^{11}$/R$^{12}$ and R$^{13}$/R$^{14}$, together with the carbon atoms to which they are attached, form a 5-6 membered carbocycle;
the N and A atoms in the compound of Formula I(a) form an $N_3A_p$ donor set for coordinating with M;
M is selected from $Fe^{3+}$, $Fe^{2+}$, $Co^{2+}$, $Zn^{2+}$, $Mn^{3+}$, $Mn^{2+}$ and $Gd^{3+}$ and is coordinated in an equatorial fashion by at least three atoms of the $N_3A_p$ donor set;
when M is $Fe^{2+}$, $Co^{2+}$, $Zn^{2+}$ or $Mn^{2+}$, m is 2; and
when M is $Fe^{3+}$, $Mn^{3+}$ or $Gd^{3+}$, m is 3,
the method comprising:
(a) reacting an azide of Formula II:

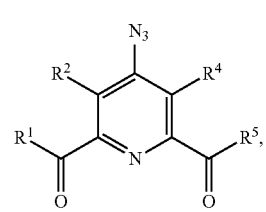

wherein
R$^1$ and R$^5$ are each independently $C_{1-6}$alkyl or aryl; and
R$^2$ and R$^4$ are each independently H, —OH, halo, $C_{1-6}$alkyl, aryl or $C_{1-3}$alkyleneC(O)OR$^6$, wherein R$^6$ is H or $C_{1-6}$alkyl, with an alkyne of Formula III:

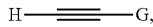     (III)

wherein G is a targeting group or a fluorescent probe, in the presence of a copper catalyst to obtain a compound of Formula IV:

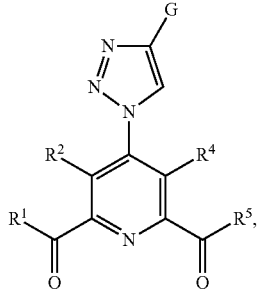     (IV)

wherein
R$^1$ and R$^5$ are each independently $C_{1-6}$alkyl or aryl;
R$^2$ and R$^4$ are each independently H, —OH, halo, $C_{1-6}$alkyl, aryl or $C_{1-3}$alkyleneC(O)OR$^6$, wherein R$^6$ is H or $C_{1-6}$alkyl; and
G is a targeting group or a fluorescent probe, and
(b) reacting the compound of Formula IV with a compound of Formula V:

MX$_m$     (V), wherein
X is a pharmaceutically acceptable counteranion;
M is selected from Fe$^{3+}$, Fe$^{2+}$, Co$^{2+}$, Zn$^{2+}$, Mn$^{3+}$, Mn$^{2+}$ and Gd$^{3+}$;
when M is Fe$^{2+}$, Co$^{2+}$, Zn$^{2+}$ or Mn$^{2+}$, m is 2; and
when M is Fe$^{3+}$, Mn$^{3+}$ or Gd$^{3+}$, m is 3,
and a diamine of Formula VI:

     (VI)

wherein
Z is —(CR$^7$R$^7$═CR$^9$R$^{10}$-A)$_p$-(CR$^{11}$R$^{12}$═CR$^{13}$R$^{14}$);
wherein
A is O or NH;
p is 2, 3 or 4;
═ represents a single or double bond;
when ═ is a double bond, one of R$^7$/R$^8$ and R$^9$/R$^{10}$ or R$^{11}$/R$^{12}$ and R$^{13}$/R$^{14}$, as applicable, is not present; and
R$^7$ to R$^{14}$ are each independently H, $C_{1-6}$alkyl or aryl; or
one of R$^7$/R$^8$ and R$^9$/R$^{10}$ and/or R$^{11}$/R$^{12}$ and R$^{13}$/R$^{14}$, together with the carbon atoms to which they are attached, form a 5-6 membered carbocycle;
under conditions to obtain the compound of Formula I(a).

The present application also includes an alternative method of preparing a compound of Formula I(a):

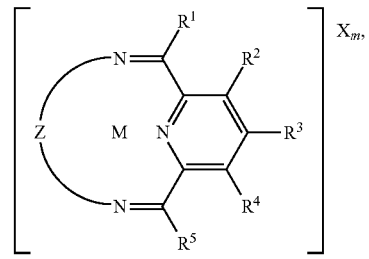     I(a)

wherein
R$^1$ and R$^5$ are each independently $C_{1-6}$alkyl or aryl;
R$^2$ and R$^4$ are each independently H, —OH, halo, $C_{1-6}$alkyl, aryl or $C_{1-3}$alkyleneC(O)OR$^6$, wherein R$^6$ is H or $C_{1-6}$alkyl;
R$^3$ is

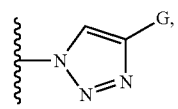

wherein G is a targeting group or a fluorescent probe;
X is a pharmaceutically acceptable counteranion;
Z is —(CR$^7$R$^8$═CR$^9$R$^{10}$-A)$_p$-(CR$^{11}$R$^{12}$═CR$^{13}$R$^{14}$)—;
wherein
A is O or NH;
p is 2, 3 or 4;
═ represents a single or double bond;
when ═ is a double bond, one of R$^7$/R$^8$ and R$^9$/R$^{10}$ or R$^{11}$/R$^{12}$ and R$^{13}$/R$^{14}$, as applicable, is not present; and
R$^7$ to R$^{14}$ are each independently H, $C_{1-6}$alkyl or aryl; or
one of R$^7$/R$^8$ and R$^9$/R$^{10}$ and/or R$^{11}$/R$^{12}$ and R$^{13}$/R$^{14}$, together with the carbon atoms to which they are attached, form a 5-6 membered carbocycle;
the N and A atoms in the compound of Formula I(a) form an N$_3$A$_p$ donor set for coordinating with M;
M is selected from Fe$^{3+}$, Fe$^{2+}$, Co$^{2+}$, Zn$^{2+}$, Mn$^{3+}$, Mn$^{2+}$ and Gd$^{3+}$ and is coordinated in an equatorial fashion by at least three atoms of the N$_3$A$_p$ donor set;
when M is Fe$^{2+}$, Co$^{2+}$, Zn$^{2+}$ or Mn$^{2+}$, m is 2; and
when M is Fe$^{3+}$, Mn$^{3+}$ or Gd$^{3+}$, m is 3,
the method comprising:
(a) reacting an azide of Formula II:

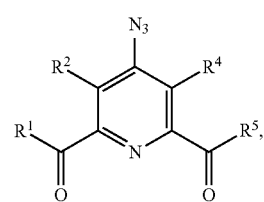     (II)

wherein
R$^1$ and R$^5$ are each independently $C_{1-6}$alkyl or aryl; and
R$^2$ and R$^4$ are each independently H, —OH, halo, $C_{1-6}$alkyl, aryl or $C_{1-3}$alkyleneC(O)OR$^6$, wherein R$^6$ is H or $C_{1-6}$alkyl, with a compound of Formula V:

wherein

X is a pharmaceutically acceptable counteranion;

M is selected from $Fe^{3+}$, $Fe^{2+}$, $Co^{2+}$, $Zn^{2+}$, $Mn^{3+}$, $Mn^{2+}$ and $Gd^{3+}$;

when M is $Fe^{2+}$, $Co^{2+}$, $Zn^{2+}$ or $Mn^{2+}$, m is 2; and when M is $Fe^{3+}$, $Mn^{3+}$ or $Gd^{3+}$, m is 3, and a diamine of Formula VI:

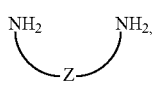

wherein

Z is $-(CR^7R^8\text{=\!=\!=}CR^9R^{10}\text{-A})_p$-$(CR^{11}R^{12}\text{=\!=\!=}CR^{13}R^{14})$—;

wherein

A is O or NH;

p is 2, 3 or 4;

===== represents a single or double bond;

when ===== is a double bond, one of $R^7/R^8$ and $R^9/R^{10}$ or $R^{11}/R^{12}$ and $R^{13}/R^{14}$, as applicable, is not present; and $R^7$ to $R^{14}$ are each independently H, $C_{1-6}$alkyl or aryl; or one of $R^7/R^8$ and $R^9/R^{10}$ and/or $R^{11}/R^{12}$ and $R^{13}/R^{14}$, together with the carbon atoms to which they are attached, form a 5-6 membered carbocycle, under conditions to obtain a compound of Formula I(c):

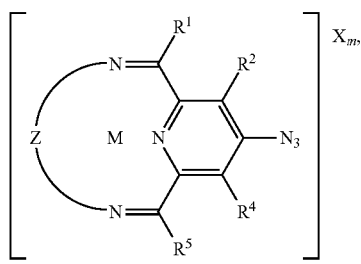

wherein $R^1$ and $R^5$ are each independently $C_{1-6}$alkyl or aryl;

$R^2$ and $R^4$ are each independently H, —OH, halo, $C_{1-6}$alkyl, aryl or $C_{1-3}$alkyleneC(O)OR$^6$, wherein $R^6$ is H or $C_{1-6}$alkyl;

X is a pharmaceutically acceptable counteranion;

Z is $-(CR^7R^8\text{=\!=\!=}CR^9R^{10}\text{-A})_p$-$CR^{11}R^{12}\text{=\!=\!=}CR^{13}R^{14})$—;

wherein

A is O or NH;

p is 2, 3 or 4;

===== represents a single or double bond;

when ===== is a double bond, one of $R^7/R^8$ and $R^9/R^{10}$ or $R^{11}/R^{12}$ and $R^{13}/R^{14}$, as applicable, is not present; and $R^7$ to $R^{14}$ are each independently H, $C_{1-6}$alkyl or aryl; or one of $R^7/R^8$ and $R^9/R^{10}$ and/or $R^{11}/R^{12}$ and $R^{13}/R^{14}$, together with the carbon atoms to which they are attached, form a 5-6 membered carbocycle;

the N and A atoms in the compound of Formula I(c) form an $N_3A_p$ donor set for coordinating with M;

M is selected from $Fe^{3+}$, $Fe^{2+}$, $Co^{2+}$, $Zn^{2+}$, $Mn^{3+}$, $Mn^{2+}$ and $Gd^{3+}$ and is coordinated in an equatorial fashion by at least three atoms of the $N_3A_p$ donor set;

when M is $Fe^{2+}$, $Co^{2+}$, $Zn^{2+}$ or $Mn^{2+}$, m is 2; and when M is $Fe^{3+}$, $Mn^{3+}$ or $Gd^{3+}$, m is 3; and (b) reacting the compound of Formula I(c) with an alkyne of Formula III:

wherein G is a targeting group or a fluorescent probe, in the presence of a copper catalyst to obtain the compound of Formula I(a).

The present application also includes a compound of Formula II:

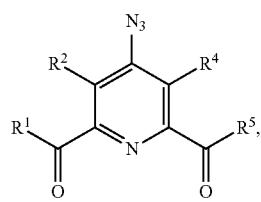

wherein $R^1$ and $R^5$ are each independently $C_{1-6}$alkyl or aryl; and $R^2$ and $R^4$ are each independently H, —OH, halo, $C_{1-6}$alkyl, aryl or $C_{1-3}$alkyleneC(O)OR$^6$, wherein $R^6$ is H or $C_{1-6}$alkyl.

The present application also includes a compound of Formula IV:

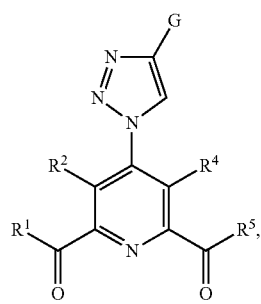

wherein $R^1$ and $R^5$ are each independently $C_{1-6}$alkyl or aryl;

$R^2$ and $R^4$ are each independently H, —OH, halo, $C_{1-6}$alkyl, aryl or $C_{1-3}$alkyleneC(O)OR$^6$, wherein $R^6$ is H or $C_{1-6}$alkyl; and G is a targeting group or a fluorescent probe.

The present application also includes a method of enhancing contrast in a magnetic resonance image of a subject, the method comprising:

(a) administering to the subject, a compound of Formula I(b) or a hydrate thereof:

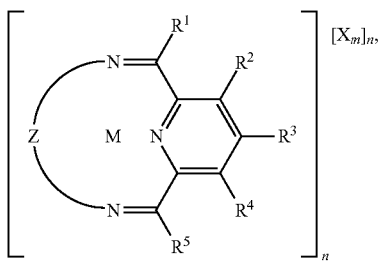

wherein
R¹ and R⁵ are each independently $C_{1-6}$alkyl or aryl;
R² and R⁴ are each independently H, —OH, halo, $C_{1-6}$alkyl, aryl or $C_{1-3}$alkyleneC(O)OR⁶, wherein R⁶ is H or $C_{1-6}$alkyl;
n is 1 or 2;
when n is 1, R³ is H, —OH, halo, $C_{1-6}$alkyl, aryl or $C_{1-3}$alkyleneC(O)OR⁶, wherein R⁶ is H or $C_{1-6}$alkyl;
when n is 2, R³ represents a single bond;
X is a pharmaceutically acceptable counteranion;
Z is —(CR⁷R⁸=CR⁹R¹⁰-A)$_p$-(CR¹¹R¹²=CR¹³R¹⁴)—;
wherein
A is O;
p is 2, 3 or 4;
===== represents a single or double bond;
when ===== is a double bond, one of R⁷/R⁸ and R⁹/R¹⁰ or R¹¹/R¹² and R¹³/R¹⁴, as applicable, is not present; and
R⁷ to R¹⁴ are each independently H, $C_{1-6}$alkyl or aryl; or
one of R⁷/R⁸ and R⁹/R¹⁰ and/or R¹¹/R¹² and R¹³/R¹⁴, together with the carbon atoms to which they are attached, form a 5-6 membered carbocycle;
the N and A atoms in the compound of Formula I(b) form an $N_3A_p$ donor set for coordinating with M;
M is selected from $Fe^{3+}$, $Fe^{2+}$, $Co^{2+}$, $Zn^{2+}$, $Mn^{3+}$, $Mn^{2+}$ and $Gd^{3+}$ and is coordinated in an equatorial fashion by at least three atoms of the $N_3A_p$ donor set;
when M is $Fe^{2+}$, $Co^{2+}$, $Zn^{2+}$ or $Mn^{2+}$, m is 2; and
when M is $Fe^{3+}$, $Mn^{3+}$ or $Gd^{3+}$, m is 3; and
(b) obtaining a magnetic resonance image of the subject.

In an embodiment, the compound of Formula I(b) is

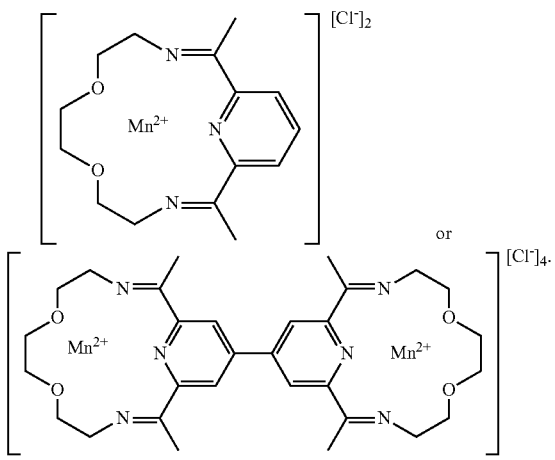

The present application also includes a method of enhancing contrast in a magnetic resonance image of a subject, the method comprising:

(a) administering to the subject, a compound of Formula I(a) or a hydrate thereof:

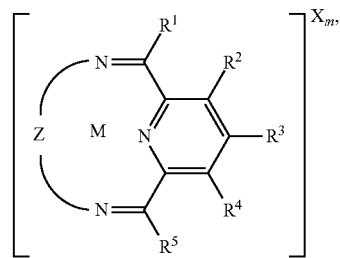

wherein
R¹ and R⁵ are each independently $C_{1-6}$alkyl or aryl;
R² and R⁴ are each independently H, —OH, halo, $C_{1-6}$alkyl, aryl or $C_{1-3}$alkyleneC(O)OR⁶, wherein R⁶ is H or $C_{1-6}$alkyl;
R³ is

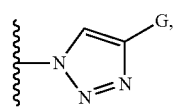

wherein G is a targeting group or a fluorescent probe;
X is a pharmaceutically acceptable counteranion;
Z is —(CR⁷R⁸=CR⁹R¹⁰-A)$_p$-(CR¹¹R¹²=CR¹³R¹⁴)—;
wherein
A is O or NH;
p is 2, 3 or 4;
===== represents a single or double bond;
when ===== is a double bond, one of R⁷/R⁸ and R⁹/R¹⁰ or R¹¹/R¹² and R¹³/R¹⁴, as applicable, is not present; and
R⁷ to R¹⁴ are each independently H, $C_{1-6}$alkyl or aryl; or
one of R⁷/R⁸ and R⁹/R¹⁰ and/or R¹¹/R¹² and R¹³/R¹⁴, together with the carbon atoms to which they are attached, form a 5-6 membered carbocycle;
the N and A atoms in the compound of Formula I(a) form an $N_3A_p$ donor set for coordinating with M;
M is selected from $Fe^{3+}$, $Fe^{2+}$, $Co^{2+}$, $Zn^{2+}$, $Mn^{3+}$, $Mn^{2+}$ and $Gd^{3+}$ and is coordinated in an equatorial fashion by at least three atoms of the $N_3A_p$ donor set;
when M is $Fe^{2+}$, $Co^{2+}$, $Zn^{2+}$ or $Mn^{2+}$, m is 2; and
when M is $Fe^{3+}$, $Mn^3$ or $Gd^{3'}$, m is 3; and
(b) obtaining a magnetic resonance image of the subject.

In an embodiment, G is a targeting group and the method comprises obtaining a magnetic resonance image of a site in the subject that the targeting group targets. In another embodiment, the targeting group has the structure:

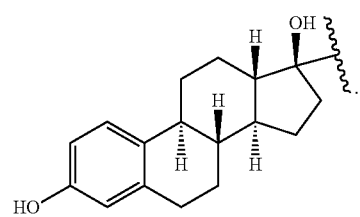

In an alternate embodiment, G is a fluorescent probe and the method further comprises obtaining a fluorescence image of the subject. In another embodiment, the fluorescent probe has the structure:

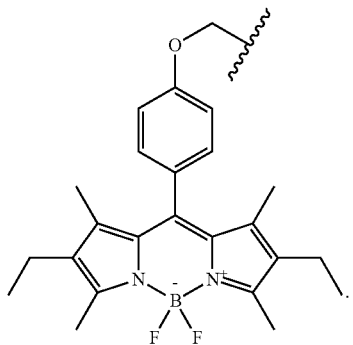

Other features and advantages of the present application will become apparent from the following detailed description. It should be understood, however, that the detailed description and the specific examples while indicating embodiments of the application are given by way of illustration only, since various changes and modifications within the spirit and scope of the application will become apparent to those skilled in the art from this detailed description.

BRIEF DESCRIPTION OF THE DRAWINGS

The present application will now be described in greater detail with reference to the drawings in which.

DETAILED DESCRIPTION

I. Definitions

Figure 1:
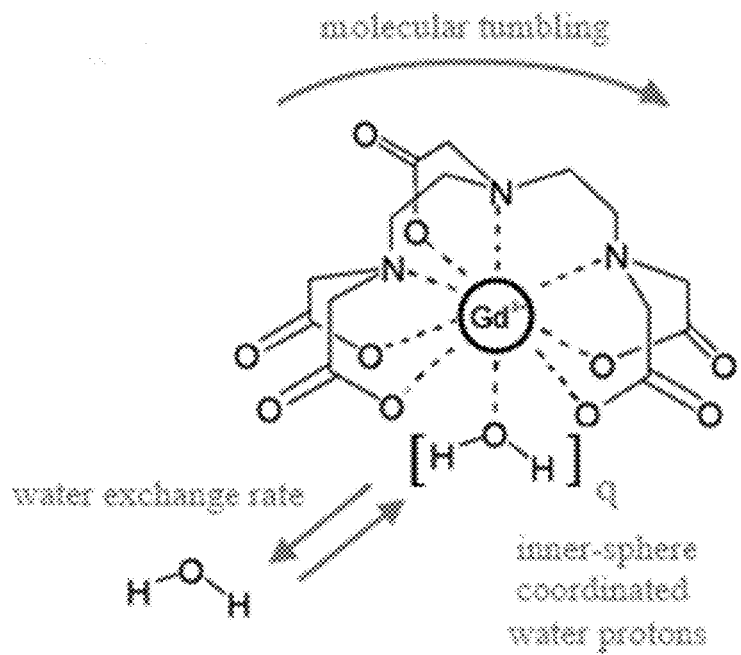
FIG. 1 is a schematic showing known factors affecting relaxivity of a contrast agent for Magnetic Resonance Imaging (MRI).

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "and/or" as used herein means that the listed items are present, or used, individually or in combination. In effect, this term means that "at least one of" or "one or more" of the listed items is used or present.

As used in this application, the singular forms "a", "an" and "the" include plural references unless the content clearly dictates otherwise. For example, an embodiment including "a compound" should be understood to present certain aspects with one compound or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

In embodiments of the present application, the compounds described herein have at least one asymmetric center. Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (for example, less than 20%, suitably less than 10%, more suitably less than 5%) of compounds of the present application having alternate stereochemistry. It is intended that any optical isomers, as separated, pure or partially purified optical isomers or racemic mixtures thereof are included within the scope of the present application.

The term "suitable" as used herein means that the selection of specific reagents or conditions will depend on the reaction being performed and the desired results, but none-the-less, can generally be made by a person skilled in the art once all relevant information is known.

The term "subject" as used herein includes all members of the animal kingdom including mammals, and suitably refers to humans.

The term "counteranion" as used herein refers to a negatively charged species consisting of a single element, or a negatively charged species consisting of a group of elements connected by ionic and/or covalent bonds.

The term "pharmaceutically acceptable" means compatible with use in subjects, for example, mammals such as humans.

The term "alkyl" as used herein, whether it is used alone or as part of another group, means straight or branched chain, saturated alkyl groups. The number of carbon atoms that are possible in the referenced alkyl group are indicated by the numerical prefix "$C_{n1-n2}$". For example, the term $C_{1-6}$alkyl means an alkyl group having 1, 2, 3, 4, 5 or 6 carbon atoms.

The term "alkylene" as used herein, whether it is used alone or as part of another group, means straight or branched chain, saturated alkylene group, that is, a saturated carbon chain that contains substituents on two of its ends. The number of carbon atoms that are possible in the referenced alkylene group are indicated by the numerical prefix "$C_{n1-n2}$". For example, the term $C_{1-3}$alkylene means an alkylene group having 1, 2 or 3 carbon atoms.

The term "aryl" as used herein, whether it is used alone or as part of another group, refers to cyclic groups that contain at least one aromatic ring. In an embodiment of the application, the aryl group contains from 6, 9, 10 or 14 atoms, such as phenyl, naphthyl, indanyl or anthracenyl.

The term "halo" as used herein, whether it is used alone or as part of another group, refers to a halogen atom and includes Cl, Br and I.

The term "carbocycle" as used herein refers to an aromatic or non-aromatic ring wherein each atom comprising the ring is a carbon atom.

"Tf" as used herein refers to triflate.

"Mes" as used herein refers to 2,4,6-trimethylphenyl.

"SIMes" as used herein refers to the ligand:

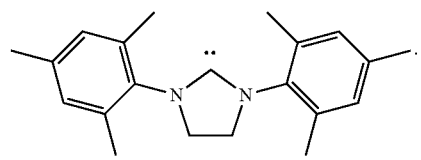

II. Compounds

A synthetic pathway to an azido-functionalized pyridine head-unit is disclosed herein, providing a useful intermediate for the development of bi-functional contrast agents based on such complexes. Functionalization of the contrast agents with a targeting group may, for example, facilitate the passive targeting of tissues. Other functionalities include water-soluble fluorescent probes which may, for example, be used in dual-modality imaging.

Accordingly, the present application includes a compound of Formula I(a) or a hydrate thereof:

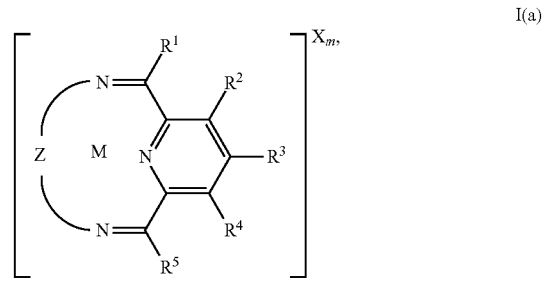

wherein $R^1$ and $R^5$ are each independently $C_{1-6}$alkyl or aryl;

$R^2$ and $R^4$ are each independently H, —OH, halo, $C_{1-6}$alkyl, aryl or $C_{1-3}$alkyleneC(O)OR$^6$, wherein $R^6$ is H or $C_{1-6}$alkyl;

$R^3$ is

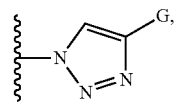

wherein G is a targeting group or a fluorescent probe;

X is a pharmaceutically acceptable counteranion;

Z is —(CR$^7$R$^8$=CR$^9$R$^{10}$-A)$_p$-(CR$^{11}$R$^{12}$=CR$^{13}$R$^{14}$)—;

wherein

A is O or NH;

p is 2, 3 or 4;

⋯⋯ represents a single or double bond;

when ⋯⋯ is a double bond, one of $R^7/R^8$ and $R^9/R^{10}$ or $R^{11}/R^{12}$ and $R^{13}/R^{14}$, as applicable, is not present; and $R^7$ to $R^{14}$ are each independently H, $C_{1-6}$alkyl or aryl; or one of $R^7/R^8$ and $R^9/R^{10}$ and/or $R^{11}/R^{12}$ and $R^{13}/R^{14}$, together with the carbon atoms to which they are attached, form a 5-6 membered carbocycle;

the N and A atoms in the compound of Formula I(a) form an $N_3A_p$ donor set for coordinating with M;

M is selected from $Fe^{3+}$, $Fe^{2+}$, $Co^{2+}$, $Zn^{2+}$, $Mn^{3+}$, $Mn^{2+}$ and $Gd^{3+}$ and is coordinated in an equatorial fashion by at least three atoms of the $N_3A_p$ donor set;

when M is $Fe^{2+}$, $Co^{2+}$, $Zn^{2+}$ or $Mn^{2+}$, m is 2; and when M is $Fe^{3+}$, $Mn^{3+}$ or $Gd^{3+}$, m is 3.

In an embodiment, $R^1$ and $R^5$ are each independently $C_{1-6}$alkyl or phenyl. In another embodiment, $R^1$ and $R^5$ are each independently $C_{1-6}$alkyl. In a further embodiment, $R^1$ and $R^5$ are each independently $C_{1-4}$alkyl. It is an embodiment of the present application that $R^1$ and $R^5$ are each methyl.

In an embodiment, $R^2$ and $R^4$ are each independently H, —OH, Cl, Br, I, $C_{1-4}$alkyl, phenyl or $C_{1-3}$alkyleneC(O)$OR^6$, wherein $R^6$ is H or $C_{1-4}$alkyl. In another embodiment, $R^2$ and $R^4$ are each H. In some embodiments, functional groups such as $C_{1-3}$alkyleneC(O)$OR^6$, wherein $R^6$ is H or $C_{1-6}$alkyl are, for example, used to increase the aqueous solubility of compounds such as the compounds of Formula I(a) of the present application. Accordingly, in another embodiment, $R^2$ and/or $R^4$ is $C_{1-3}$alkyleneC(O)$OR^6$, wherein $R^6$ is H or $C_{1-6}$alkyl. In another embodiment, $R^6$ is H. In a further embodiment, $R^6$ is $C_{1-6}$alkyl. In another embodiment of the present application, $R^6$ is $C_{1-4}$alkyl such as methyl.

G is any suitable targeting group or fluorescent probe, the selection of which can be made by a person skilled in the art.

In an embodiment, G is a targeting group. In another embodiment, the targeting group targets a receptor that is expressed in a tumor cell.

In a further embodiment, the targeting group targets cells having an estrogen receptor. It is an embodiment that the targeting group that targets cells having an estrogen receptor is an estrogen mimic.

For example, it will be appreciated by a person skilled in the art that a contrast agent tagged with an estrogen mimic could selectively image cells with either α-type or β-type estrogen receptors. These receptors are expressed, to different degrees[9], in the female reproductive system (e.g. ovarian and endometrial cells)[10,11]; the male reproductive tract[12]; the brain (hypothalamus)[13]; bone (osteoclasts and osteoblasts)[14]; the heart[15]; and the lungs[16].

In another embodiment, the estrogen mimic targets breast cancer cells. In a further embodiment, the targeting group has the structure:

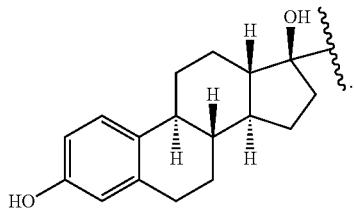

Another receptor which is expressed on the surface of solid tumor cells such as ovarian, kidney, lung, brain, endometrial, colorectal, pancreatic, gastric, prostate, testicular, bladder, head and neck, breast and non-small cell lung cancer is the folate receptor (FR)[17]. Accordingly, in another embodiment, the targeting group targets cells having a folate receptor. In a further embodiment, the targeting group that targets cells having a folate receptor comprises folic acid or a derivative thereof:

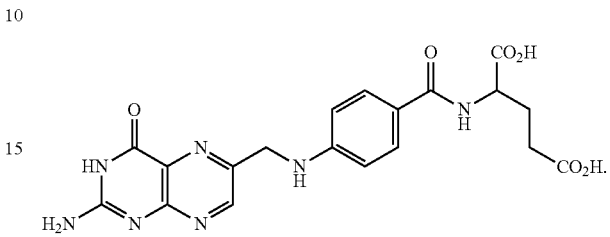

In an embodiment, the folic acid derivative has the structure:

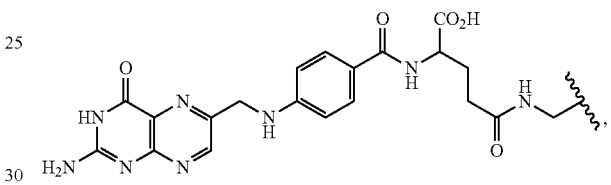

and is prepared from propargyl folate. Propargyl folate is available starting from folate using methods known in the art[18].

In an alternative embodiment, G is a fluorescent probe. In another embodiment, G is a fluorescent probe comprising a non-toxic, water-soluble fluorophore selected from the following classes: endogenous fluorophores, polycyclic aromatics, coumarins, quinolines, indoles, imidizoles, 4-nitrobenz-2-oxa-1,3-diazole (NBD) and related benzoxadiazole compounds, other UV-excited small heterocyclic molecule fluorophores (e.g. bimane and diaryloxazole-containing structures), fluorescein, rhodamines, naphthoxanthene dyes, phenanthridines, boron difluoride dipyrromethene (BODIPY)-based dyes, cyanines, phthalocyanines and oxazines. The selection of a suitable non-toxic, water-soluble fluorophore can be made by a person skilled in the art. For example, Lavis and Raines[19] have reviewed small-molecular fluorescent probes. In some embodiments, a diketopyrrole-based dye[20] is used in the compounds of Formula I(a).

In an embodiment, the fluorescent probe has the structure:

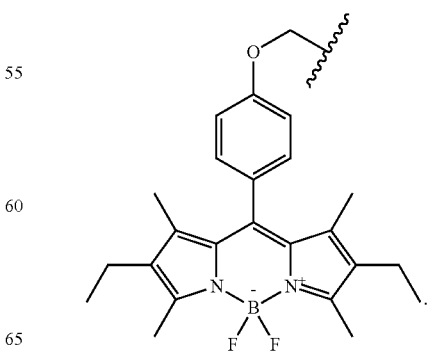

X is any suitable pharmaceutically acceptable counteranion, the selection of which can be made by a person skilled in the art. For example, it will be appreciated by a person skilled in the art that Schiff-base macrocycles can be templated around, for example anions such as bromide, iodide, triflate, perchlorate, thiocyanate and nitrate salts of metals ions. However, such salts may, for example, be toxic, have long excretion time and/or mimic biologically essential metal ions therefore may not be useful, for example, in a method for enhancing contrast in a magnetic resonance image of a subject. While bio-compatible counteranions such as bicarbonate, carbonate and phosphate are not useful in the templation process typically used to prepare Schiff-base macrocycles such as those of the compound of Formula I(a) of the present disclosure, such counteranions may be incorporated via anion exchange.

Accordingly, in an embodiment, the pharmaceutically acceptable counteranion is selected from $Cl^-$, $HCO_3^-$, $CO_3^{2-}$, $H_2PO_4^-$, $HPO_4^{2-}$ and $PO_4^{3-}$. In another embodiment, the pharmaceutically acceptable counteranion is $Cl^-$.

In an embodiment, A is O. In another embodiment, A is NH.

In an embodiment, p is 2 or 3. In another embodiment, p is 2. In a further embodiment, p is 3. It is an embodiment that p is 4.

In an embodiment, $R^7$ to $R^{14}$ are each independently H, $C_{1-4}$alkyl or phenyl. In another embodiment, $R^7$ to $R^{14}$ are each independently H or phenyl. In a further embodiment, $R^7$ to $R^{14}$ are each H. In another embodiment, one of $R^7/R^8$ and $R^9/R^{10}$ and/or $R^{11}/R^{12}$ and $R^{13}/R^{14}$, together with the carbon atoms to which they are attached, form a phenyl.

In an embodiment, Z is selected from —(CH$_2$CH$_2$NH)$_2$—(CH$_2$CH$_2$)—, —(CH$_2$CH$_2$O)$_2$—(CH$_2$CH$_2$)—,

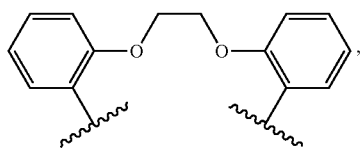

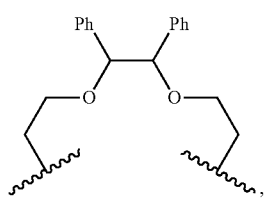

—(CH$_2$CH$_2$O)$_3$—(CH$_2$CH$_2$)— and

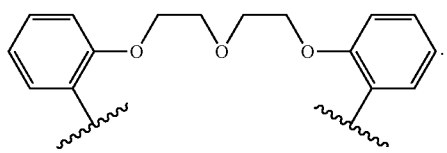 [SMILES: *c1ccccc1OCCOCCOc1ccccc1*]

In another embodiment, Z is selected from —(CH$_2$CH$_2$NH)$_2$—(CH$_2$CH$_2$)—, —(CH$_2$CH$_2$O)$_2$—(CH$_2$CH$_2$)—,

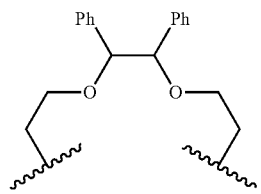 [SMILES: *CCOC(c1ccccc1)C(OCC*)c1ccccc1]

and

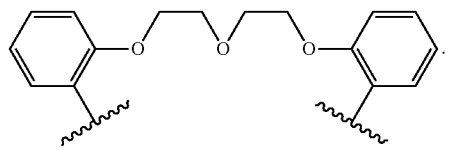 [SMILES: *c1ccccc1OCCOCCOc1ccccc1*]

In a further embodiment, Z is —(CH$_2$CH$_2$NH)$_2$—(CH$_2$CH$_2$)— or —(CH$_2$CH$_2$O)$_2$—(CH$_2$CH$_2$)—.

In an embodiment, M is $Mn^{2+}$ or $Gd^{3+}$, when M is $Mn^{2+}$, m is 2 and when M is $Gd^{3+}$, m is 3. In another embodiment of the present application, M is $Mn^{2+}$ and m is 2. In a further embodiment, M is $Gd^{3+}$ and m is 3.

In an embodiment, the compound of Formula I(a) is a compound of Formula I(a)(i) or a hydrate thereof:

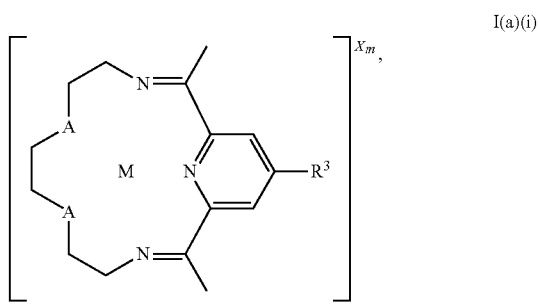

I(a)(i)

wherein
$R^3$ is

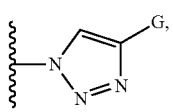

wherein G is a targeting group or a fluorescent probe;
X is a pharmaceutically acceptable counteranion;
A is O or NH;
the N and A atoms in the compound of Formula I(a)(i) form an $N_3A_p$ donor set for coordinating with M;
M is selected from $Fe^{3+}$, $Fe^{2+}$, $Co^{2+}$, $Zn^{2+}$, $Mn^{3+}$, $Mn^{2+}$ and $Gd^{3+}$ and is coordinated in an equatorial fashion by at least three atoms of the $N_3A_p$ donor set;
when M is $Fe^{2+}$, $Co^{2+}$, $Zn^{2+}$ or $Mn^{2+}$, m is 2; and
when M is $Fe^{3+}$, $Mn^{3+}$ or $Gd^{3+}$, m is 3.

It will be appreciated by a person skilled in the art that embodiments of the compounds of Formula I(a)(i) of the present application can be varied as for the compounds of Formula I(a) of the present application.

III. Methods of Preparation and Intermediates

A synthetic pathway to an azido-functionalized pyridine head-unit is disclosed herein, providing a useful intermediate for the development of bi-functional contrast agents. The methods of preparing such bi-functional contrast agents comprise the use of copper catalyzed azide-alkyne cycloaddition (CuAAC), followed by macrocyclization to give a bi-functional contrast agent. Alternatively, following the formation of an azide-functionalized macrocycle, the CuAAC reaction is performed to give the bi-functional contrast agent.

Accordingly, the present application includes a method of preparing a compound of Formula I(a):

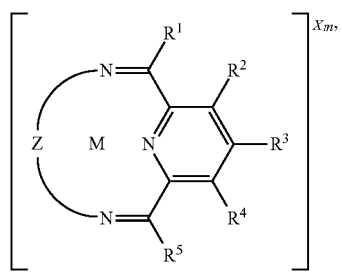

(I(a))

wherein
R$^1$ and R$^5$ are each independently C$_{1-6}$alkyl or aryl;
R$^2$ and R$^4$ are each independently H, —OH, halo, C$_{1-6}$alkyl, aryl or C$_{1-3}$alkyleneC(O)OR$^6$, wherein R$^6$ is H or C$_{1-6}$alkyl;
R$^3$ is

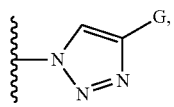

wherein G is a targeting group or a fluorescent probe;
X is a pharmaceutically acceptable counteranion;
Z is —(CR$^7$R$^8$=CR$^9$R$^{10}$-A)$_p$-(CR$^{11}$R$^{12}$=R$^{13}$R$^{14}$)—;
wherein
A is O or NH;
===== p is 2, 3 or 4;
===== represents a single or double bond;
when ===== is a double bond, one of R$^7$/R$^8$ and R$^9$/R$^{10}$ or R$^{11}$/R$^{12}$ and R$^{13}$/R$^{14}$, as applicable, is not present; and
R$^7$ to R$^{14}$ are each independently H, C$_{1-6}$alkyl or aryl; or one of R$^7$/R$^8$ and R$^9$/R$^{10}$ and/or R$^{11}$/R$^{12}$ and R$^{13}$/R$^{14}$, together with the carbon atoms to which they are attached, form a 5-6 membered carbocycle;
the N and A atoms in the compound of Formula I(a) form an N$_3$A$_p$ donor set for coordinating with M;
M is selected from Fe$^{3+}$, Fe$^{2+}$, Co$^{2+}$, Zn$^{2+}$, Mn$^{3+}$, Mn$^{2+}$ and Gd$^{3+}$ and is coordinated in an equatorial fashion by at least three atoms of the N$_3$A$_p$ donor set;
when M is Fe$^{2+}$, Co$^{2+}$, Zn$^{2+}$ or Mn$^{2+}$, m is 2; and
when M is Fe$^{3+}$, Mn$^{3+}$ or Gd$^{3+}$, m is 3, the method comprising:
(a) reacting an azide of Formula II:

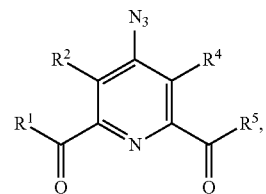

(II)

wherein
R$^1$ and R$^5$ are each independently C$_{1-6}$alkyl or aryl; and
R$^2$ and R$^4$ are each independently H, —OH, halo, C$_{1-6}$alkyl, aryl or C$_{1-3}$alkyleneC(O)OR$^6$, wherein R$^6$ is H or C$_{1-6}$alkyl,
with an alkyne of Formula III:

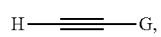

(III)

wherein G is a targeting group or a fluorescent probe, in the presence of a copper catalyst to obtain a compound of Formula IV:

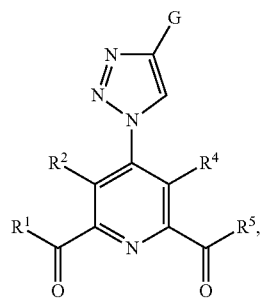

(IV)

wherein
R$^1$ and R$^5$ are each independently C$_{1-6}$alkyl or aryl;
R$^2$ and R$^4$ are each independently H, —OH, halo, C$_{1-6}$alkyl, aryl or C$_{1-3}$alkyleneC(O)OR$^6$, wherein R$^6$ is H or C$_{1-6}$alkyl; and
G is a targeting group or a fluorescent probe, and
(b) reacting the compound of Formula IV with a compound of Formula V:

(V), wherein
X is a pharmaceutically acceptable counteranion;
M is selected from Fe$^{3+}$, Fe$^{2+}$, Co$^{2+}$, Zn$^{2+}$, Mn$^{3+}$, Mn$^{2+}$ and Gd$^{3+}$;
when M is Fe$^{2+}$, Co$^{2+}$, Zn$^{2+}$ or Mn$^{2+}$, m is 2; and
when M is Fe$^{3+}$, Mn$^{3+}$ or Gd$^{3+}$, m is 3,
and a diamine of Formula VI:

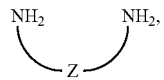

(VI)

wherein
Z is —(CR$^7$R$^8$ ═══ CR$^9$R$^{10}$-A)$_p$-(CR$^{11}$R$^{12}$ ═══ CR$^{13}$R$^{14}$)—;
wherein
A is O or NH;
p is 2, 3 or 4;
═══ represents a single or double bond;
when ═══ is a double bond, one of R$^7$/R$^8$ and R$^9$/R$^{10}$ or R$^{11}$/R$^{12}$ and R$^{13}$/R$^{14}$, as applicable, is not present; and
R$^7$ to R$^{14}$ are each independently H, C$_{1-6}$alkyl or aryl; or
one of R$^7$/R$^8$ and R$^9$/R$^{10}$ and/or R$^{11}$/R$^{12}$ and R$^{13}$/R$^{14}$, together with the
carbon atoms to which they are attached, form a 5-6 membered carbocycle, under conditions to obtain the compound of Formula I(a).

The present application also includes an alternative method of preparing a compound of Formula I(a):

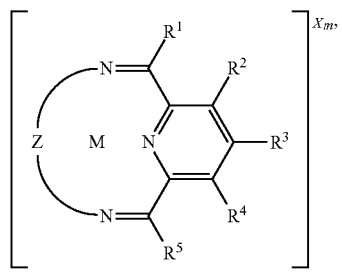

(I(a))

wherein
R$^1$ and R$^5$ are each independently C$_{1-6}$alkyl or aryl;
R$^2$ and R$^4$ are each independently H, —OH, halo, C$_{1-6}$alkyl, aryl or C$_{1-3}$alkyleneC(O)OR$^6$, wherein R$^6$ is H or C$_{1-6}$alkyl;
R$^3$ is

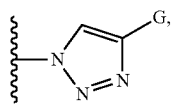

wherein G is a targeting group or a fluorescent probe;
X is a pharmaceutically acceptable counteranion;
Z is —(CR$^7$R$^8$ ═══ CR$^9$R$^{10}$-A)$_p$-(CR$^{11}$R$^{12}$ ═══ CR$^{13}$R$^{14}$)—;
wherein
A is O or NH;
p is 2, 3 or 4;
═══ represents a single or double bond;
when ═══ is a double bond, one of R$^7$/R$^8$ and R$^9$/R$^{10}$ or R$^{11}$/R$^{12}$ and R$^{13}$/R$^{14}$, as applicable, is not present; and
R$^7$ to R$^{14}$ are each independently H, C$_{1-6}$alkyl or aryl; or
one of R$^7$/R$^8$ and R$^9$/R$^{10}$ and/or R$^1$/R$^{12}$ and R$^{13}$/R$^{14}$, together with the carbon atoms to which they are attached, form a 5-6 membered carbocycle;
the N and A atoms in the compound of Formula I(a) form an N$_3$A$_p$ donor set for coordinating with M;
M is selected from Fe$^{3+}$, Fe$^{2+}$, Co$^{2+}$, Zn$^{2+}$, Mn$^{3+}$, Mn$^{2+}$ and Gd$^{3+}$ and is coordinated in an equatorial fashion by at least three atoms of the N$_3$A$_p$ donor set;
when M is Fe$^{2+}$, Co$^{2+}$, Zn$^{2+}$ or Mn$^{2+}$, m is 2; and
when M is Fe$^{3+}$, Mn$^{3+}$ or Gd$^{3+}$, m is 3, the method comprising:
(a) reacting an azide of Formula II:

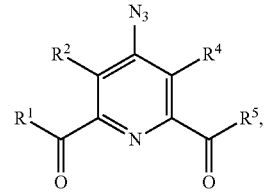

(II)

wherein
R$^1$ and R$^5$ are each independently C$_{1-6}$alkyl or aryl; and
R$^2$ and R$^4$ are each independently H, —OH, halo, C$_{1-6}$alkyl, aryl or C$_{1-3}$alkyleneC(O)OR$^6$, wherein R$^6$ is H or C$_{1-6}$alkyl,
with a compound of Formula V:

MX$_m$ (V), wherein
X is a pharmaceutically acceptable counteranion;
M is selected from Fe$^{3+}$, Fe$^{2+}$, Co$^{2+}$, Zn$^{2+}$, Mn$^{3+}$, Mn$^{2+}$ and Gd$^{3+}$;
when M is Fe$^{2+}$, Co$^{2+}$, Zn$^{2+}$ or Mn$^{2+}$, m is 2; and
when M is Fe$^{3+}$, Mn$^{3+}$ or Gd$^{3+}$, m is 3,
and a diamine of Formula VI:

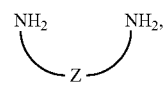

(VI)

wherein
Z is —(CR$^7$R$^8$ ═══ CR$^9$R$^{10}$-A)$_p$-(CR$^{11}$R$^{12}$ ═══ CR$^{13}$R$^{14}$)—;
wherein
A is O or NH;
p is 2, 3 or 4;
═══ represents a single or double bond;
when ═══ is a double bond, one of R$^7$/R$^8$ and R$^9$/R$^{10}$ or R$^{11}$/R$^{12}$ and R$^{13}$/R$^{14}$, as applicable, is not present; and
R$^7$ to R$^{14}$ are each independently H, C$_{1-6}$alkyl or aryl; or
one of R$^7$/R$^8$ and R$^9$/R$^{10}$ and/or R$^{11}$/R$^{12}$ and R$^{13}$/R$^{14}$, together with the carbon atoms to which they are attached, form a 5-6 membered carbocycle,
under conditions to obtain a compound of Formula I(c):

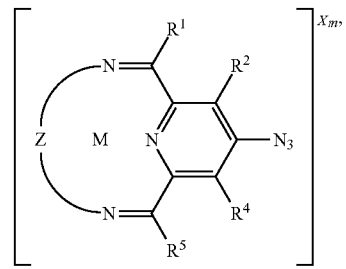

(I(c))

wherein
R$^1$ and R$^5$ are each independently C$_{1-6}$alkyl or aryl;
R$^2$ and R$^4$ are each independently H, —OH, halo, C$_{1-6}$alkyl, aryl or C$_{1-3}$alkyleneC(O)OR$^6$, wherein R$^6$ is H or C$_{1-6}$alkyl;

X is a pharmaceutically acceptable counteranion;

Z is —(CR$^7$R$^8$====CR$^9$R$^{10}$-A)$_p$-(CR$^{11}$R$^{12}$====CR$^{13}$R$^{14}$)—;

wherein

A is O or NH;

p is 2, 3 or 4;

==== represents a single or double bond;

when ==== is a double bond, one of R$^7$/R$^8$ and R$^9$/R$^{10}$ or R$^{11}$/R$^{12}$ and R$^{13}$/R$^{14}$, as applicable, is not present; and R$^7$ to R$^{14}$ are each independently H, C$_{1-6}$alkyl or aryl; or one of R$^7$/R$^8$ and R$^9$/R$^{10}$ and/or R$^{11}$/R$^{12}$ and R$^{13}$/R$^{14}$, together with the carbon atoms to which they are attached, form a 5-6 membered carbocycle;

the N and A atoms in the compound of Formula I(c) form an N$_3$A$_p$ donor set for coordinating with M;

M is selected from Fe$^{3+}$, Fe$^{2+}$, Co$^{2+}$, Zn$^{2+}$, Mn$^{3+}$, Mn$^{2+}$ and Gd$^{3+}$ and is coordinated in an equatorial fashion by at least three atoms of the N$_3$A$_p$ donor set;

when M is Fe$^{2+}$, Co$^{2+}$, Zn$^{2+}$ or Mn$^{2+}$, m is 2; and when M is Fe$^{3+}$, Mn$^{3+}$ or Gd$^{3+}$, m is 3; and (b) reacting the compound of Formula I(c) with an alkyne of Formula III:

(III)

wherein G is a targeting group or a fluorescent probe, in the presence of a copper catalyst to obtain the compound of Formula I(a).

It will be appreciated by a person skilled in the art that the variables R$^1$ to R$^{14}$, X, Z, A, p, M and m in the compounds of the methods of preparing a compound of Formula I(a) of the present application can be varied as for the embodiments of the compounds of Formula I(a) of the present application.

The conditions to obtain the compound of Formula IV from the reaction of the azide of Formula II with the alkyne of Formula III in the presence of a copper catalyst or, alternatively, the compound of Formula I(a) from the reaction of the compound of Formula I(c) with the alkyne of Formula III in the presence of a copper catalyst, as applicable, can be any suitable conditions. Such conditions can be selected by the person skilled in the art. For example, it will be appreciated by a person skilled in the art that because azides are known to be explosive, the reaction is typically performed under mild conditions, for example from about 30° C. to about 50° C. The selection of solvent will depend, for example, on the solubility of the applicable azide and/or the alkyne of Formula III. The selection of a suitable solvent can be made by a person skilled in the art. For example, a "click reaction" typically employs a solvent that is benign and easily removed. In an embodiment, the solvent is selected from methanol, t-butanol, acetone, dimethylformamide (DMF), dioxane, water, dimethyl sulfoxide (DMSO) and combinations thereof. In another embodiment, the solvent is selected from methanol, t-butanol, acetone and dimethylformamide (DMF).

The copper catalyst is any suitable copper catalyst, the selection of which can be made by a person skilled in the art. In an embodiment, the copper catalyst comprises CuSO$_4$ and a reducing agent such as ascorbic acid to reduce the Cu$^{II}$ in situ; a Cu$^I$ salt such as CuCl, CuBr, CuI or Cu(acetate); a Cu$^I$ coordination complex such as [Cu(CH$_3$CN)$_4$]Q, wherein Q is PF$_6^-$ or $^-$OTf; Cu$^I$ tris(triazolyl)methyl amines such as [Cu$^I$(L$^A$)], wherein L$^A$ is

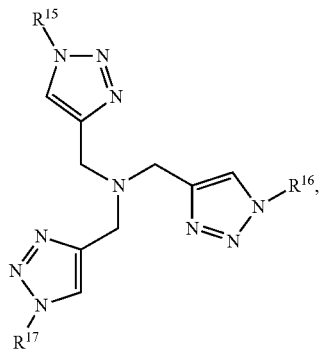

wherein R$^{15}$ to R$^{17}$ are each benzyl, tert-butyl, —(CH$_2$)$_3$OH or —(CH$_2$)$_2$COOH; Cu$^I$ tris(benzimidazolyl)methyl amines such as [Cu$^I$(L$^B$)], wherein L$^B$ is

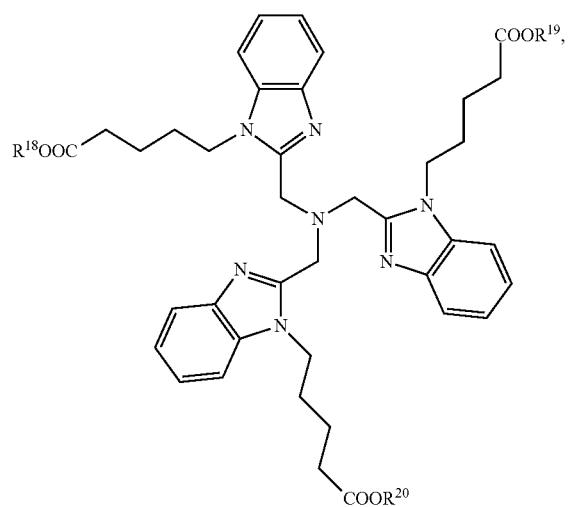

wherein R$^{18}$ to R$^{20}$ are each H or ethyl; Cu$^I$ N-heterocyclic carbenes such as [CuBr(SIMes)], [CuCl(phenanthroline)(SIMes)] and [CuCl(SIMes)(4,7-dichloro-1,10-phenanthroline)]; and Cu$^I$ 1,2,3-triazol-5-ylidines such as [Cu$^I$Cl(L$^C$)], wherein L$^C$ is

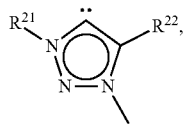

wherein R$^{21}$ and R$^{22}$ are each phenyl or Mes. Such catalysts can, for example, be prepared and/or used following literature procedures.[21]

The conditions to obtain the compound of Formula I(a) from the reaction of the compound of Formula IV with the compound of Formula V and the diamine of Formula VI can be any suitable conditions.

For example, the compound of Formula IV (e.g. about 1 equivalent) is added to a solution of the compound of Formula V (e.g. about 1 equivalent) in a suitable solvent (e.g. methanol) and the mixture heated to a suitable temperature, for example, about 30° C. to about 70° C. or about 50° C., the diamine of Formula VI (e.g. about 1 equivalent)

is added, then the resultant mixture heated to a temperature of about 75° C. to about 95° C. or about 85° C. and refluxed for a suitable time, for example about 4 hours to about 18 hours.

The conditions to obtain the compound of Formula I(c) from the reaction of the compound of Formula II with the compound of Formula V and the diamine of Formula VI can be any suitable conditions.

For example, the compound of Formula II (e.g. about 1 equivalent) is added to a solution of the compound of Formula V (e.g. about 1 equivalent) in a suitable solvent (e.g. methanol) and the mixture heated to a suitable temperature, for example about 30° C. to about 50° C. or about 40° C., the diamine of Formula VI (e.g. about 1 equivalent) is added, then the resultant mixture heated to a temperature of about 70° C. to about 80° C. or about 75° C. and refluxed for a suitable time, for example about 4 hours to about 18 hours.

The compounds of Formula II which are used in the methods of preparing the compound of Formula I(a) of the present application are new. Accordingly, the present application also includes a compound of Formula II:

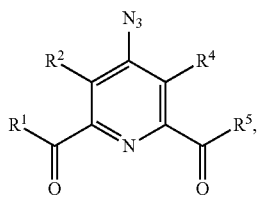

(II)

wherein
$R^1$ and $R^5$ are each independently $C_{1-6}$alkyl or aryl; and
$R^2$ and $R^4$ are each independently H, —OH, halo, $C_{1-6}$alkyl, aryl or $C_{1-3}$alkyleneC(O)OR$^6$, wherein $R^6$ is H or $C_{1-6}$alkyl.

It will be appreciated by a person skilled in the art that the variables $R^1$, $R^2$, $R^4$, $R^5$ and $R^6$ in the compounds of Formula II of the present application can be varied as for the embodiments of the compounds of Formula I(a) of the present application.

Compounds of Formula II of the present application are available from the corresponding di-acids[29-32] or di-acid chlorides[31,32] using methods known in the art, for example as shown in Scheme 5 hereinbelow.

The compounds of Formula IV which are used in the methods of preparing the compound of Formula I(a) of the present application are new. Accordingly, the present application also includes a compound of Formula IV:

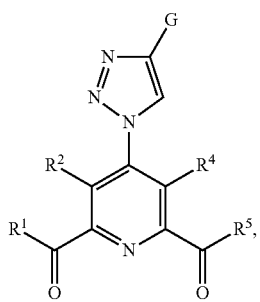

(IV)

wherein
$R^1$ and $R^5$ are each independently $C_{1-6}$alkyl or aryl;
$R^2$ and $R^4$ are each independently H, —OH, halo, $C_{1-6}$alkyl, aryl or $C_{1-3}$alkyleneC(O)OR$^6$, wherein $R^6$ is H or $C_{1-6}$alkyl; and G is a targeting group or a fluorescent probe.

It will be appreciated by a person skilled in the art that the variables $R^1$, $R^2$, $R^4$, $R^5$, $R^6$ and G in the compounds of Formula IV of the present application can be varied as for the embodiments of the compounds of Formula I(a) of the present application.

IV. Methods of Enhancing Contrast and Uses

The Mn$^{II}$- and Gd$^{III}$-based Schiff-base macrocyclic complexes disclosed herein have been shown to be useful as potential contrast agents. The compounds display high relaxivity values, and have useful stability in solution due to the bis-imine character of the macrocyclic ligands. Toxicity and imaging studies on three of the prepared complexes show that these agents exhibit low biotoxicity and good imaging potential.

Accordingly, the present application includes a method of enhancing contrast in a magnetic resonance image of a subject, the method comprising:
(a) administering to the subject, a compound of Formula I(b) or a hydrate thereof:

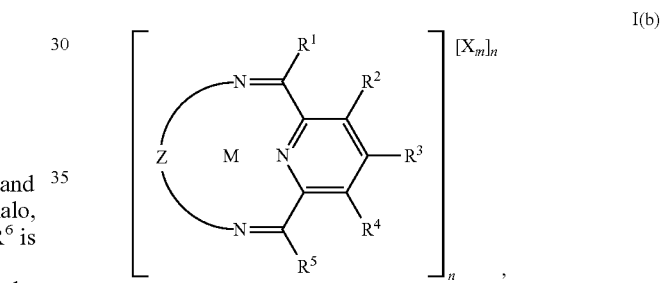

I(b)

wherein
$R^1$ and $R^5$ are each independently $C_{1-6}$alkyl or aryl;
$R^2$ and $R^4$ are each independently H, —OH, halo, $C_{1-6}$alkyl, aryl or $C_{1-3}$alkyleneC(O)OR$^6$, wherein $R^6$ is H or $C_{1-6}$alkyl;
n is 1 or 2;
when n is 1, $R^3$ is H, —OH, halo, $C_{1-6}$alkyl, aryl or $C_{1-3}$alkyleneC(O)OR$^6$, wherein $R^6$ is H or $C_{1-6}$alkyl;
when n is 2, $R^3$ represents a single bond;
X is a pharmaceutically acceptable counteranion;
Z is —(CR$^7$R$^8$﹌CR$^9$R$^{10}$-A)$_p$-(CR$^{11}$R$^{12}$﹌CR$^{13}$R$^{14}$)—;
wherein
A is O;
﹌ p is 2, 3 or 4;
﹌ represents a single or double bond;
when ﹌ is a double bond, one of R$^7$/R$^8$ and R$^9$/R$^{10}$ or R$^{11}$/R$^{12}$ and R$^{13}$/R$^{14}$, as applicable, is not present; and
$R^7$ to $R^{14}$ are each independently H, $C_{1-6}$alkyl or aryl; or
one of R$^7$/R$^8$ and R$^9$/R$^{10}$ and/or R$^{11}$/R$^{12}$ and R$^{13}$/R$^{14}$, together with the carbon atoms to which they are attached, form a 5-6 membered carbocycle;
the N and A atoms in the compound of Formula I(b) form an $N_3A_p$ donor set for coordinating with M;
M is selected from $Fe^{3+}$, $Fe^{2+}$, $Co^{2+}$, $Zn^{2+}$, $Mn^{3+}$, $Mn^{2+}$ and $Gd^{3+}$ and is coordinated in an equatorial fashion by at least three atoms of the $N_3A_p$ donor set;

when M is $Fe^{2+}$, $Co^{2+}$, $Zn^{2+}$ or $Mn^{2+}$, m is 2; and
when M is $Fe^{3+}$, $Mn^{3+}$ or $Gd^{3+}$, m is 3; and
(b) obtaining a magnetic resonance image of the subject.

In an embodiment, $R^1$ and $R^5$ are each independently $C_{1-6}$alkyl or phenyl. In another embodiment, $R^1$ and $R^5$ are each independently $C_{1-6}$alkyl. In a further embodiment, $R^1$ and $R^5$ are each independently $C_{1-4}$alkyl. It is an embodiment of the present application that $R^1$ and $R^5$ are each methyl.

In an embodiment, $R^2$ and $R^4$ are each independently H, —OH, Cl, Br, I, $C_{1-4}$alkyl, phenyl or $C_{1-3}$alkyleneC(O)$OR^6$, wherein $R^6$ is H or $C_{1-4}$alkyl. In another embodiment, $R^2$ and $R^4$ are each H. In some embodiments, functional groups such as $C_{1-3}$alkyleneC(O)$OR^6$, wherein $R^6$ is H or $C_{1-6}$alkyl are, for example, used to increase the aqueous solubility of compounds such as the compounds of Formula I(b) of the present application. Accordingly, in another embodiment, $R^2$ and/or $R^4$ is $C_{1-3}$alkyleneC(O)$OR^6$, wherein $R^6$ is H or $C_{1-6}$alkyl. In another embodiment, $R^6$ is H. In a further embodiment, $R^6$ is $C_{1-6}$alkyl. In another embodiment of the present application, $R^6$ is $C_{1-4}$alkyl such as methyl.

In an embodiment, n is 1 and $R^3$ is H, —OH, halo, $C_{1-6}$alkyl, aryl or $C_{1-3}$alkyleneC(O)$OR^6$, wherein $R^6$ is H or $C_{1-6}$alkyl. In another embodiment, $R^3$ is H, —OH, Cl, Br, I, $C_{1-4}$alkyl, phenyl or $C_{1-3}$alkyleneC(O)$OR^6$, wherein $R^6$ is H or $C_{1-4}$alkyl. In another embodiment, $R^3$ is H. In some embodiments, functional groups such as $C_{1-3}$alkyleneC(O)$OR^6$, wherein $R^6$ is H or $C_{1-6}$alkyl are, for example, used to increase the aqueous solubility of compounds such as the compounds of Formula I(b) of the present application. Accordingly, in another embodiment, $R^3$ is $C_{1-3}$alkyleneC(O)$OR^6$, wherein $R^6$ is H or $C_{1-6}$alkyl. In another embodiment, $R^6$ is H. In a further embodiment, $R^6$ is $C_{1-6}$alkyl. In another embodiment of the present application, $R^6$ is $C_{1-4}$alkyl such as methyl.

In another embodiment, $R^2$, $R^3$ and $R^4$ are all H.

In another embodiment, n is 2 and $R^3$ represents a single bond. It will be appreciated by a person skilled in the art that such complexes contain two Schiff-base macrocycles which are joined by a single bond at position $R^3$.

X is any suitable pharmaceutically acceptable counteranion, the selection of which can be made by a person skilled in the art. For example, it will be appreciated by a person skilled in the art that Schiff-base macrocycles can be templated around, for example anions such as bromide, iodide, triflate, perchlorate, thiocyanate and nitrate salts of metals ions. However, such salts may, for example, be toxic, have long excretion time and/or mimic biologically essential metal ions therefore may not be useful, for example, in a method for enhancing contrast in a magnetic resonance image of a subject. While bio-compatible counteranions such as bicarbonate, carbonate and phosphate are not useful in the templation process typically used to prepare Schiff-base macrocycles such as those of the compound of Formula I(b) of the present disclosure, such counteranions may be incorporated via anion exchange.

Accordingly, in an embodiment, the pharmaceutically acceptable counteranion is selected from $Cl^-$, $HCO_3^-$, $CO_3^{2-}$, $H_2PO_4^-$, $HPO_4^{2-}$ and $PO_4^{3-}$. In another embodiment, the pharmaceutically acceptable counteranion is $Cl^-$.

In an embodiment, p is 2 or 3. In another embodiment, p is 2. In a further embodiment, p is 3. It is an embodiment that p is 4.

In an embodiment, $R^7$ to $R^{14}$ are each independently H, $C_{1-4}$alkyl or phenyl. In another embodiment, $R^7$ to $R^{14}$ are each independently H or phenyl. In a further embodiment, $R^7$ to $R^{14}$ are each H. In another embodiment, one of $R^7/R^8$ and $R^9/R^{10}$ and/or $R^{11}/R^{12}$ and $R^{13}/R^{14}$, together with the carbon atoms to which they are attached, form a phenyl.

In an embodiment, Z is selected from —(CH$_2$CH$_2$O)$_2$—(CH$_2$CH$_2$)—,

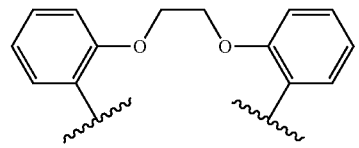

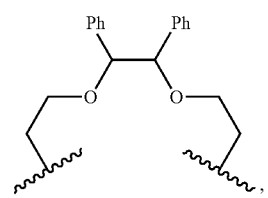

—(CH$_2$CH$_2$O)$_3$—(CH$_2$CH$_2$)— and

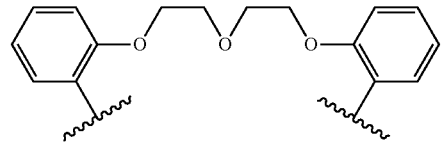

In another embodiment, Z is selected from —(CH$_2$CH$_2$O)$_2$—(CH$_2$CH$_2$)—,

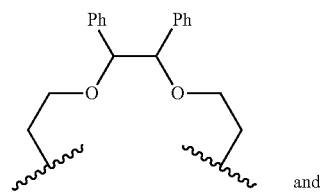

and

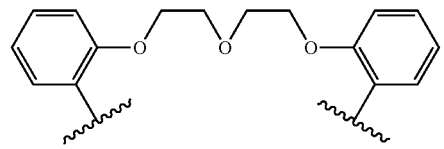

In a further embodiment, Z is —(CH$_2$CH$_2$O)$_2$—(CH$_2$CH$_2$)—.

In an embodiment, M is $Mn^{2+}$ or $Gd^{3+}$, when M is $Mn^{2+}$, m is 2 and when M is $Gd^{3+}$, m is 3. In another embodiment of the present application, M is $Mn^{2+}$ and m is 2. In a further embodiment, M is $Gd^{3+}$ and m is 3.

In an embodiment, the compound of Formula I(b) is selected from:

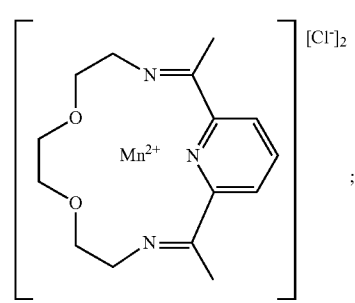
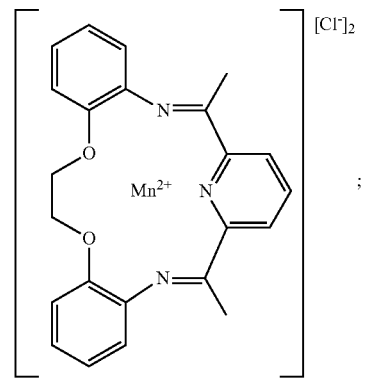
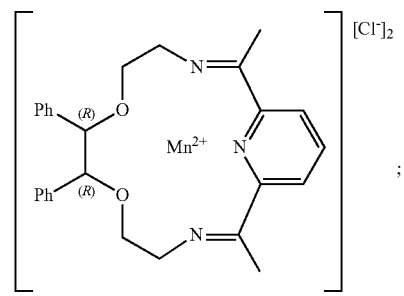
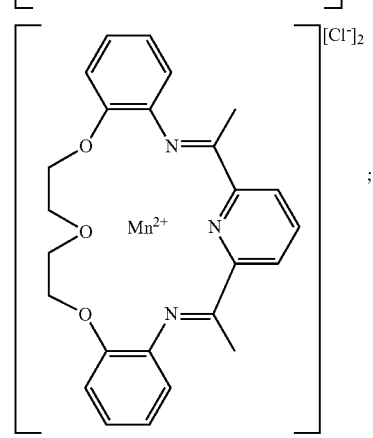
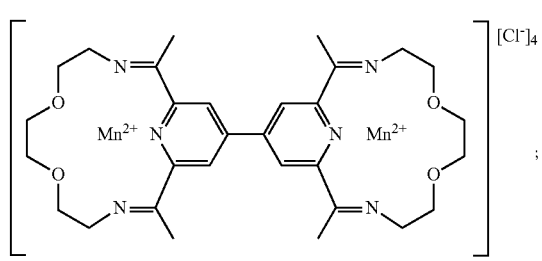
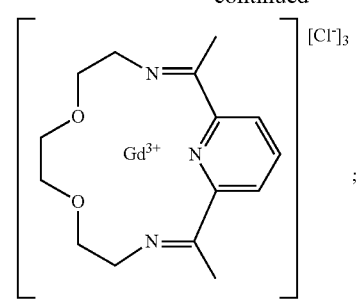
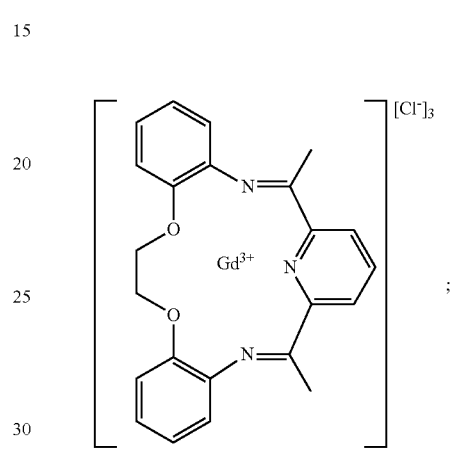
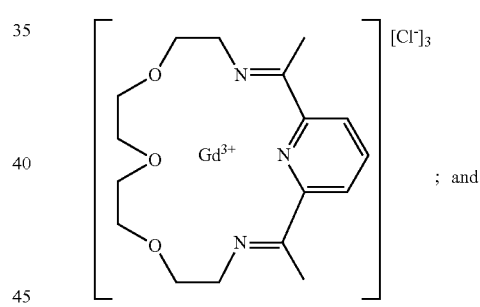
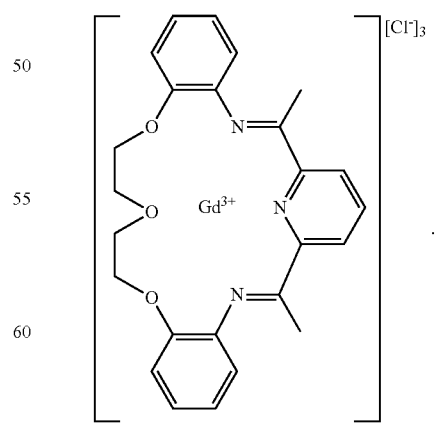
; and
.
In another embodiment of the present application, the compound of Formula I(b) is selected from:

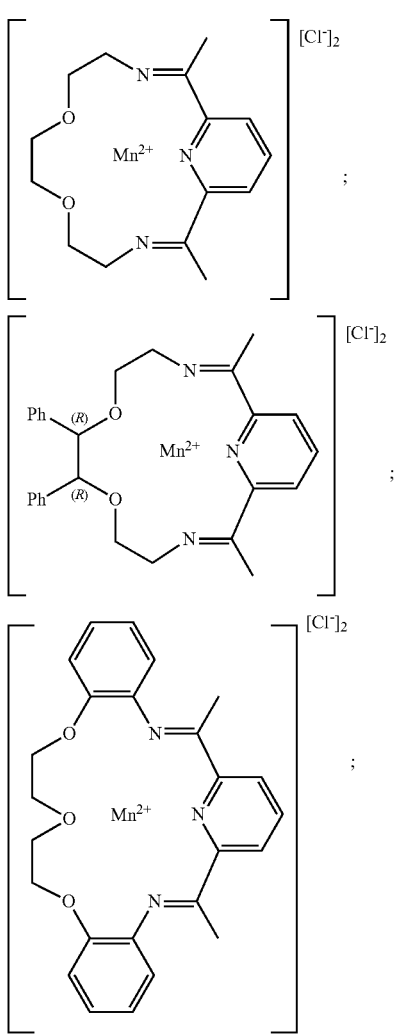
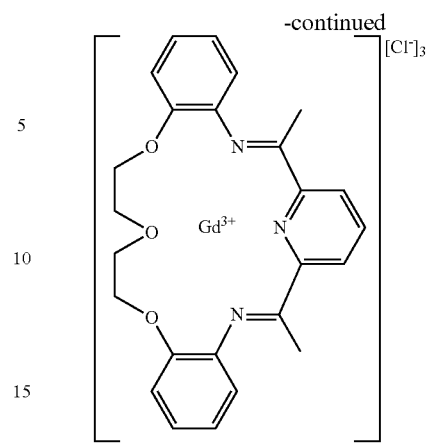
In another embodiment, the compound of Formula I(b) is
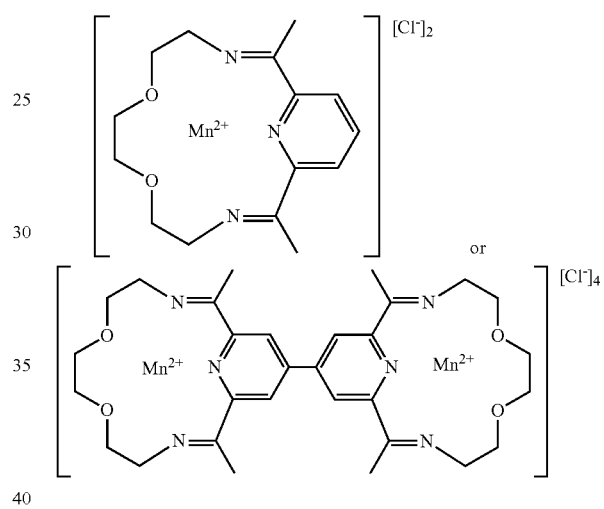
In another embodiment, the compound of Formula I(b) is:
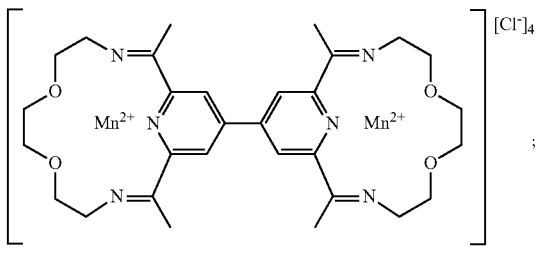
; and
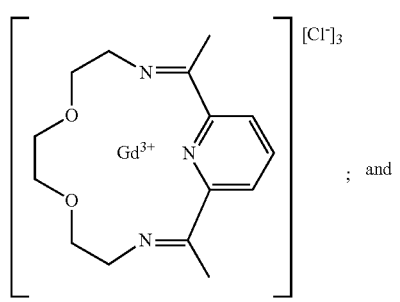
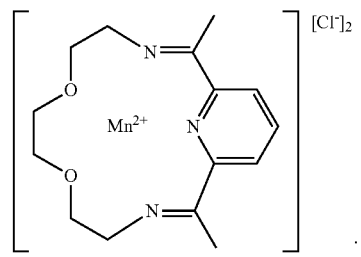
In another embodiment, the compound of Formula I(b) is:
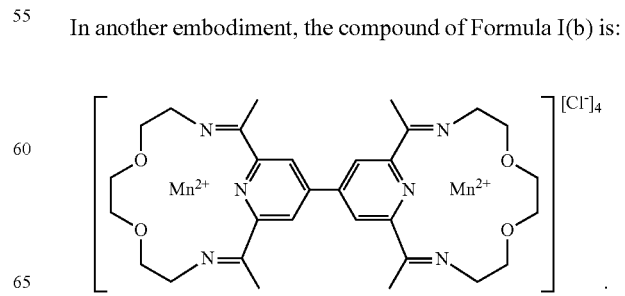

As the compounds of Formula I(b) do not have a specific targeting group, while not being bound by theory, the inventors expect these compounds will act like an extracellular fluid (ECF) agents, which distribute throughout the extracellular fluid post-injection, are useful for imaging most tissues and organs in the body, and are excreted primarily via the kidneys. In the studies of the present disclosure, the bladder and kidneys were enhanced. Accordingly, in an embodiment, the method is a method for enhancing contrast in a magnetic resonance image of a bladder and/or a kidney of a subject.

It will be appreciated by a person skilled in the art that contrast agents are useful to visualize lesions; i.e. to distinguish between regions of healthy and diseased tissue so as to visualize lesions. In vivo studies on animal models with specific cancers and other lesions can determine the potential of the compounds of Formula I(b) for the imaging of given diseases such as cancer.

The present application also includes a method of enhancing contrast in a magnetic resonance image of a subject, the method comprising:

(a) administering to the subject, a compound of Formula I(a) or a hydrate thereof:

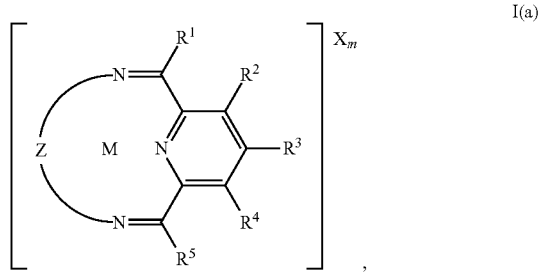

wherein
$R^1$ and $R^5$ are each independently $C_{1-6}$alkyl or aryl;
$R^2$ and $R^4$ are each independently H, —OH, halo, $C_{1-6}$alkyl, aryl or $C_{1-3}$alkyleneC(O)OR$^6$, wherein $R^6$ is H or $C_{1-6}$alkyl;
$R^3$ is

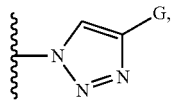

wherein G is a targeting group or a fluorescent probe;
X is a pharmaceutically acceptable counteranion;
Z is —(CR$^7$R$^8$═CR$^9$R$^{10}$-A)$_p$-(CR$^{11}$R$^{12}$═CR$^{13}$R$^{14}$)—;
wherein
A is O or NH;
p is 2, 3 or 4;
═══ represents a single or double bond;
when ═══ is a double bond, one of R$^7$/R$^8$ and R$^9$/R$^{10}$ or R$^{11}$/R$^{12}$ and R$^{13}$/R$^{14}$, as applicable, is not present; and
$R^7$ to $R^{14}$ are each independently H, $C_{1-6}$alkyl or aryl; or one of R$^7$/R$^8$ and R$^9$/R$^{10}$ and/or R$^{11}$/R$^{12}$ and R$^{13}$/R$^{14}$, together with the carbon atoms to which they are attached, form a 5-6 membered carbocycle;
the N and A atoms in the compound of Formula I(a) form an N$_3$A$_p$ donor set for coordinating with M;

M is selected from Fe$^{3+}$, Fe$^{2+}$, Co$^{2+}$, Zn$^{2+}$, Mn$^{3+}$, Mn$^{2+}$ and Gd$^{3+}$ and is coordinated in an equatorial fashion by at least three atoms of the N$_3$A$_p$ donor set;
when M is Fe$^{2+}$, Co$^{2+}$, Zn$^{2+}$ or Mn$^{2+}$, m is 2; and
when M is Fe$^{3+}$, Mn$^{3+}$ or Gd$^{3+}$, m is 3; and
(b) obtaining a magnetic resonance image of the subject.

It will be appreciated by a person skilled in the art that embodiments of the compounds of Formula I(a) in such a method can be varied as for the embodiments of the compounds of Formula I(a) of the present application.

In an embodiment, G is a targeting group and the method comprises obtaining a magnetic resonance image of a site in the subject that the targeting group targets. The targeting group can be any suitable targeting group. In an embodiment, the targeting group targets a receptor that is expressed in a tumor cell and the method comprises obtaining a magnetic resonance image of a tissue in the subject susceptible to such tumor cells.

In a further embodiment, the targeting group targets cells having an estrogen receptor and the method comprises obtaining a magnetic resonance image of a tissue in the subject comprising cells having estrogen receptors. It is an embodiment that the targeting group that targets cells having an estrogen receptor is an estrogen mimic. In another embodiment, the magnetic resonance image is obtained in a site selected from: the female reproductive system (e.g. ovarian and endometrial cells); the male reproductive tract; the brain (hypothalamus); bone (osteoclasts and osteoblasts); the heart; and the lungs.

In another embodiment, the estrogen mimic targets breast cancer cells and the method comprises obtaining a magnetic resonance image of breast tissue in a subject. In another embodiment, the method is used in a method for diagnosing breast cancer. In a further embodiment of the present application, the targeting group has the structure:

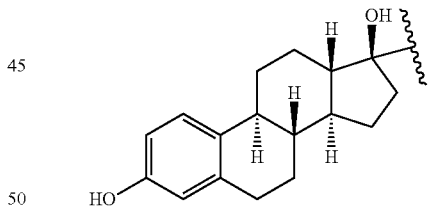

Another receptor which is expressed on the surface of solid tumor cells such as ovarian, kidney, lung, brain, endometrial, colorectal, pancreatic, gastric, prostate, testicular, bladder, head and neck, breast and non-small cell lung cancer is the folate receptor (FR). Accordingly, in another embodiment, the targeting group targets cells having a folate receptor and the method comprises obtaining an MRI image of a site in the subject susceptible to solid tumors comprising folate receptors such as but not limited to an ovary, a kidney, a lung, the brain, the endometrium (uterus), the colon, the rectum, the pancreas, the stomach, the prostate, the testes, the bladder, the head, the neck or a breast.

In a further embodiment, the targeting group that targets cells having a folate receptor comprises folic acid:

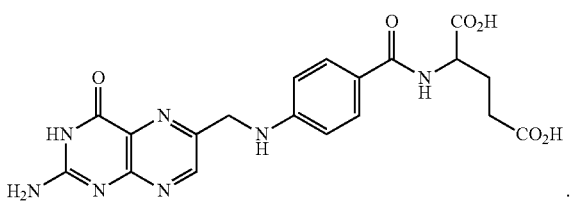 [SMILES: Nc1nc2ncc(CNc3ccc(C(=O)NC(CCC(=O)O)C(=O)O)cc3)nc2c(=O)[nH]1]

In an alternative embodiment, G is a fluorescent probe and the method further comprises obtaining a fluorescence image of the subject. The fluorescent probe can be any suitable fluorescent probe.

In an embodiment, G is a fluorescent probe comprising a non-toxic, water-soluble fluorophore selected from the following classes: endogenous fluorophores, polycyclic aromatics, coumarins, quinolines, indoles, imidizoles, 4-nitrobenz-2-oxa-1,3-diazole (NBD) and related benzoxadiazole compounds, other UV-excited small heterocyclic molecules fluorophores (e.g. bimane and diaryloxazole-containing structures), fluorescein, rhodamines, naphthoxanthene dyes, phenanthridines, boron difluoride dipyrromethene (BODIPY)-based dyes, cyanines, phthalocyanines and oxazines or is a diketopyrrole-based dye. In a further embodiment, the fluorescent probe has the structure:

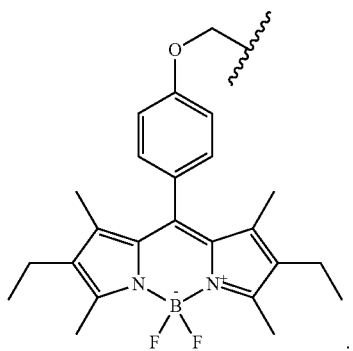

Methods for in vivo dual-imaging are known in the art. In an embodiment, the method comprises collecting magnetic resonance image sequences simultaneously with fluorescence signals. In another embodiment, the magnetic resonance image sequences are collected simultaneously with the fluorescence signals using a magnetic resonance diffuse optical tomography system. In an alternate embodiment, the method comprises collecting magnetic resonance image sequences sequentially with fluorescence signals.

The present application also includes a method of diagnosing cancer in a subject, the method comprising:
(a) administering to the subject, a compound of Formula I(a) or a hydrate thereof:

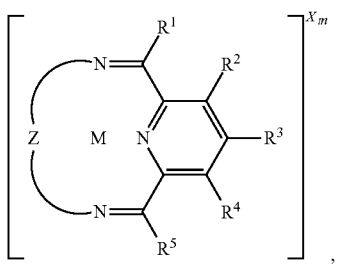

I(a)

wherein
$R^1$ and $R^5$ are each independently $C_{1-6}$alkyl or aryl;
$R^2$ and $R^4$ are each independently H, —OH, halo, $C_{1-6}$alkyl, aryl or $C_{1-3}$alkyleneC(O)OR$^6$, wherein $R^6$ is H or $C_{1-6}$alkyl;
$R^3$ is

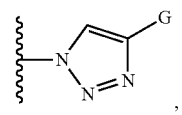

wherein G is a targeting group or a fluorescent probe;
X is a pharmaceutically acceptable counteranion;
Z is —(CR$^7$R$^8$═CR$^9$R$^{10}$-A)$_p$-(CR$^{11}$R$^{12}$═R$^{13}$R$^{14}$)—;
wherein
A is O or NH;
═ p is 2, 3 or 4;
═ represents a single or double bond;
when ═ is a double bond, one of R$^7$/R$^8$ and R$^9$/R$^{10}$ or R$^{11}$/R$^{12}$ and R$^{13}$/R$^{14}$, as applicable, is not present; and
$R^7$ to $R^{14}$ are each independently H, $C_{1-6}$alkyl or aryl; or one of R$^7$/R$^8$ and R$^9$/R$^{10}$ and/or R$^{11}$/R$^{12}$ and R$^{13}$/R$^{14}$, together with the carbon atoms to which they are attached, form a 5-6 membered carbocycle;
the N and A atoms in the compound of Formula I(a) form an N$_3$A$_p$ donor set for coordinating with M;
M is selected from Fe$^{3+}$, Fe$^{2+}$, Co$^{2+}$, Zn$^{2+}$, Mn$^{3+}$, Mn$^{2+}$ and Gd$^{3+}$ and is coordinated in an equatorial fashion by at least three atoms of the N$_3$A$_p$ donor set;
when M is Fe$^{2+}$, Co$^{2+}$, Zn$^{2+}$ or Mn$^{2+}$, m is 2; and
when M is Fe$^{3+}$, Mn$^{3+}$ or Gd$^{3+}$, m is 3;
(b) obtaining a magnetic resonance image of the subject; and
(c) analyzing the magnetic resonance image to determine whether or not the cancer is present in the magnetic resonance image.

The present application also includes a method of diagnosing cancer in a subject, the method comprising:
(a) administering to the subject, a compound of Formula I(b) or a hydrate thereof:

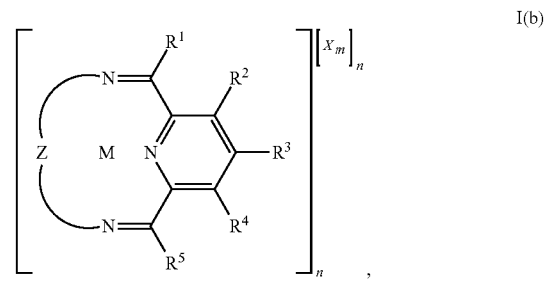

I(b)

wherein
$R^1$ and $R^5$ are each independently $C_{1-6}$alkyl or aryl;
$R^2$ and $R^4$ are each independently H, —OH, halo, $C_{1-6}$alkyl, aryl or $C_{1-3}$alkyleneC(O)OR$^6$, wherein $R^6$ is H or $C_{1-6}$alkyl;
n is 1 or 2;
when n is 1, R$^3$ is H, —OH, halo, $C_{1-6}$alkyl, aryl or $C_{1-3}$alkyleneC(O)OR$^6$, wherein $R^6$ is H or $C_{1-6}$alkyl;
when n is 2, R$^3$ represents a single bond;
X is a pharmaceutically acceptable counteranion;
Z is —(CR$^7$R$^8$═CR$^9$R$^{10}$-A)$_p$-(CR$^{11}$R$^{12}$═CR$^{13}$R$^{14}$)—;

wherein
A is O;
p is 2, 3 or 4;
----- represents a single or double bond;
when ----- is a double bond, one of $R^7/R^8$ and $R^9/R^{10}$ or $R^{11}/R^{12}$ and $R^{13}/R^{14}$, as applicable, is not present; and
$R^7$ to $R^{14}$ are each independently H, $C_{1-6}$alkyl or aryl; or one of $R^7/R^8$ and $R^9/R^{10}$ and/or $R^{11}/R^{12}$ and $R^{13}/R^{14}$, together with the carbon atoms to which they are attached, form a 5-6 membered carbocycle;
the N and A atoms in the compound of Formula I(b) form an $N_3A_p$ donor set for coordinating with M;
M is selected from $Fe^{3+}$, $Fe^{2+}$, $Co^{2+}$, $Zn^{2+}$, $Mn^{3+}$, $Mn^{2+}$ and $Gd^{3+}$ and is coordinated in an equatorial fashion by at least three atoms of the $N_3A_p$ donor set;
when M is $Fe^{2+}$, $Co^{2+}$, $Zn^{2+}$ or $Mn^{2+}$, m is 2; and
when M is $Fe^{3+}$, $Mn^{3+}$ or $Gd^{3+}$, m is 3;
(b) obtaining a magnetic resonance image of the subject; and
(c) analyzing the magnetic resonance image to determine whether or not the cancer is present in the magnetic resonance image.

It will be appreciated by a person skilled in the art that embodiments of such methods of diagnosing cancer in a subject can be varied, as appropriate, as for embodiments of the methods for enhancing contrast in a magnetic resonance image of a subject of the present application.

The present application also includes a use of a compound of Formula I(b) or a hydrate thereof:

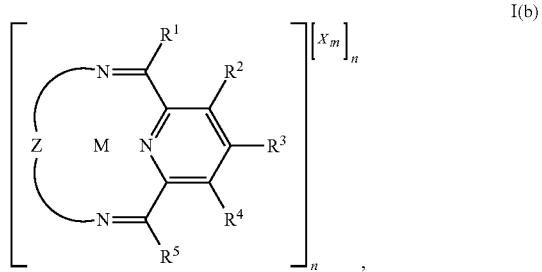

wherein
$R^1$ and $R^5$ are each independently $C_{1-6}$alkyl or aryl;
$R^2$ and $R^4$ are each independently H, —OH, halo, $C_{1-6}$alkyl, aryl or $C_{1-3}$alkyleneC(O)OR$^6$, wherein $R^6$ is H or $C_{1-6}$alkyl;
n is 1 or 2;
when n is 1, $R^3$ is H, —OH, halo, $C_{1-6}$alkyl, aryl or $C_{1-3}$alkyleneC(O)OR$^6$, wherein $R^6$ is H or $C_{1-6}$alkyl;
when n is 2, $R^3$ represents a single bond;
X is a pharmaceutically acceptable counteranion;
Z is —(CR$^7$R$^8$ ----- CR$^9$R$^{10}$-A)$_p$-(CR$^{11}$R$^{12}$ ----- CR$^{13}$R$^{14}$)—;
wherein
A is O;
p is 2, 3 or 4;
----- represents a single or double bond;
when ----- is a double bond, one of $R^7/R^8$ and $R^9/R^{10}$ or $R^{11}/R^{12}$ and $R^{13}/R^{14}$, as applicable, is not present; and
$R^7$ to $R^{14}$ are each independently H, $C_{1-6}$alkyl or aryl; or one of $R^7/R^8$ and $R^9/R^{10}$ and/or $R^{11}/R^{12}$ and $R^{13}/R^{14}$, together with the carbon atoms to which they are attached, form a 5-6 membered carbocycle;
the N and A atoms in the compound of Formula I(b) form an $N_3A_p$ donor set for coordinating with M;
M is selected from $Fe^{3+}$, $Fe^{2+}$, $Co^{2+}$, $Zn^{2+}$, $Mn^{3+}$, $Mn^{2+}$ and $Gd^{3+}$ and is coordinated in an equatorial fashion by at least three atoms of the $N_3A_p$ donor set;
when M is $Fe^{2+}$, $Co^{2+}$, $Zn^{2+}$ or $Mn^{2+}$, m is 2; and
when M is $Fe^{3+}$, $Mn^{3+}$ or $Gd^{3+}$, m is 3,
for enhancing contrast in a magnetic resonance image of a subject. It will be appreciated by a person skilled in the art that embodiments of such uses can be varied as for the embodiments of the methods of enhancing contrast in a magnetic resonance image of a subject comprising administering a compound of Formula I(b) or a hydrate thereof of the present application.

The present application also includes a use of a compound of Formula I(a) or a hydrate thereof:

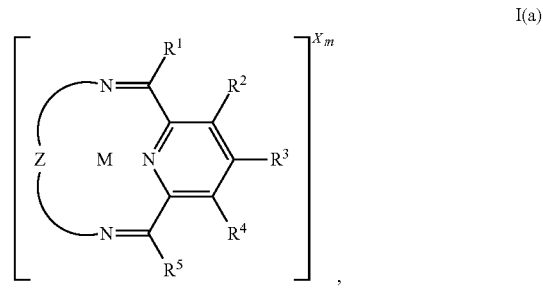

wherein
$R^1$ and $R^5$ are each independently $C_{1-6}$alkyl or aryl;
$R^2$ and $R^4$ are each independently H, —OH, halo, $C_{1-6}$alkyl, aryl or $C_{1-3}$alkyleneC(O)OR$^6$, wherein $R^6$ is H or $C_{1-6}$alkyl;
$R^3$ is

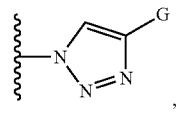

wherein G is a targeting group or a fluorescent probe;
X is a pharmaceutically acceptable counteranion;
Z is —(CR$^7$R$^8$ ----- CR$^9$R$^{10}$-A)$_p$-(CR$^{11}$R$^{12}$ ----- CR$^{13}$R$^{14}$)—;
wherein
A is O or NH;
p is 2, 3 or 4;
----- represents a single or double bond;
when ----- is a double bond, one of $R^7/R^8$ and $R^9/R^{10}$ or $R^{11}/R^{12}$ and $R^{13}/R^{14}$, as applicable, is not present; and
$R^7$ to $R^{14}$ are each independently H, $C_{1-6}$alkyl or aryl; or one of $R^7/R^8$ and $R^9/R^{10}$ and/or $R^1/R^{12}$ and $R^{13}/R^{14}$, together with the carbon atoms to which they are attached, form a 5-6 membered carbocycle;
the N and A atoms in the compound of Formula I(a) form an $N_3A_p$ donor set for coordinating with M;
M is selected from $Fe^{3+}$, $Fe^{2+}$, $Co^{2+}$, $Zn^{2+}$, $Mn^{3+}$, $Mn^{2+}$ and $Gd^{3+}$ and is coordinated in an equatorial fashion by at least three atoms of the $N_3A_p$ donor set;
when M is $Fe^{2+}$, $Co^{2+}$, $Zn^{2+}$ or $Mn^{2+}$, m is 2; and
when M is $Fe^{3+}$, $Mn^{3+}$ or $Gd^{3+}$, m is 3,
for enhancing contrast in a magnetic resonance image of a subject. It will be appreciated by a person skilled in the art that embodiments of such uses can be varied as for the embodiments of the methods of enhancing contrast in a magnetic resonance image of a subject comprising administering a compound of Formula I(a) or a hydrate thereof of the present application.

The compounds of Formula I(a) or Formula I(b) are suitably administered as a sterile aqueous solution comprising an effective amount of the compound of Formula I(a) or Formula I(b). As used herein the term "effective amount" means an amount effective to achieve a desired result. For example, in the context of enhancing contrast in a magnetic resonance image of a subject, an effective amount is an amount that, for example, enhances the contrast in the magnetic resonance image of the subject compared to the magnetic resonance image of the subject without administration of the compound of Formula I(a) or Formula I(b). Effective amounts may vary according to factors such as the age, sex and/or weight of the subject. The amount of a given compound or composition that will correspond to such an amount will vary depending upon various factors, such as the given compound or composition (e.g. compounds of Formula I(b) comprising two Schiff-base macrocycles are typically administered at half the dosage of compounds of Formula I(b) comprising a single Schiff-base macrocycle), the formulation, the route of administration, the type of magnetic resonance image being obtained, the identity of the subject, and the like, but can nevertheless be routinely determined by one skilled in the art.

In an embodiment, the subject is administered about 0.005 to about 0.2 mmol/kg of the compound of Formula I(a). In another embodiment, the subject is administered about 0.01 to about 0.1 mmol/kg of the compound of Formula I(a). In a further embodiment, the subject is administered about 0.01 to about 0.05 mmol/kg of the compound of Formula I(a). In another embodiment of the present application, the subject is administered about 0.01 to about 0.025 mmol/kg of the compound of Formula I(a). In a further embodiment, the subject is administered about 0.01 to about 0.02 mmol/kg of the compound of Formula I(a). It is an embodiment that the subject is administered about 0.01 mmol/kg of the compound of Formula I(a). In another embodiment, the subject is administered about 0.1 mmol/kg of the compound of Formula I(a).

In an embodiment, the subject is administered about 0.005 to about 0.4 mmol/kg of the compound of Formula I(b). In another embodiment, the subject is administered about 0.005 to about 0.2 mmol/kg of the compound of Formula I(b). In a further embodiment, the subject is administered about 0.005 to about 0.1 mmol/kg of the compound of Formula I(b). In another embodiment, the subject is administered about 0.01 to about 0.05 mmol/kg of the compound of Formula I(b). In a further embodiment, the subject is administered about 0.01 to about 0.02 mmol/kg of the compound of Formula I(b). It is an embodiment that the subject is administered about 0.01 mmol/kg of the compound of Formula I(b). In another embodiment of the present application, the subject is administered about 0.02 mmol/kg of the compound of Formula I(b). In a further embodiment of the present application, the subject is administered about 0.1 mmol/kg of the compound of Formula I(b). In another embodiment, the subject is administered about 0.2 mmol/kg of the compound of Formula I(b).

The concentration of the compound of Formula I(a) or Formula I(b) in the sterile aqueous solution can be any suitable concentration. In an embodiment, the concentration is about 3 mM to about 20 mM. In another embodiment, the concentration is about 5 mM to about 15 mM. In a further embodiment, the concentration is about 6.25 mM to about 12.5 mM. It is an embodiment that the concentration is about 6.25 mM. In another embodiment of the present application, the concentration is about 12.5 mM.

In an embodiment, the sterile aqueous solution comprising the compound of Formula I(a) further comprises a bicarbonate buffer solution. In another embodiment, the bicarbonate buffer comprises $Na_2CO_3$ and $NaHCO_3$.

In another embodiment, the sterile aqueous solution comprising the compound of Formula I(b) further comprises a bicarbonate buffer solution. In another embodiment, the bicarbonate buffer comprises $Na_2CO_3$ and $NaHCO_3$.

Methods of administrating contrast agents are well known in the art, the selection of which can be made by a person skilled in the art. In an embodiment, the compounds of Formula I(a) or I(b) are administered via intravenous injection. In another embodiment, the compounds of Formula I(a) or I(b) are administrated by oral administration or via an enema.

The present application also includes a composition comprising one or more compounds of Formula I(a) and a carrier. In an embodiment, the composition is a pharmaceutical composition comprising one or more compounds of Formula I(a) and a pharmaceutically acceptable carrier. In another embodiment of the present application, the pharmaceutically acceptable carrier comprises, consists essentially of or consists of sterile water. In a further embodiment, the pharmaceutically acceptable carrier further comprises a bicarbonate buffer. It is an embodiment that the pharmaceutical composition is formulated for intravenous injection.

The present application also includes a composition comprising one or more compounds of Formula I(b) and a carrier. In an embodiment, the composition is a pharmaceutical composition comprising one or more compounds of Formula I(b) and a pharmaceutically acceptable carrier. In another embodiment of the present application, the pharmaceutically acceptable carrier comprises, consists essentially of or consists of sterile water. In a further embodiment, the pharmaceutically acceptable carrier further comprises a bicarbonate buffer. It is an embodiment that the pharmaceutical composition is formulated for intravenous injection.

The parameters selected for obtaining the magnetic resonance image can be any suitable parameters. Unlike the approved $Gd^{III}$ agents which are used solely as $T_1$-shortening agents, while not wishing to be limited by theory, the studies of the present disclosure suggest that the compounds of Formula I(b) of the present disclosure comprising $Mn^{II}$ may be useful in both $T_1$- and $T_2$-weighted scans (for both positive and negative signal enhancement).

Accordingly, in an embodiment of the present application, the MRI scan is a $T_1$-weighted scan. In another embodiment of the present application, the MRI scan is a $T_2$-weighted scan. In a further embodiment of the present application, the signal enhancement is positive. It is an embodiment of the present application that the signal enhancement is negative.

The following non-limiting examples are illustrative of the present application:

EXAMPLES

Example 1: Schiff-Base Macrocycles as a Platform for a New Family of MRI Contrast Agents I. Experimental (a) Materials and Methods All reagents were purchased from Sigma-Aldrich or Alfa Aesar and used without further purification. Procedures for the synthesis of the organic building blocks are as described in the literature.[22] Infrared spectra were recorded on a Bruker Alpha FT-IR spectrometer. Mass spectrometry data were recorded on a Carlo Erba/Kratos GC/MS acquisition system and processed at a SPARC workstation. Elemental analysis measurements were performed by Atlantic Microlab Inc., Norcross, Ga., USA.

(b) Synthesis of Complexes

General Procedure for Complex Synthesis:
Unless otherwise stated hereinbelow, the complexes were synthesized by the following method. Diacetylpyridine (1 eq.) was added in one portion to a solution of the metal chloride salt (1 eq.) in MeOH (30 mL). The solution was heated to 50° C., and then the appropriate diamine (1 eq.) was added in one portion. The reaction mixture was heated to 85° C. and refluxed for 4-18 h. The solvent volume was reduced by approximately half, and the mixture was cooled to room temperature (r.t.). An excess of diethyl ether ($Et_2O$) was added, and the resulting precipitate was collected by Buchner filtration and washed well with cold $Et_2O$.

[MnL1Cl$_2$].2H$_2$O (1)
The general procedure for complex synthesis was followed. Complex 1 was isolated as a beige solid (0.530 g, 60.4%). IR (cm$^{-1}$) 3330, 3271, 2907, 2853, 1649, 1583, 1457, 1201, 1112, 1049. FAB-MS: m/z=363 [M-Cl]$^+$ (100%). Anal. calcd. for (C$_{15}$H$_{23}$N$_5$Cl$_2$Mn).2H$_2$O C: 45.13; H: 5.81; N: 17.54. found C: 45.01; H: 5.88; N: 17.21%.

[MnL2Cl$_2$].2H$_2$O (2)
The general procedure for complex synthesis was followed. Complex 2 was isolated as a pale yellow solid (0.875 g, 79.1%). IR (cm$^{-1}$) 3508, 3403, 3138, 2923, 2880, 1645, 1586, 1356, 1269, 1205, 1110, 1073, 1039. FAB-MS: m/z=365 [M-Cl] (100%). Anal. calcd. for (C$_{15}$H$_{21}$N$_3$O$_2$Cl$_2$Mn).2H$_2$O C: 41.21; H: 5.76; N: 9.61. found C: 41.19; H: 5.69; N: 9.43%.

[MnL3Cl$_2$].2H$_2$O (3)
Diacetylpyridine (0.134 g, 0.82 mmol) was added in one portion to a solution of MnCl$_2$·4H$_2$O (0.142 g, 0.82 mmol) in EtOH (30 mL). The solution was heated to 50° C., and then 1,4-bis-(2-aminophenyl)-1,4-dioxabutane (0.200 g, 0.82 mmol) was added in one portion. The reaction mixture was heated to 85° C. and refluxed for 4 h. The solvent volume was reduced by half, and the mixture was cooled to r.t. An excess of $Et_2O$ was added, and the resulting precipitate was collected by Buchner filtration and washed well with cold $Et_2O$ to give 3 as an orange solid (62 mg, 14.2%). IR (cm$^{-1}$) 3351, 3072, 2968, 2924, 1671, 1592, 1503, 1362, 1249, 1210, 1087. FAB-MS: m/z=461 [M-Cl]$^+$ (10%). Anal. calcd. for (C$_{23}$H$_{21}$N$_3$O$_2$C$_{1-2}$Mn)$_{0-2}$H$_2$O C: 55.55; H: 4.26; N: 8.45. found C: 55.72; H: 4.65; N: 8.39%.

R,R-[MnL4Cl$_2$].2H$_2$O (4)
The general procedure for complex synthesis was followed. Complex 4 was isolated as a beige solid (0.102 g, 26.5%). IR (cm$^{-1}$) 3372, 4061, 2888, 1650, 1587, 1454, 1210, 1079, 1051, 1018. m/z=517 [M-Cl]$^+$ (100%). Anal. calcd. for (C$_{27}$H$_{29}$C$_{1-2}$MnN$_3$O$_2$).2H$_2$O C: 55.02; H: 5.64; N: 7.13. found C: 55.15; H: 5.63; N: 6.79%.

[MnL6Cl$_2$].2H$_2$O (5)
The general procedure for complex synthesis was followed. Complex 5 was isolated as a yellow solid (0.856 g, 58.1%). IR (cm$^{-1}$) 3423, 3345, 2924, 2873, 1618, 1586, 1492, 1257, 1215, 1117, 1048. m/z=289 [L$^7$+H]$^+$ (60%), 505 [M-Cl]$^+$ (5.9%). Anal. calcd. for (C$_{25}$H$_{25}$N$_3$O$_3$C$_{1-2}$Mn).2H$_2$O C: 52.01; H: 5.06; N: 7.28. found C: 51.88; H: 4.98; N: 7.31%.

[Mn$_2$L7Cl$_4$].5H$_2$O (6)
To a solution of MnCl$_2$·4H$_2$O (0.1347 g, 0.783 mmol) in MeOH (20 mL) was added 2,2',6,6'-tetraacetyl-4,4'-bipyridine (0.1270 g, 0.392 mmol) in one portion. The brown mixture was heated to 50° C., and then 2,2'-(ethylenedioxy)bisethylamine (0.1165 mL, 0.783 mmol) was added. The reaction mixture was heated to 85° C. and refluxed for 18 h. The solvent volume was reduced by half and the solution was passed through a syringe filter. An excess of $Et_2O$ was added, and precipitate was collected by Buchner filtration to give 6 as a beige solid (0.190 g, 54.4%). IR (cm$^{-1}$) 3385, 2932, 1648, 1596, 1378, 1349, 1106, 1071. FAB-MS: m/z=728 [M-2Cl]$^+$ (16.4%). Anal. calcd. for (C$_{30}$H$_{40}$N$_6$O$_4$Cl$_4$Mn$_2$).5H$_2$O C: 40.47; H: 5.66; N: 9.44. found 40.27; H: 5.49; N: 9.52%.

[GdL1Cl$_3$].3H$_2$O (7)
The general procedure for complex synthesis was followed. Complex 7 was isolated as a pale yellow solid (0.144 g, 12.1%). IR (cm$^{-1}$) 3383, 2961, 1631, 1592, 1458, 1372, 1089, 1011. FAB-MS: m/z=465 [M-H-2Cl]$^+$ (2.9%). Anal. calcd. for (C$_{15}$H$_{23}$N$_5$Cl$_3$Gd).3H$_2$O C: 30.48; H: 4.95; N: 11.85. found C: 30.48; H: 5.21; N: 11.95%.

[GdL2Cl$_3$].6H$_2$O (8)
The general procedure for complex synthesis was followed. Complex 8 was isolated as an orange/brown solid (0.287 g, 22.0%). IR (cm$^{-1}$) 3386, 3024, 2924, 1620, 1595, 1460, 1364, 1138, 1096. FAB-MS: m/z=297 [L2+Na]$^+$ (6.6%). Anal. calcd. for (C$_{15}$H$_{21}$N$_3$O$_2$Cl$_3$Gd).6H$_2$O C: 27.84; H: 5.14; N: 6.49. found C: 27.89; H: 5.23; N: 6.35%.

[GdL6Cl$_3$].6H$_2$O (9)
The general procedure for complex synthesis was followed. Complex 9 was isolated as a brown solid (0.148 g, 31.3%). IR (cm$^{-1}$) 3331, 2868, 2497, 2360, 2341, 1628, 1594, 1504, 1362, 1263, 1127, 1055. FAB-MS: m/z=289 [L7+H]$^+$ (100%). Anal. calcd. for (C$_{25}$H$_{25}$N$_3$O$_3$Cl$_3$Gd).6H$_2$O C: 38.14; H: 4.74; N: 5.34. found C: 38.14; H: 4.74; N: 5.34%.

(c) Relaxivity Measurements $T_1$ and $T_2$ relaxation times were measured at the STTARR Innovation Centre in Toronto, Canada using a Bruker minispec mq60, and at the Bruker Showroom in Milton, Canada using a Bruker minispec mq20. Measurements were carried out on a series of 6 aqueous dilutions between 0-5 mM.

(d) In Vitro Methods

Reference Compound:
Gadodiamide (Selleckchem, Lot #02) was used as the reference compound. It is one of the 8 Gd(III)-based MRI agents approved for use in Canada (trade name: Omniscan™).

Preparation of Test Articles and Reference Compound:
The test articles and reference compound were weighed and dissolved in the incubation medium to give the highest test concentration of 30 mM. The solution was filter sterilized and diluted to the remaining test concentrations of 10 mM, 3.3 mM, 1.1 mM, 0.36 mM, 0.12 mM and 0.04 mM.

Preparation of Cells:
Cryopreserved primary rat renal proximal tubule epithelial cells (RPTECs) (ScienCell Research Laboratories, Carlsbad, Calif.) were used for the study. The rat RPTECs were thawed completely at 37° C., and transferred to epithelial cell medium (ScienCell Research Laboratories, Carlsbad, Calif.) followed by plating in poly-L-lysine coated 96-well plates. The RPTECs were allowed to recover and grow in a cell culture incubator (37° C., humidified atmosphere of 5% carbon dioxide and 95% air) for 3 additional days with a medium change every alternate day.

Treatment of Cells:

Following 3 days of plating, the RPTECs were washed once with serum free epithelial cell medium (ScienCell Research Laboratories, Carlsbad, Calif.) followed by treatment with the test, reference or control articles for 2, 4, 10 or 24 h. All treatments were performed in triplicate.

Quantification of Cell Viability:

Cellular viability and metabolic activity were assessed by using the 3-(4,5-dimethylthiazol-2-yl)-2,5-diphenyl tetrazolium bromide (MTT) uptake assay. A 10× stock of the MTT dye was prepared in phosphate buffered saline (PBS). An aliquot of dye was added 2 hrs before the intended time point to achieve a final 1× concentration, after which incubation (37° C., humidified atmosphere of 5% carbon dioxide and 95% air) continued until the desired time point. For the 2 hr time point, the aliquot of dye was added immediately after the test articles. Following incubation, all media was aspirated from the wells and the plates were allowed to dry. The resulting formazan crystals were dissolved in DMSO using an orbital shaker, and the absorbance at 570 nm was measured using a Victor $^3$V multilabel plate reader (reference wavelength=650 nm).

Data Analysis:

The inhibitory concentration ($IC_{50}$, the concentration resulting in 50% toxicity) was determined by plotting log concentration vs. relative viability, followed by non-linear regression of the curve using Graph Pad Prism 5.0.

(e) In Vivo Methods

Preliminary in vivo studies were performed at the Animal Resource Centre and the STTARR Innovation Centre, Toronto. Necropsy and histopathology were carried out by Mbed Pathology.

Acute Toxicity:

Compound 1 (aq., 12.5 mM) was injected intravenously into 4 male rats (Sprague Dawley Crl:SD, 315-340 g) at a dosage of 0.02 mmol/kg following anaesthesia with 5% isoflurane. The animals were observed for a period of 14 days. Body weight measurements and hematology were performed on days −1, 7 and 14. Compound 6 (aq., 6.25 mM) was injected intravenously into 8 male rats (Sprague Dawley Crl:SD, 327-365 g) at a dosage of 0.01 mmol/kg following anaesthesia with 5% isoflurane. The animals were observed for a period of 8 days. Body weight measurements and hematology were performed on days −1, 1 and 8. Following euthanasia, the heart, lungs, liver, kidneys, spleen, thyroid and pituitary glands were grossly examined during necropsy, and samples of the brain, heart (compound 1 only), lungs, liver, kidneys, spleen and thymus (compound 1 only) were microscopically evaluated during histopathological examination.

Imaging:

Compound 1 (aq., 12.5 mM) was injected intravenously into 2 male rats (Sprague Dawley Crl:SD, 312-338 g) at a dosage of 0.02 mmol/kg following anaesthesia with 5% isoflurane. Compound 2 (aq., 6.25 mM) was injected intravenously into 1 male rat (Sprague Dawley Crl:SD, 349 g) at a dosage of 0.01 mmol/kg following anaesthesia with 5% isoflurane. Compound 6 (aq., 6.25 mM) was injected intravenously into 1 male rat (Sprague Dawley Crl:SD, 341 g) at a dosage of 0.01 mmol/kg following anaesthesia with 5% isoflurane. Anesthesia was maintained at 2-2.5% isoflurane through a nose cone for the duration of the scans. Fast-spin-echo images were collected for 45 mins. immediately post-injection. For compound 1, the DT1-weighted RARE (Rapid Acquisition Relaxation Enhancement) scans were acquired with an echo time of 10 ms, and a repetition time=respiratory cycle duration (~1100 ms). Both T1- and T2-weighted scans were collected on compounds 2 and 6.

II. Results and Discussion

An expanded family of $Mn^{II}$ and $Gd^{III}$ complexes of Schiff-base macrocycles, based on the known $Mn^{II}$ complexes 1 and 2 has been prepared and the potential of these compounds for use as MRI contrast agents is discussed hereinbelow. These complexes can offer, for example, a stability associated with their metal-templated formation, high relaxivities, and/or a functionalizable backbone for the development of dual-property agents.

The structures of macrocyclic ligands L1-L7 are shown in Scheme 4.

Scheme 4. Macrocycles L1-L7, grouped by number and nature of donor atoms.

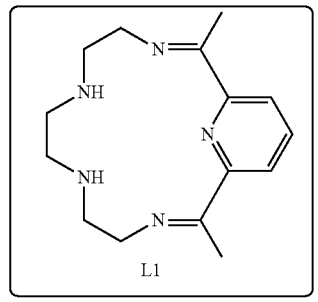

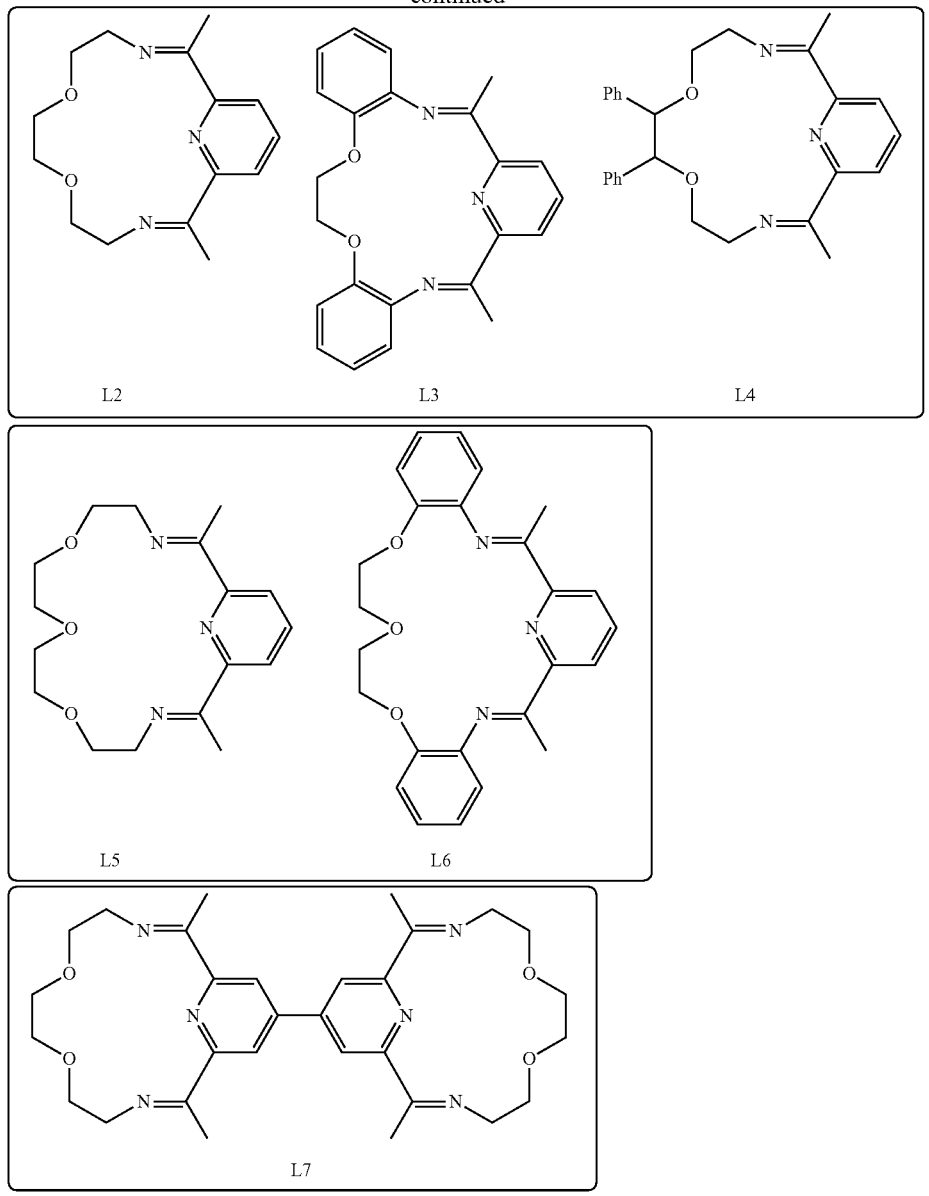

L1 is an $N_5$ macrocycle, the first of the family to be reported in the literature. It has a 15-membered macrocyclic backbone. L2 is the $N_3O_2$ analogue of La, differing in the character of its donor atoms L3 and L4 maintain the size and donor character of the $N_3O_2$ macrocyclic cavity, but have increased rigidity (L3) or bulk (L4). Additionally, macrocycle L4 is an optically active system, with adjacent chiral centres on the central ethylene linker. L5 and L6 have an expanded cavity, with an additional O donor atom and an 18-membered backbone. L5 is the larger analogue of L2, with flexible ethylene linkers, while L6 is the analogue of the more rigid L3. Finally, L7 is made up of two covalently-tethered L2 macrocycles, linked at the 4-position of the pyridine head units. By studying this expanded family of macrocyclic systems, the effect of the number and nature of donor atoms, and the cavity size, bulk, and rigidity, on the relaxivities of the resulting complexes was investigated.

(a) Synthesis and Characterization

The non-commercially available organic building blocks used for the formation of macrocycles L3 and L5-7 were synthesized following a variety of modified literature procedures.[22] The diamine used for the formation of the chiral macrocycle L4 was prepared via a synthetic pathway developed by the Pilkington group.[23] The metal salts chosen for templation were the hydrated chloride salts $MnCl_2$ and $GdCl_3$, due to the biological compatibility of the chloride anion.

The complexes were synthesized following the procedure for metal templated cyclization described by Nelson and Drew.[24] The appropriate diketone and diamine were refluxed with the desired metal chloride salt in methanol at 85° C. for 4-18 hours, before precipitation of the desired complex by the addition of an excess of diethyl ether at room temperature. Attempts were made to template each of macrocycles L1-L7 around both $Mn^{II}$ and $Gd^{III}$. Complexes of the formula $[MCl_n(H_2O)_m]$ were isolated, where n=2 for $M=Mn^{II}$ and n=3 for $M=Gd^{III}$. Macrocycle formation was confirmed by infrared spectroscopy, with the appearance of a peak corresponding to imine C=N stretch ca. 1620-1670 cm$^{-1}$ (shown in Table 2), and the absence of a peak corresponding to ketone C=O stretch, ca. 1720 cm$^{-1}$. The compounds which were isolated with a high degree of analytical purity (+/−0.4%) are listed in Table 2.

Figure 2:
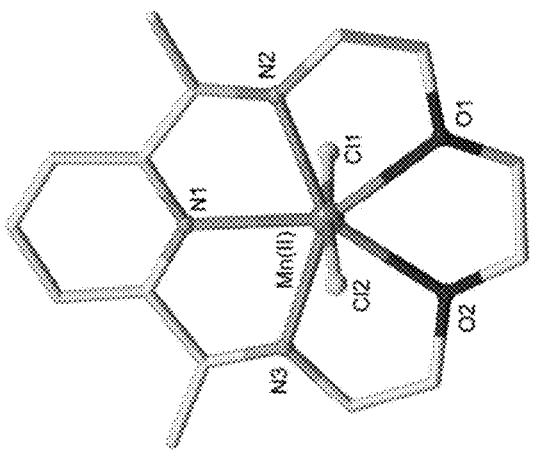
FIG. 2 shows crystal structures of exemplary complexes 1 (left, centre) and 2 (right). H atoms and non-coordinating water molecules are omitted for clarity.
Figure 2:
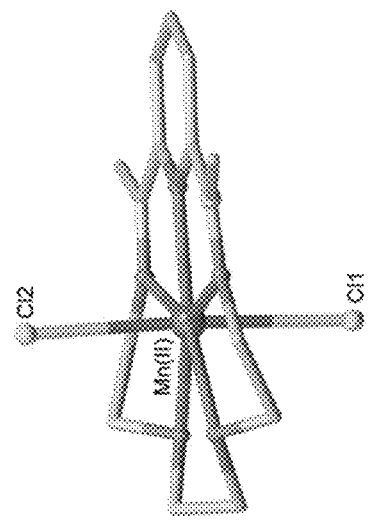
Figure 2:
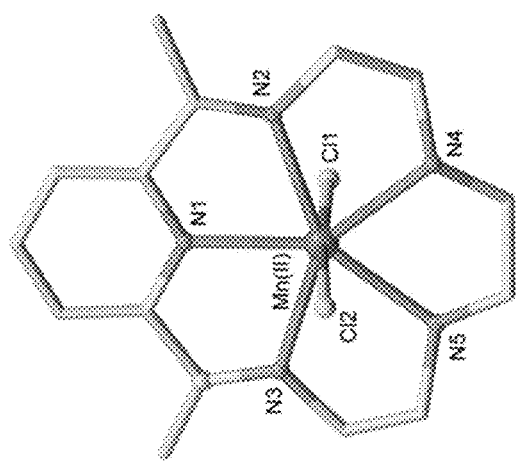

$Mn^{II}$ Complexes:

Complexes 1 and 2 have both been reported previously.[25] Crystal structures[25] of the two complexes (FIG. 2) show the $Mn^{II}$ ions lying in a 7-coordinate, pentagonal bipyramidal environment. The five donor atoms of the macrocyclic ring ($N_5$ for 1 and $N_3O_2$ for 2) bind in the equatorial plane, and two monodentate ligands are bound axially. In the solid state, each complex has two axially-bound chloride ions (FIG. 2). However, in order to display the observed relaxivity behaviour discussed in the following section, one or both chloride ions is displaced by a bound water molecule in aqueous solution. Conductance measurements on complexes 1 and 2 indicated that in solution, both chloride ions were displaced by water molecules. The dinuclear derivative of 2, complex 6, was previously reported by the Pilkington group,[26] and the solid state structure deduced by X-ray diffraction showed that the two $Mn^{II}$ ions lie in identical pentagonal bipyramidal environments, each with one axial chloride and one axial water ligand. Ethanol was used as the solvent for complex 3, because hydrolysis of one or both imine bonds was observed to occur in methanol. This complex was completely insoluble in water. The $Mn^{II}$ complex of L4 formed readily in methanolic conditions to give 4, in accordance with the similarity of its coordination environment to that of L2. The only target macrocycle which was not observed to be templated around $Mn^{II}$ was the aliphatic macrocycle L5. While not wishing to be limited by theory, the flexibility of L5 combined with its larger cavity size may have contributed to its inability to template around $Mn^{II}$ under the conditions used, in contrast to the smaller derivative L2 and the more rigid derivative L6, which both cyclized with ease to give complexes 2 and 5.

$Gd^{III}$ Complexes:

Macrocycles L1, L2, and L6 formed around $Gd^{III}$, to give complexes 7-9. To the best of the inventors' knowledge, these are the first analytically pure Schiff-base macrocyclic complexes of $Gd^{III}$ to be reported. While not wishing to be limited by theory, the larger ionic radius of this lanthanide ion, and preferred higher coordination numbers, may have affected the ability of the remaining macrocycles to cyclize under the conditions used. Attempts were made to grow X-ray quality single crystals of the complexes by slow evaporation, vapour diffusion and layering in numerous solvents, but only powders were isolated. Thermogravimetric analysis in the solid state, and conductance measurements in solution, were performed on complex 8 to gain insight into number and nature of the axially-bound ligands. Complex 8 appeared to be 7- or 8-coordinate, with the five donor atoms of the macrocycle bound along with two or three axial ligands. In the solid state, one or two chloride ions and one water molecule appeared to be bound; while in solution, only one chloride appeared bound.

Of the compounds listed in Table 2, all but complex 3 were water soluble and thus were studied for their potential as contrast agents.

(b) Relaxivity Measurements

The $T_1$ and $T_2$ relaxation times of the 8 soluble, pure complexes were measured in aqueous solution at 37° C., at both 20 and 60 MHz. The resulting $r_1$ and $r_2$ relaxivity values are given in Table 3.

Several of the compounds exhibited relaxivity values significantly higher than those of the approved agents, which have $r_2$ values in the range of 3.7 to 6.6 s$^{-1}$ mM$^{-1}$ under similar conditions (20 MHz, aqueous solution), with a mean value of 4.9 s$^{-1}$ mM$^{-1}$. For example, the $Mn^{II}$-based complexes displayed $r_2$ relaxivities up to 42.9 s$^{-1}$ mM$^{-1}$, suggesting that these compounds will, for example, provide useful image contrast and/or enhancement.

(c) In Vitro Toxicity

An in vitro toxicity study was performed in order to evaluate the cytotoxic potential of several of the agents in primary rat renal proximal tubule epithelial cells (RPTECs), prior to performing in vivo studies. The $Mn^{II}$ and $Gd^{III}$ complexes of L1, L2 and L6 (complexes 1, 2, 5, and 7-9) were evaluated at seven concentrations (30 mM, 10 mM, 3.3 mM, 1.1 mM, 0.36 mM, 0.12 mM and 0.04 mM) after 2, 4, 10 and 24 hours of treatment in rat RPTECs. The MTT assay was used as an indicator of viability. The nephrotoxic potential of the test articles was compared to the toxicity observed in the presence of the approved agent Gadodiamide. The results are summarized in Table 4, where the inhibitory concentration ($IC_{50}$, the concentration resulting in 50% toxicity) was determined by plotting log concentration vs. relative viability.

As shown in Table 4, following 2 and 4 h of treatment, complex 1 and reference article Gadodiamide did not show significant nephrotoxicity at the concentrations tested. However, a decrease in viability was observed in the cells which were treated with 2, 5, and 7-9, suggesting a degree of nephrotoxicity at these time points. At the 10 h time point, 1 still did not display significant cytotoxicity. Complexes 2, 5, 7 and 8 exhibited a slight reduction in toxicity, while not wishing to be limited by theory, suggesting that the cells might be recovering from the effects of the test articles. Complex 9 did not show a significant change in toxicity from the 4 to the 10 h time point. Reference article Gadodiamide showed more toxicity than earlier time points after 10 hr of treatment. Following 24 h of treatment, all six test articles and the reference article showed some level of toxicity, with 1 and Gadodiamide exhibiting the least nephrotoxic effects.

(d) In Vivo Study

An in vivo toxicity and imaging study was performed on compounds 1 ($[MnL1Cl_2].2H_2O$) and 6 ($[Mn_2L7Cl_4(H_2O)_2].3H_2O$). An in vivo imaging study was also performed on compound 2 ($[MnL2Cl_2].2H_2O$).

Acute Toxicity:

The acute toxicities of 1 and 6 were studied in 8 week old male Sprague-Dawley rats. The toxicity of 1 was studied over a period of 14 days, in four rats; while the toxicity of 6 was studied over a period of 8 days, in 8 rats. Compound 1 was injected intravenously at a dosage of 0.02 mmol/kg (c=12.5 mM), while 6 was injected at a dosage of 0.01 mmol/kg (c=6.25 mM). These dosages were chosen because the dosage for the only $Mn^{II}$-based compound approved in North America, Teslascan, was 0.005 mmol/kg; and the inventors were anticipating a lower degree of toxicity.

Based on clinical observations, hematology, and gross and microscopic examination, complex 1 at the studied dosage can be considered minimally- to non-acutely toxic to rats over the initial two week period post-dose. No clinical signs of toxicity were observed throughout the period of the study, and healthy weight gain by all four rats was recorded. Blood was collected and analyzed on study days 7 and 14. There were no statistically significant deviations in the hematological and biochemical parameters measured on days 7 and 14 in comparison to the baseline measurements taken prior to the study.

Following euthanasia on day 14, necropsy was performed. The heart, lungs, liver, kidneys, spleen, thyroid and pituitary glands of each rat were observed to be grossly unremarkable. A very small adhesion between the lung and thoracic wall was observed in one rat, while not wishing to be limited by theory, possibly reflecting a previous localized pleural inflammation. A small degree of variation was found among the organ weight for the four rats, and in comparison to the organ weights reported in a historical database.[27]

Figure 3:
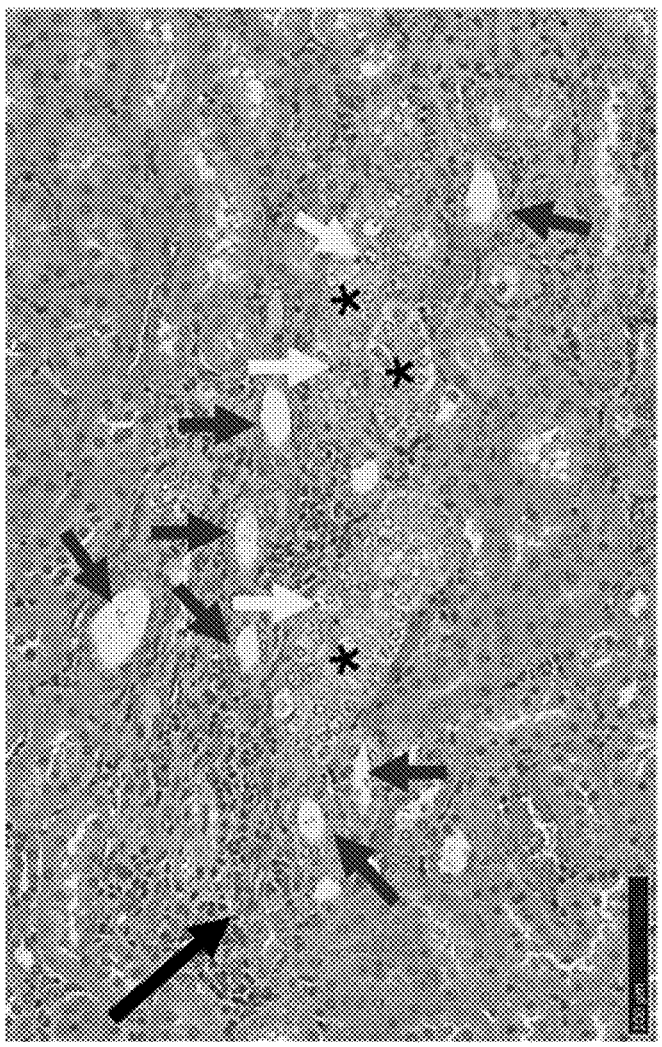
FIG. 3 is an image showing evidence of renal cortical tubular necrosis and regeneration in a kidney of rat following euthanasia 14 days after administration of exemplary compound 1. The cortical tubules are lined with attenuated epithelial cells (short, dark grey arrows) or large epithelial cells with open nuclei (asterisks). Individual dead epithelial cells (short, light grey arrows) are interspersed and the surrounding interstitium is expanded by a small number of lymphocytes and plasma cells (longer, black arrow at far left). Scale bar is 100 µm.

Tissue samples from the brain, heart, lungs, liver, kidneys, spleen and thymus were examined histopathologically. Renal tubular necrosis was evident in kidney tissue harvested from three of the four rats, while not wishing to be limited by theory, attributable to the administration of compound 1. The necrosis spared the epithelial basement membrane of the affected tubules, allowing for repair by re-epithelialization instead of fibrosis and scarring, a characteristic typical of nephrotoxic injury. The amount of injury was very minimal, with less than approximately 1-2% of the renal tubules affected (FIG. 3).

Figure 4:
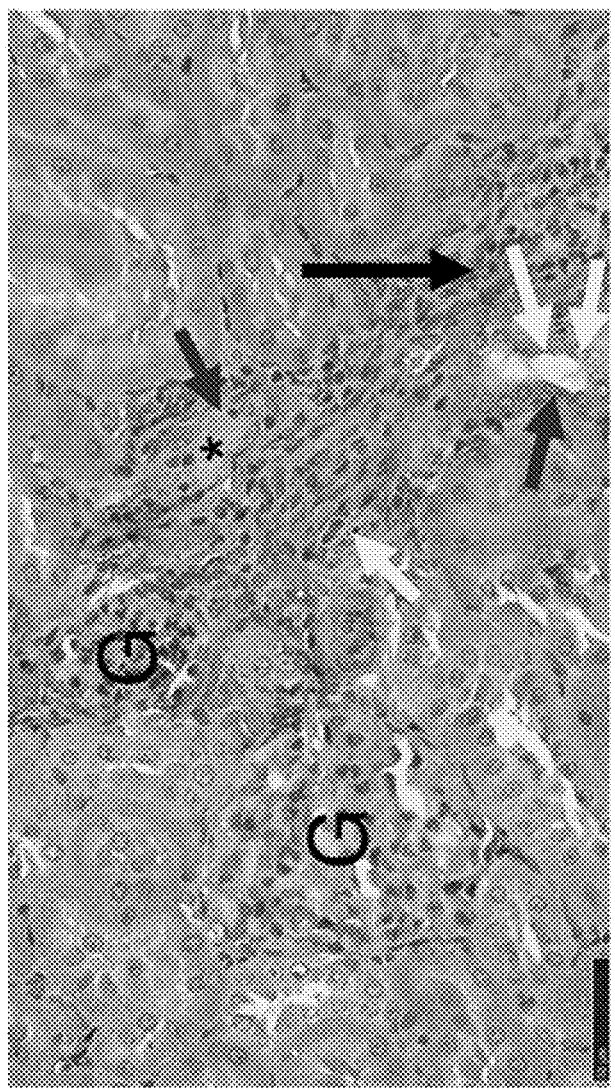
FIG. 4 is an image showing evidence of renal cortical tubular necrosis and regeneration in a kidney of a rat following euthanasia 8 days after administration of exemplary compound 6. The cortical tubules are lined with attenuated epithelial cells (short, dark grey arrows) and some contain luminal protein (asterisk). A few dead epithelial cells (short, light grey arrows) are interspersed and a small number of lymphocytes and macrophages expand the surrounding interstitium (longer, black arrow). Glomeruli are indicated by the letter G. Scale bar is 50 µm.

Like complex 1, complex 6 displayed minimal to no acute toxicity over the first 8 days post-dosage, with no clinical observations of toxicity and no significant hematological or biochemical deviations noted during blood analysis on study days 1 and 8 in comparison to the baseline values recorded pre-study. Following euthanasia on day 8, necropsy was performed. The heart, liver, kidneys, spleen, thyroid and pituitary glands of each rat were observed to be grossly unremarkable. Six of the eight rats displayed minor pulmonary lesions; areas of subtle depression which were red/purple in colour, consistent with atelectasis, or partial lung collapse. However, these lesions may have resulted from the euthanasia process; during exsanguination under isoflurane anesthesia, respiration is slow and shallow. Histopathological analysis of the tissue samples from the liver, kidneys, lungs, spleen and brain of two rats were examined histopathologically. No significant lesions were observed in the liver, spleen and brain samples. Renal tubular necrosis was evident in kidney tissue harvested from one of the two rats, similar in scope (1-2%) to that observed after administration of compound 1; and similar epithelial regeneration had occurred (FIG. 4).

Imaging:

The in vivo contrast potential of compounds 1, 2 and 6 were studied via the collection of fast-spin-echo images for 30-45 minutes immediately following injection of an aqueous solution of each complex. The dosage chosen for 1 was 0.02 mmol/kg (c=12.5 M) while the dosage chosen for 2 and 6 was 0.01 mmol/kg (c=6.25 mM). Predominantly $T_1$-weighted scans with some $T_2$-weighting were performed on two rats injected with 1.

Figure 5:
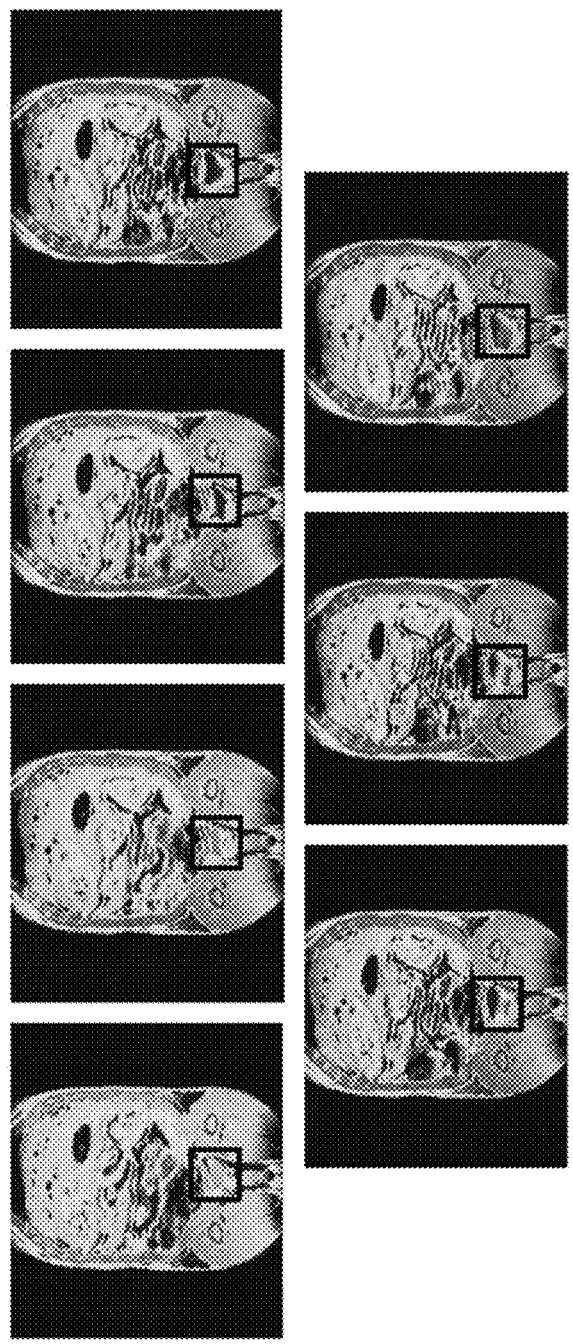
FIG. 5 shows coronal slices of a rat at the level of the bladder (box), showing enhancement due to exemplary complex 1. Top left to right: 0, 2, 10, 15 minutes; bottom left to right: 20, 30, 45 minutes.
Figure 6:
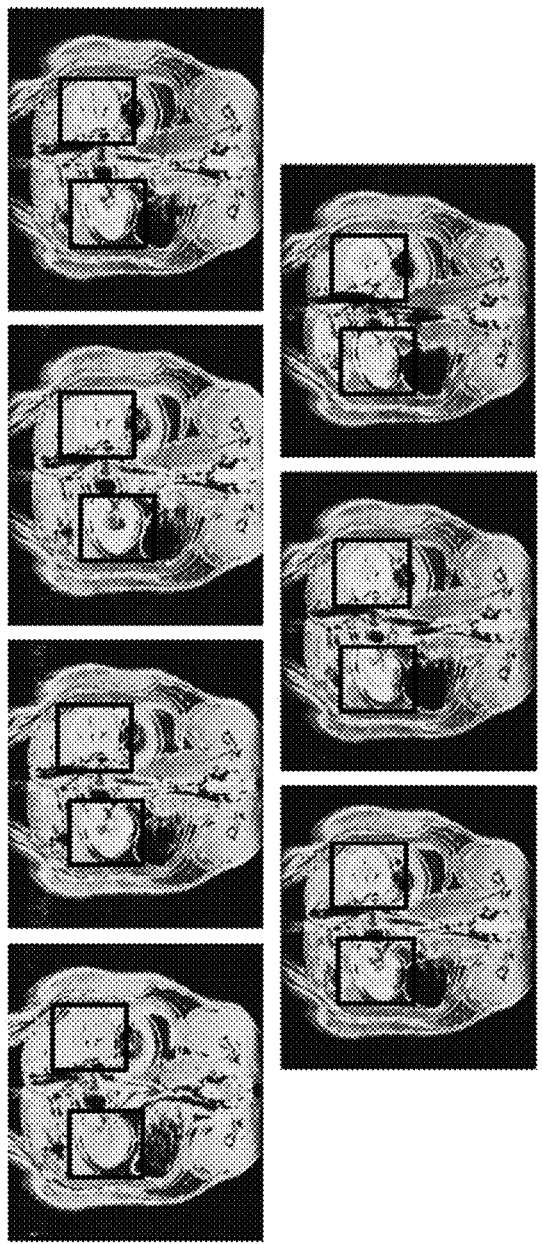
FIG. 6 shows coronal slices of a rat at the level of the kidneys (boxes), showing enhancement due to exemplary complex 1. Top left to right: 0, 2, 10, 15 minutes; bottom left to right: 20, 30, 45 minutes.
Figure 7:
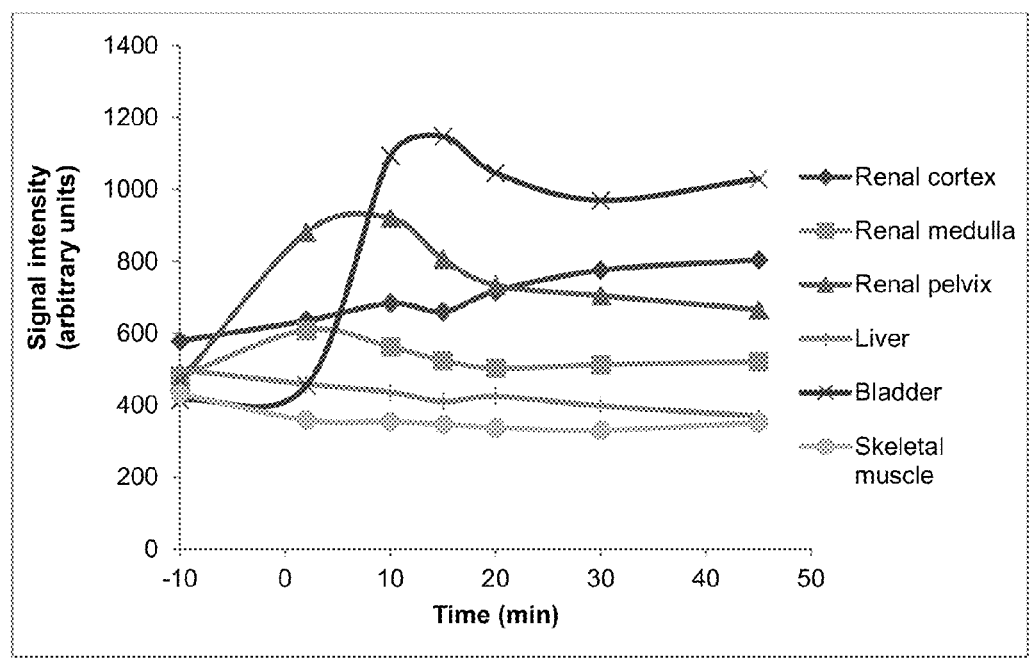
FIG. 7 is a plot showing the change in MRI signal intensity over the first 45 minutes post-injection of exemplary complex 1. The baseline scan was collected at t=−10 minutes.

The compound was observed to appear in the bladder within 5 minutes (FIG. 5). A slow increase in the renal cortical signal was apparent over the first 45 minutes (FIG. 6), along with a gradual liver hypoenhancement (darkening), reflecting an increase in $T_2$ relaxivity in this organ. The signal alteration can be quantified by the mean voxel intensities measured in each tissue. The time point at which the maximum intensity difference was observed is highlighted in Table 5, along with the change as a percentage of the initial intensity. The signal alteration is also visually represented in FIG. 7.

Scans collected 3 hours post-injection showed no evidence of compound 1 being retained by any tissue or organ, indicating very rapid excretion.

Both $T_1$- and $T_2$-weighted scans were performed on two rats injected with 2 and its dimeric analogue 6.

Figure 8:
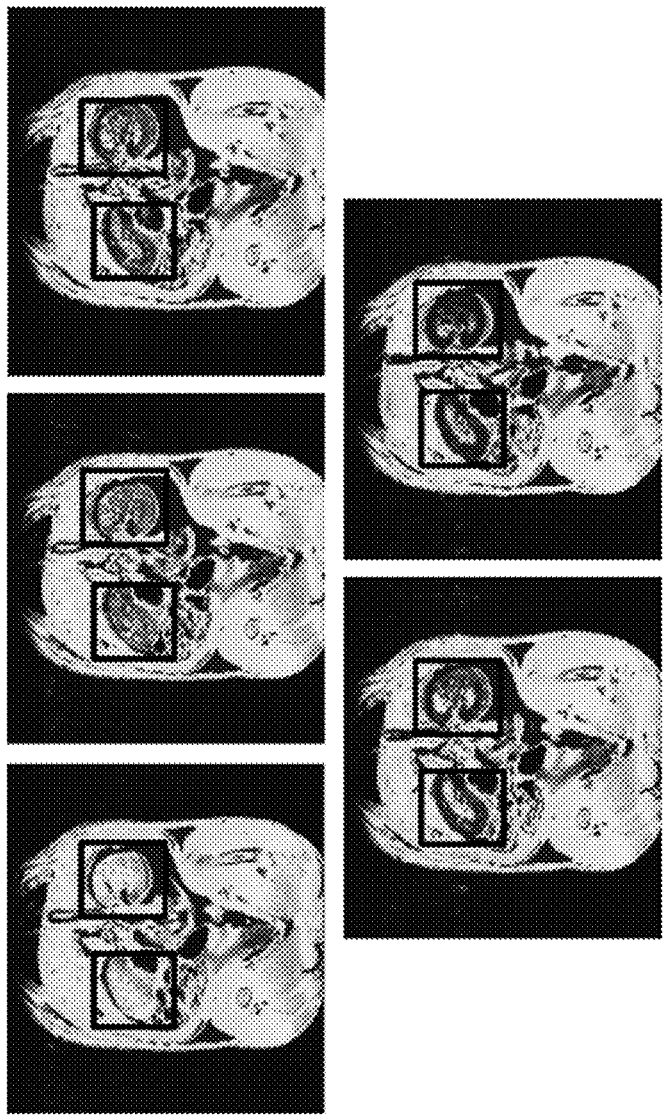
FIG. 8 shows coronal slices at the level of the kidneys, showing enhancement of the $T_1$-weighted MRI signal due to exemplary complex 2. Top left to right: −10, 0, 15 minutes; bottom left to right: 30, 44 minutes.
Figure 9:
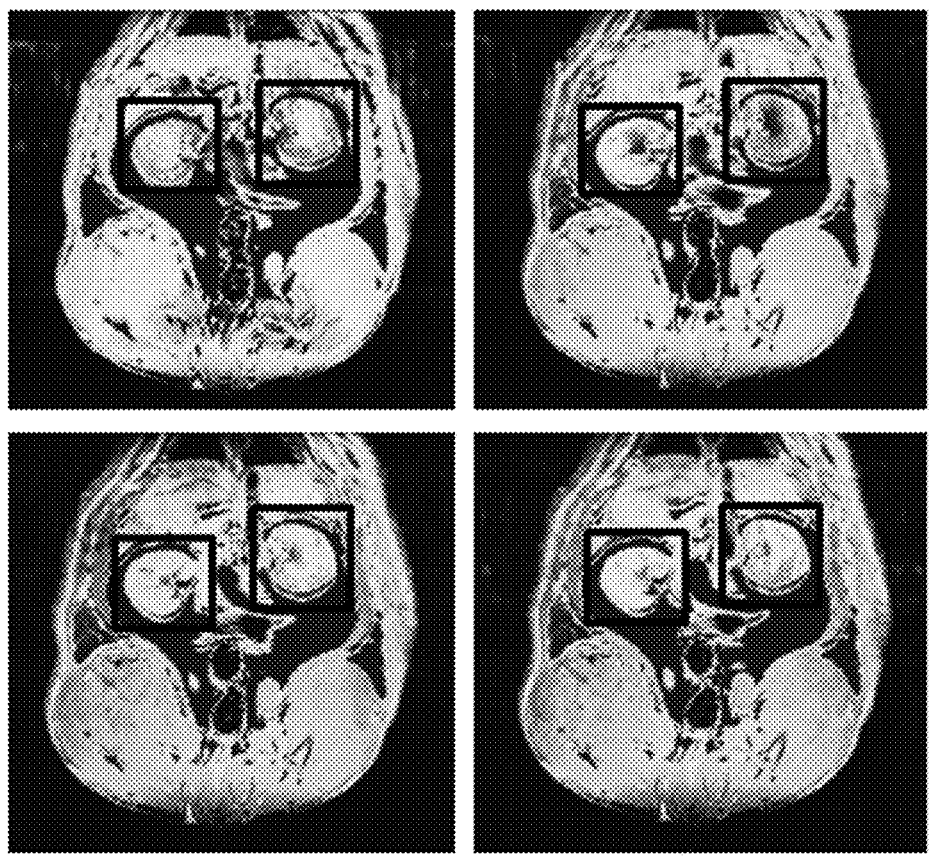
FIG. 9 shows coronal slices at the level of the kidneys, showing enhancement of the $T_1$-weighted MRI signal due to exemplary complex 6. Top left to right: −10, 1 minutes; bottom left to right: 16, 29 minutes.
Figure 10:
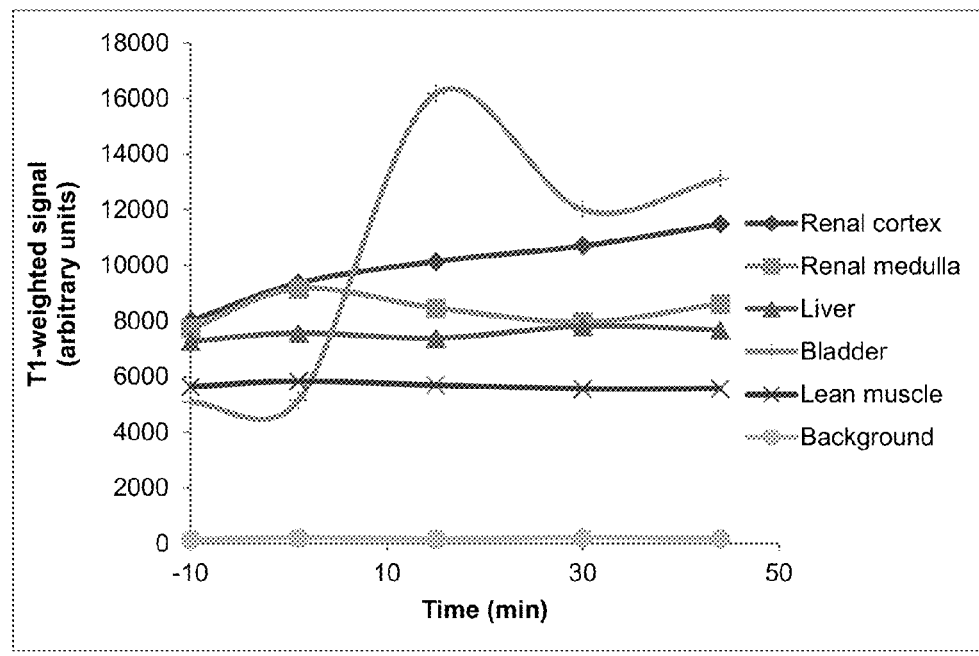
FIG. 10 is a plot showing the change in $T_1$-weighted MRI signal intensity over the first 45 minutes post-injection of exemplary complex 2. The baseline scan was measured at t=−10 minutes.
Figure 11:
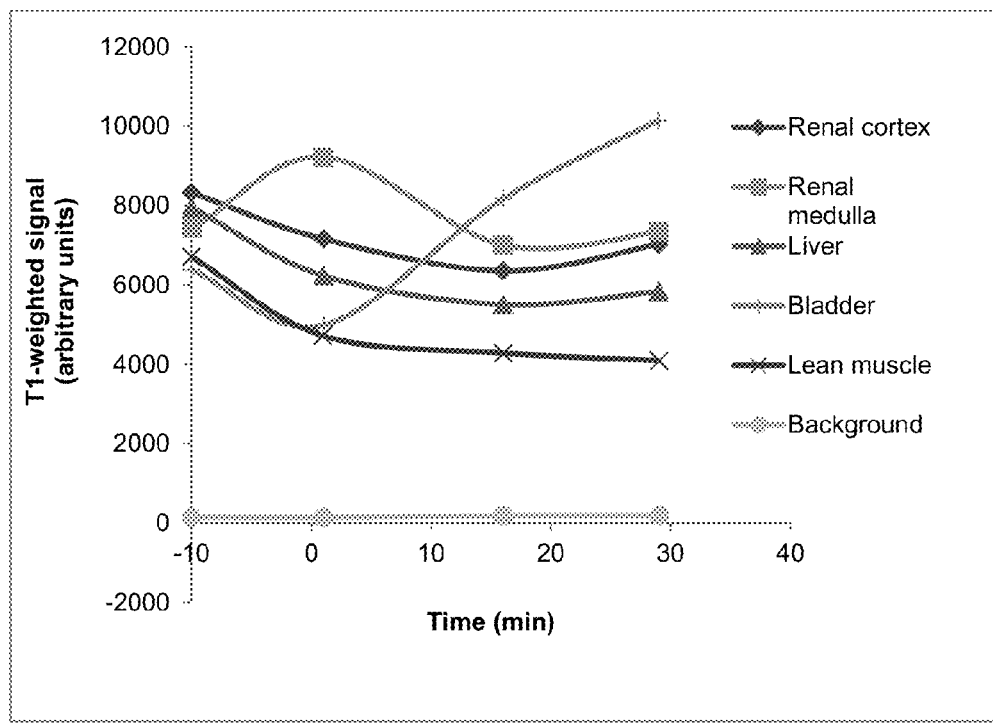
FIG. 11 is a plot showing the change in $T_1$-weighted MRI signal intensity over the first 30 minutes post-injection of exemplary complex 6. The baseline scan was measured at t=−10 minutes.

$T_1$-weighted scans showed both compounds appearing in the bladder within 10 minutes, with 2 appearing before 6, suggesting slightly faster excretion of this monomeric system. While both complexes cause an increase in signal intensity in the renal medulla (FIGS. 8-9), compound 2 causes an enhancement in the renal cortex and has negligible effect on liver and lean muscle tissue; while 6 causes a decrease in signal intensity in all three of these tissues. These results are summarized in Tables 6-7 and FIGS. 10-11.

Figure 12:
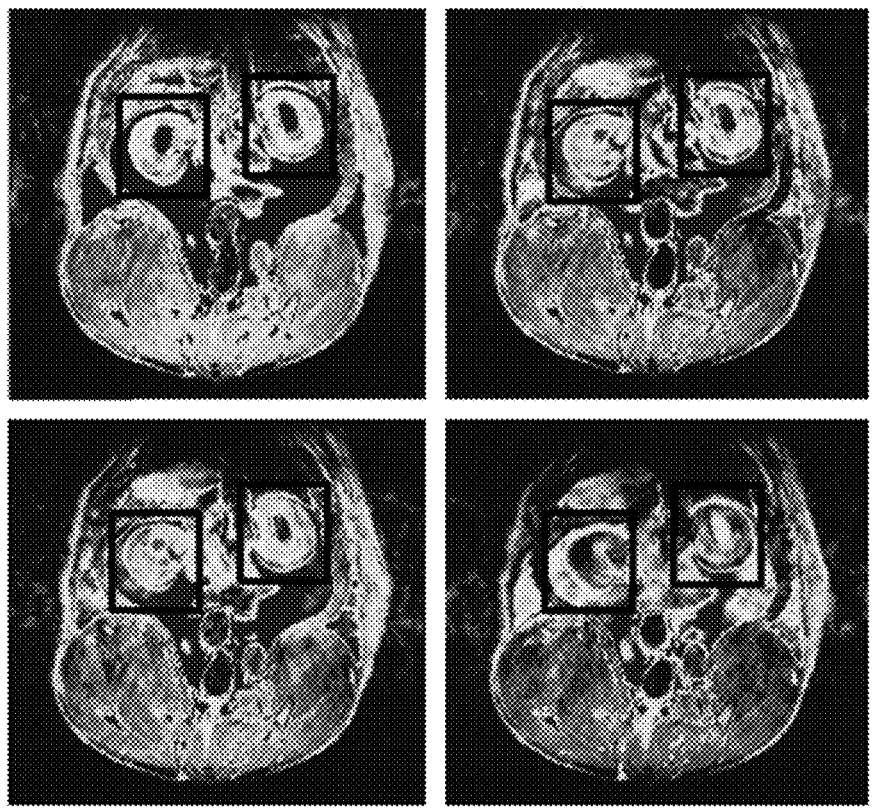
FIG. 12 shows coronal slices at the level of the kidneys (boxes), showing hypoenhancement of the $T_2$-weighted MRI signal due to exemplary complex 6. Top left to right: −10, 9 minutes; bottom left to right: 22, 35 minutes.
Figure 13:
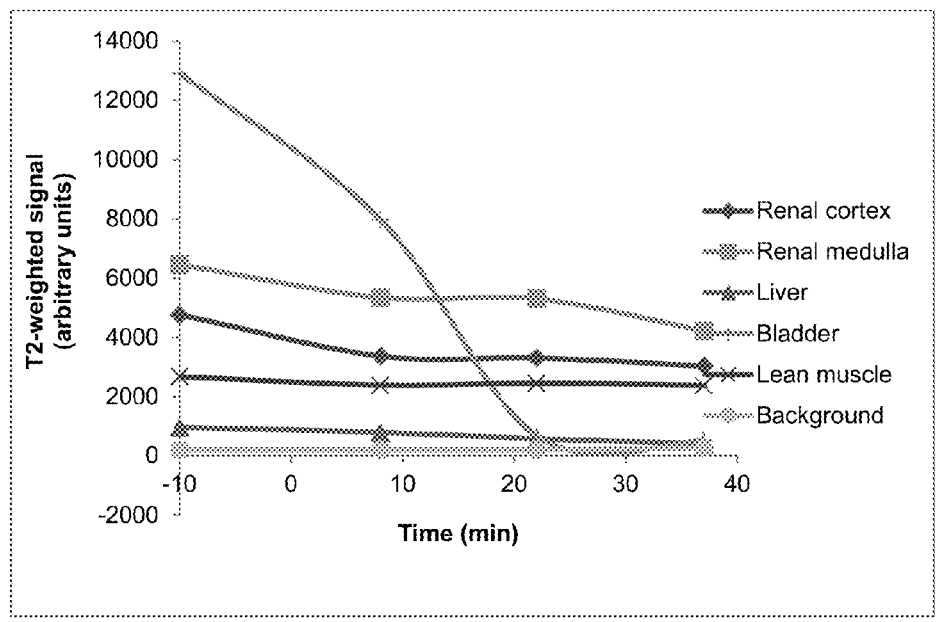
FIG. 13 is a plot showing the change in $T_2$-weighted MRI signal intensity over the first 40 minutes post-injection of exemplary complex 2. The baseline scan was measured at t=−10 minutes.
Figure 14:
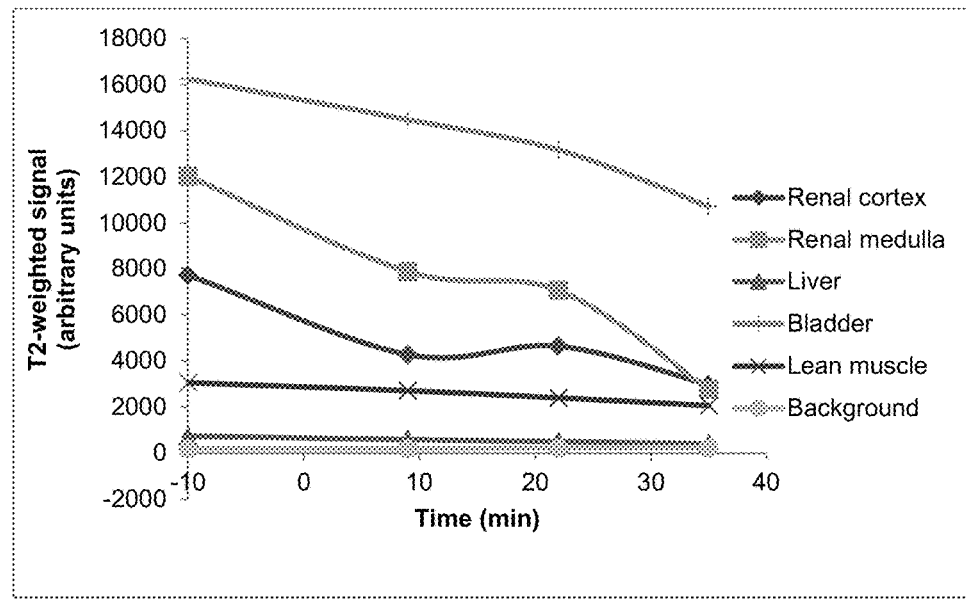
FIG. 14 is a plot showing the change in $T_2$-weighted MRI signal intensity over the first 40 minutes post-injection of exemplary complex 6. The baseline scan was measured at t=−10 minutes.

$T_2$-weighted scans showed a decrease in signal intensity in the bladder, as well as kidney, liver and muscle tissue over the 30-40 minutes following injection of each compound (FIG. 12). The hypoenhancement due to 6 was greater than that due to 2, which correlates with the fact that the compounds were administered at equimolar concentrations and 6 contains double the number of metal centers (FIGS. 13-14; Tables 8-9).

The results from these studies on the $Mn^{II}$ complexes 1, 2 and 6 showed negligible toxicity (for 1 and 6), rapid excretion, and obvious MRI signal enhancement in each case.

Example 2: Functionalization Via 'Click' Chemistry

A strategy has been developed for appending a variety of moieties to the backbone of the complexes, for the formation of a targeted contrast agent. This is accomplished using 'click chemistry' via the copper catalyzed azide-alkyne cyclo-addition (CuAAC) reaction. The CuAAC reaction involves an organic azide and a terminal alkyne reacting to form a 1,4-substituted-1,2-3-triazole. It is, for example, high yielding, applicable to virtually any azide and alkyne pairing, and produces a chemically stable triazole product.[28]

The backbone of macrocycles L1 to L6 includes a substituted pyridine head-unit. An azido group has been appended to the 4-position of the pyridine to give the novel azide 14 according to Scheme 5.

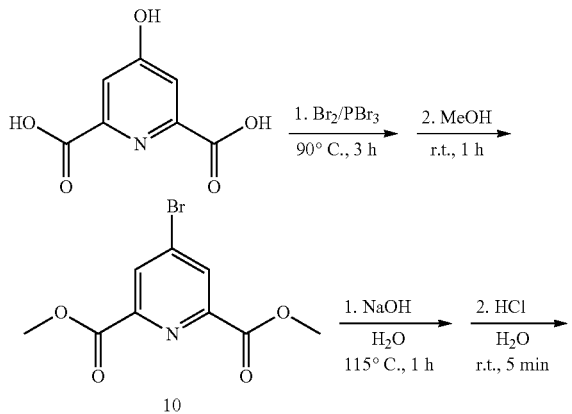

Scheme 5. Synthesis of 4-azido-2,6-diacteylpyridine, 14.

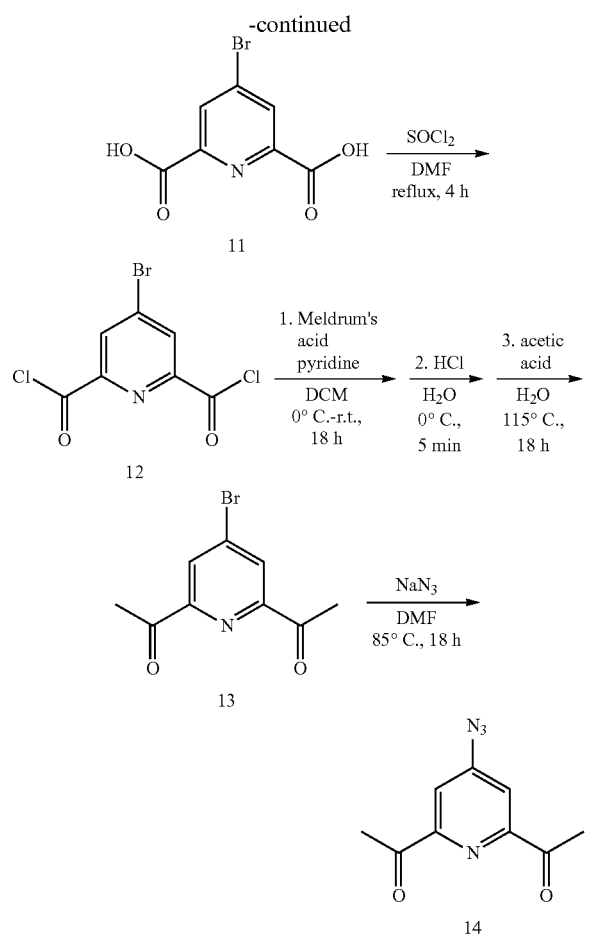

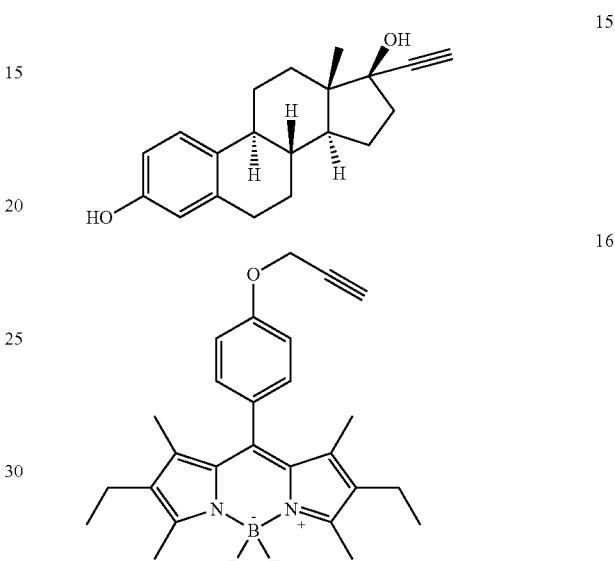

Following literature methodologies, commercially available chelidamic acid was reacted with phosphorous pentabromide, formed in situ from bromine and phosphorous tribromide.[29] Subsequent treatment with methanol at 0° C. yielded the dimethylester 10, which was subjected to basic hydrolysis to regenerate the carboxylic acid functionalities in 11,[30] which were then activated by conversion to the acyl chloride derivatives via reflux in thionyl chloride to give 12. To synthesize the rare bromodiketone 13 a tri-step procedure involving reaction with Meldrum's acid,[31] was employed to give 13 in good yields. The novel azide 14 was prepared by nucleophilic substitution with a large excess of sodium azide.[32]

Synthesis and Characterization of 2,6-diacetyl-4-azidopyridine:

NaN$_3$ (10 eq., 0.209 g, 3.22 mmol) was added to a vigorously stirred solution of 13 (1 eq., 0.078 mg, 0.322 mmol) in DMF/H$_2$O (10 mL, 4:1). The resulting mixture was carefully stirred at 90° C. for 48 h. After cooling to r.t., the dark red solution was poured slowly onto ice-cooled water. The product was extracted with EtOAc (6×10 mL), and the organic layers were concentrated carefully under vacuum. The crude product was purified via a plug silica column in pet. ether/EtOAc (8:2), to give the desired product 14 as a crystalline beige solid (19.4 mg, 29.1%).

$^1$H NMR (d$_6$-acetone, 400 MHz) δ (ppm): 7.39 (s, 2H, H$_4$), 2.64 (s, 6H, H$_1$). For comparison, the NMR data for the precursor to the azide, 2,6-diacetyl-4-bromopyridine (13) is as follows: $^1$H NMR (d$_6$-acetone, 400 MHz) δ (ppm): 8.26 (s, 2H, H$_4$), 2.74 (s, 6H, H$_1$); $^{13}$C NMR (d$_6$-acetone, 400 MHz) δ (ppm): 198.0 (C$_2$), 154.6 (C$_3$), 135.5 (C$_5$), 128.0 (C$_4$), 25.5 (C$_1$).

By the appendage of an azide group to the pyridine head-unit, in theory any alkyne-functionalized unit may now be 'clicked' on via the CuAAC reaction, followed by macrocyclization to give a functionalized contrast agent. Potential 'clickable' groups include (bio)molecules with targeting potential, such the commercially available estrogen mimic ethynylestradiol, 15.[33]

Functionalization of selected probes with 15 may, for example, facilitate the passive targeting of breast cancer cells.[34] Other clickable functionalities include but are not limited to commercially available water soluble fluorescent probes such as boron-dipyrromethene (BODIPY, 16) derivatives which have been previously appended to Gd$^{III}$ DOTA[35] for dual modality imaging.

Two approaches can be employed for the synthesis of the functionalized macrocycle.

Method A—Click Prior to Templation:

A compound of Formula IV as defined herein (e.g. about 1 equivalent) is added to a solution of a compound of Formula V as defined herein (e.g. about 1 equivalent) in a suitable solvent (e.g. methanol) and the mixture heated to a suitable temperature, for example, about 30° C. to about 70° C. or about 50° C., a diamine of Formula VI as defined herein (e.g. about 1 equivalent) is added, then the resultant mixture heated to a temperature of about 75° C. to about 95° C. or about 85° C. and refluxed for a suitable time, for example about 4 hours to about 18 hours.

Method B—Click Post Templation:

A compound of Formula II as defined herein (e.g. about 1 equivalent) is added to a solution of a compound of Formula V as defined herein (e.g. about 1 equivalent) in a suitable solvent (e.g. methanol) and the mixture heated to a suitable temperature, for example, about 30-50° C., a diamine of Formula VI as defined herein (e.g. about 1 equivalent) is added, then the resultant mixture heated to a temperature of about 70-80° C. and refluxed for a suitable time, for example about 4 hours to about 18 hours. Following the formation of the azide-functionalized macrocycle, the CuAAC reaction is performed.

While the present application has been described with reference to what are presently considered to be the preferred examples, it is to be understood that the application is not limited to the disclosed examples. To the contrary, the present application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS
REFERRED TO IN THE DESCRIPTION

[1] P. K. Pal, A. Samii, D. Calne, *Neurotoxicology* 1999, 20, 227.

[2] T. Grobner, *Nephrol. Dial. Transplant.* 2006, 21, 1104-1108.

[3] a) R. M. Petoral Jr, F. Söderlind, A. Klasson, A. Suska, M. A. Fortin, N. Abrikossova, L. Selegård, P.-O. Käll, M. Engström, K. Uvdal, *J. Phys. Chem. C* 2009, 113, 6913-6920; b) L. Frullano, T. Meade, *J. Biol. Inorg. Chem.* 2007, 12, 939-949.

[4] a) S. M. Janib, A. S. Moses, J. A. MacKay, *Adv. Drug Deliv. Rev.* 2010, 62, 1052-1063; b) D. Pan, S. D. Caruthers, G. Hu, A. Senpan, M. J. Scott, P. J. Gaffney, S. A. Wickline, G. M. Lanza, *J. Am. Chem. Soc.* 2008, 130, 9186-9187.

[5] K. S. Samkoe, S. C. Davis, S. Srinivasan, J. A. O'Hara, T. Hasan, B. W. Pogue, A Study of MRI-Guided Diffuse Fluorescence Molecular Tomography for Monitoring PDT Effects in Pancreas Cancer. Photodynamic Therapy: Back to the Future, edited by D. H. Kessel, Proc. of SPIE Vol. 7380, 73803M.

[6] a) F. Bonadio, M.-C. Senna, J. Ensling, A. Sieber, A. Neels, H. Stoeckli-Evans, S. Decurtins, *Inorg. Chem.* 2005, 44, 969-978; b) D. Zhang, H. Wang, Y. Chen, Z.-H. Ni, L. Tian, J. Jiang, *Inorg. Chem.* 2009, 48, 5488-5496; c) G. Rombaut, S. Golhen, L. Ouahab, C. Mathonière, O. Kahn, *J. Chem. Soc. Dalton Trans.* 2000, 3609-3614; d) K. Qian, X.-C. Huang, C. Zhou, X.-Z. You, X.-Y. Wang, K. R. Dunbar, *J. Am. Chem. Soc.* 2013, 135, 13302-13305; e) A. K. Sra, M. Andruh, O. Kahn, S. Golhen, L. Ouahab, J. V. Yakhmi, *Angew. Chem., Int. Ed.* 1999, 38, 2606-2609; f) X. Y. Wang, A. V. Prosvirin, K. R. Dunbar, *Angew. Chem. Int. Ed.* 2010, 49, 5081-5084.

[7] a) M. Rohrer, H. Bauer, J. Mintorovitch, M. Requardt, H.-J. Weinmann, *Invest. Radiol.* 2005, 40, 715; b) P. Caravan, J. J. Ellison, T. J. McMurry, R. B. Lauffer, *Chem. Rev.* 1999, 99, 2293; c) P. Hermann, J. Kotek, V. Kubiček, I. Lukeš, *Dalton Trans.* 2008, 3027; d) S. Aime, P. Caravan, *J. Magn. Reson. Imaging* 2009, 30(6), 1257.

[8] D. Weishaupt, V. D. Köchli, B. Marincek. *How Does an MRI Work?* 2008, Springer, Berlin.

[9] P. Ascenzi, A. Bocedic, M. Marino, *Mol. Aspects Med.* 2006, 27(4), 299.

[10] Kin-Mang Lau, S. C. Mok, S.-M. Ho, *PNAS*, 1999, 96(10), 5722.

[11] E. Weiderpass, I. Persson, H. Melhus, S. Wedrén, A. Kindmark and, J. A. Baron, *Carcinogenesis* 2000, 21(4), 623.

[12] Y. Arao, K. J. Hamilton, E. H. Goulding, K. S. Janardhan, E. M. Eddy, K. S. Korach, *PNAS* 2012, 109, 51.

[13] A. Frank, L. M. Brown, D. J. Clegg, *Front. Neuroendocrin.* 2014, 35(4), 550.

[14] S. Bord, A. Horner, S. Beavan, J. Compston, *JCEM* 2001, 86(5), 2309.

[15] A. B. Ropero, M. Eghbali, T. Y. Minosyan, G. Tang, L. Toro, E. Stefani, *J. Mol. Cell. Cardiol.* 2006, 41(3), 496.

[16] S. Mollerup, K. Jørgensen, G. Berge, A. Haugen, *Lung Cancer* 2002, 37(2), 153.

[17] Y. G. Assaraf, C. P. Leamon, J. A. Reddy, *Drug Resist. Update* 2014, 17(4-6), 89.

[18] P. De, S. Gondi, B. Sumerline, *Biomacromol.* 2008, 9, 1064.

[19] L. D. Lavis, R. T. Raines, *ACS Chem. Biol.* 2008, 3(3), 142-155.

[20] See, for example: E. Heyer et al., *Angew. Chem. Int. Ed.* 2015, 54, 2995-2999.

[21] V. V. Rostovtsev, L. G. Green, V. V. Fokin, K. B. Sharpless, *Angew. Chem., Int. Ed.* 2002, 41, 2596 [$Cu^{II}SO_4$+ascorbic acid]; M. Meldal, C. W. Tornoe, *Chem. Rev.* 2008, 108, 2952 [$Cu^I$ salts]; J. E. Hein, V. V. Fokin, *Chem. Soc. Rev.* 2010, 39(4), 1302 [$Cu^I$ coordination complexes, $Cu^I$ tris(triazolyl)methyl amines]; V. O. Rodionov, S. I. Presolski, S. Gardinier, Y.-H. Lim, J. Am. Chem. Soc. 2007, 129(42), 12696 [$Cu^I$ tris(benzimidazolyl)methyl amines]; S. Diez-González, A. Correa, L. Cavallo, S. P. Nolan, *Chem. Eur. J.* 2006, 12(29), 7558 [$Cu^I$ N-heterocyclic carbenes]; and T. Nakamura, T. Terashima, K. Ogata, S. Fukuzawa, *Org. Lett.* 2011, 13(4), 620 [$Cu^I$-1,2,3-triazol-5-ylidenes].

[22] a) R. D. Cannon, B. Chiswell, L. M. Venanzi, *J. Chem. Soc. A* 1967, 1277-1281; b) M. Numata, K. Koumoto, M. Mizu, K. Sakurai, S. Shinkai, *Org. Biomol. Chem.* 2005, 3, 2255-2261; c) K. M. Bonger, R. J. B. H. N. van den Berg, L. H. Heitman, A. P. Ijzerman, J. Oosterom, C. M. Timmers, H. S. Overkleeft, G. A. van der Marel, *Bioord. Med. Chem.* 2007, 15, 4841-4856; d) R. Moreno-Corral, H. Höpfl, L. Machi-Lara, K. O. Lara, *Eur. J. Org. Chem.* 2011, 2148-2162; e) K. E. Pryor, G. W. Shipps Jr, D. A. Skyler, J. Rebek Jr, *Tetrahedron* 1998, 54, 4107-4124; f) J. Wang, B. Slater, A. Alberola, H. Stoeckli-Evans, F. S. Razavi, M. Pilkington, *Inorg. Chem.* 2007, 46, 4763-4765.

[23] Q. Wang, S. Vanneri, N. Zarrabi, H. Wang, C. Desplanches, J.-F. Letard, T. Seda, M. Pilkington, *Dalton Trans.* 2015, 44, 6711.

[24] M. G. B. Drew, A. H. B. Othman, S. G. McFall, P. D. A. Mcllroy, S. M. Nelson, *J. Chem. Soc., Dalton Trans.* 1977, 1173-1180.

[25] D. Zhang, H. Wang, L. Tian, J. Jiang, Z.-H. Ni, *CrystEngComm* 2009, 11, 2447-2451.

[26] J. Wang, B. Slater, A. Alberola, H. Stoeckli-Evans, F. S. Razavi, M. Pilkington, *Inorg. Chem.* 2007, 46, 4763-4765.

[27] A. Mirfazaelian, J. W. Fisher, *J. Toxicol. Environ. Health* 2007, 70, 1052-1063.

[28] a) H. C. Kolb, M. G. Finn, K. B. Sharpless, *Angew. Chem. Int. Ed.* 2001, 40, 2004-2021; b) J. E. Hein, V. V. Fokin, *Chem. Soc. Rev.* 2010, 39, 1302-1315.

[29] H. Takalo, J. Kankare, *Acta Chem. Scand. B* 1987, 42, 373-375.

[30] A. Sidibe, F. Hamon, E. Largy, D. Gomez, M.-P. Teulade-Fichou, C. Trentesaux, J.-F. Riou, *Biochimie* 2012, 94, 2559-2568.

[31] a) R.-A. Fallahpour, E. C. Constable, *J. Chem. Soc. Perkin Trans.* 1 1997, 2263-2264; b) Y. Oikawa, K. Sugano, O. Yonemitsu, *J. Org. Chem.* 1978, 43, 2087-2088.

32. C. S. Bonnet, F. Buron, F. Caillé, C. M. Shade, B. Drahoš, L. Pellegatti, J. Zhang, S. Villette, L. Helm, C. Pichon, *Chem. Eur. J.* 2012, 18, 1419-1431.
33. a) O. I. Bol'shakov, I. O. Lebedyeva, A. R. Katritzky, *Synthesis* 2012, 44, 2926-2932; b) H.-Y. Kim, J. Sohn, G. T. Wijewickrama, P. Edirisinghe, T. Gherezghiher, M. Hemachandra, P.-Y. Lu, R. E. Chandrasena, M. E. Molloy, D. A. Tonetti, G. R. J. Thatcher, *Bioord. Med. Chem.* 2010, 18, 809-821.
34. K. P. Madeira, R. D. Daltoé, G. M. Sirtoli, A. A. Carvalho, L. B. A. Rangel, I. V. Silva, *Mol. Biol. Rep.* 2014, 41, 5459-5466.
35. C. Bernhard, C. Goze, Y. Rousselin, F. Denat, *Chem. Commun.* 2010, 46, 8267-8269.

TABLE 1

Summary of the $Gd^{III}$-based contrast agents.

| Drug Name | Formula Active Ingredient | Clearance | Use |
|---|---|---|---|
| Magnevist gadopentetate | $(MEG)_2[Gd(DTPA)H_2O]$ | renal 1.60 h | CNS, whole body |
| Eovist or Primovist gadoxetate | $Na_2[Gd(EOB\text{-}DTPA)H_2O]$ | renal/hepatic 50:50 | liver |
| Ablavar or Vasovist gadofosveset | $Na_3[Gd(MS\text{-}325\text{-}L)H_2O]$ | renal/hepatic 91:9 18.5 h | blood pool |
| Multihance gadobenate | $(MEG)_2[Gd(BOPTA)H_2O]$ | renal/hepatic 96:4 1.2-2 h | CNS, liver |
| Omniscan gadodiamide | $[Gd(DTPA\text{-}BMA)H_2O]$ | renal 1.30 h | CNS, whole body |
| OptiMARK gadoversetamide | $[Gd(DTPA\text{-}BMEA)H_2O]$ | renal 1.73 h | CNS, whole body |
| Dotarem* gadoterate | $(MEG)[Gd(DOTA)H_2O]$ | renal | CNS, whole body |
| Prohance gadoteridol | $[Gd(HP\text{-}DO3A)H_2O]$ | renal 1.57 h | CNS, whole body |
| Gadavist gadobutrol | $[Gd(DO3A\text{-}butrol)H_2O]$ | renal | CNS, whole body |

*MEG = meglumine cation, $C_7H_{18}NO_5^+$.

TABLE 2

Isolated $Mn^{II}$ and $Gd^{III}$ complexes of L1-L7.

| No. | Formula | | C | H | N | $\nu(C=N)$ $(cm^{-1})$ |
|---|---|---|---|---|---|---|
| 1 | $[MnL1Cl_2]\cdot 2H_2O$ | Found | 45.01 | 5.88 | 17.21 | 1649 |
| | | Calcd | 45.13 | 5.81 | 17.54 | |
| 2 | $[MnL2Cl_2]\cdot 2H_2O$ | Found | 41.19 | 5.69 | 9.43 | 1645 |
| | | Calcd | 41.21 | 5.76 | 9.61 | |
| 3 | $[MnL3Cl_2]\cdot 2H_2O$ | Found | 55.72 | 4.65 | 8.39 | 1671 |
| | | Calcd | 55.55 | 4.26 | 8.45 | |
| 4 | $[MnL4Cl_2]\cdot 2H_2O$ | Found | 55.15 | 5.63 | 6.79 | 1650 |
| | | Calcd | 55.02 | 5.64 | 7.13 | |
| 5 | $[MnL6Cl_2]\cdot 2H_2O$ | Found | 51.88 | 4.98 | 7.31 | 1618 |
| | | Calcd | 52.01 | 5.06 | 7.28 | |
| 6 | $[Mn_2L7Cl_4(H_2O)_2]\cdot 3H_2O$ | Found | 40.27 | 5.49 | 9.52 | 1647 |
| | | Calcd | 40.47 | 5.66 | 9.44 | |
| 7 | $[GdL1Cl_3]\cdot 3H_2O$ | Found | 30.48 | 5.21 | 11.95 | 1631 |
| | | Calcd | 30.48 | 4.95 | 11.85 | |
| 8 | $[GdL2Cl_3H_2O]\cdot 6H_2O$ | Found | 27.89 | 5.23 | 6.35 | 1620 |
| | | Calcd | 27.84 | 5.14 | 6.49 | |
| 9 | $[GdL6Cl_3]\cdot 6H_2O$ | Found | 38.50 | 4.39 | 5.14 | 1628 |
| | | Calcd | 38.14 | 4.74 | 5.34 | |

TABLE 3

Summary of $r_1$ and $r_2$ $(s^{-1} \cdot mM^{-1})$ relaxivity data.

| | | MHz | 60 | | 20 | |
|---|---|---|---|---|---|---|
| Compound No. | Formula | | $r_1$ | $r_2$ | $r_1$ | $r_2$ |
| 1 | $[MnL1Cl_2]\cdot 2H_2O$ | | 2.76 | 10.7 | 3.78 | 6.07 |
| 2 | $[MnL2Cl_2]\cdot 2H_2O$ | | 2.78 | 12.7 | 3.58 | 6.67 |
| 4 | $[MnL4Cl_2]\cdot 2H_2O$ | | 4.00 | 23.0 | 5.34 | 14.8 |
| 5 | $[MnL6Cl_2]\cdot 2H_2O$ | | 2.97 | 31.1 | 7.22 | 42.9 |
| 6 | $[Mn_2L7Cl_4]\cdot 5H_2O$ | | 7.36 | 30.7 | 10.0 | 26.8 |
| 7 | $[GdL1Cl_3]\cdot 3H_2O$ | | 5.58 | 6.77 | 6.43 | 6.85 |
| 8 | $[GdL2Cl_3]\cdot 6H_2O$ | | 6.04 | 7.67 | — | — |
| 9 | $[GdL6Cl_3]\cdot 6H_2O$ | | 2.78 | 8.68 | 8.05 | 8.60 |

TABLE 4

Inhibitory concentrations ($IC_{50}$, mM).

| No. | Formula | 2 hr | 4 hr | 10 hr | 24 hr |
|---|---|---|---|---|---|
| 1 | $[MnL1Cl_2]\cdot 2H_2O$ | ND | ND | ND | 5.47 |
| 2 | $[MnL2Cl_2]\cdot 2H_2O$ | 3.88 | 2.56 | 14.66 | 0.68 |
| 5 | $[MnL6Cl_2]\cdot 2H_2O$ | 1.25 | 0.67 | 1.39 | 0.21 |
| 7 | $[GdL1Cl_3]\cdot 3H_2O$ | 8.15 | 3.37 | 8.53 | 0.92 |
| 8 | $[GdL2Cl_3H_2O]\cdot 6H_2O$ | 9.39 | 3.65 | 5.32 | 1.1 |
| 9 | $[GdL6Cl_3]\cdot 6H_2O$ | 2.9 | 2.19 | 2.195 | 1.27 |
| | Gadodiamide | ND | ND | >30 mM | 31.05 |

ND: not determined due to lack of dose response.

TABLE 5

Change in MRI signal intensity (arbitrary units of voxel intensity) in various tissues following injection of 1.

| | Minutes | | | | | | | Max. intensity change |
|---|---|---|---|---|---|---|---|---|
| | −10 | 2 | 10 | 15 | 20 | 30 | 45 | |
| Renal cortex | 579.1 | 635.2 | 683.4 | 660.3 | 717.0 | 775.4 | 804.1 | 39% |
| Renal medulla | 480.8 | 608.9 | 561.8 | 524.4 | 502.9 | 512.6 | 520.6 | 27% |
| Renal pelvis | 465.7 | 881.1 | 920.7 | 806.3 | 733.9 | 704.7 | 666.1 | 98% |
| Liver | 498.6 | 458.8 | 436.2 | 410.2 | 424.5 | 398.0 | 369.8 | −26% |
| Bladder | 414.3 | 454.3 | 1093.1 | 1147.9 | 1046.4 | 970.1 | 1030.1 | 177% |
| Skeletal muscle | 432.1 | 358.5 | 354.3 | 346.5 | 337.5 | 330.6 | 351.0 | −23% |

TABLE 6

Change in $T_1$-weighted MRI signal intensity (arbitrary units of voxel intensity) in various tissues following injection of 2.

| | Minutes | | | | | Max. intensity change |
|---|---|---|---|---|---|---|
| | −10 | 1 | 15 | 30 | 45 | |
| Renal cortex | 8005 | 9368 | 10144 | 10702 | 11485 | 43% |
| Renal medulla | 7725 | 9169 | 8472 | 7969 | 8615 | 19% |
| Liver | 7276 | 7568 | 7385 | 7812 | 7683 | 7% |
| Bladder | 5085 | 5155 | 16182 | 11996 | 13104 | 218% |
| Lean muscle | 5640 | 5841 | 5696 | 5569 | 5574 | 3% |
| Fat | 14509 | 15671 | 15845 | 15745 | 15860 | 9% |

TABLE 7

Change in $T_1$-weighted MRI signal intensity (arbitrary units of voxel intensity) in various tissues following injection of 6.

| | Minutes | | | | Max. intensity change |
|---|---|---|---|---|---|
| | −10 | 1 | 16 | 29 | |
| Renal cortex | 8324 | 7160 | 6355 | 7030 | −24% |
| Renal medulla | 7439 | 9222 | 7008 | 7345 | 24% |
| Liver | 7948 | 6234 | 5508 | 5838 | −31% |
| Bladder | 6374 | 4991 | 8171 | 10143 | 59% |
| Lean muscle | 6710 | 4720 | 4284 | 4095 | −39% |
| Fat | 16614 | 12834 | 13248 | 13001 | −23% |

TABLE 8

Change in $T_2$-weighted MRI signal intensity (arbitrary units of voxel intensity) in various tissues following injection of 2.

| | Minutes | | | | Max. intensity change |
|---|---|---|---|---|---|
| | −10 | 8 | 22 | 37 | |
| Renal cortex | 4759 | 3367 | 3307 | 3034 | −36% |
| Renal medulla | 6454 | 5342 | 5306 | 4215 | −35% |
| Liver | 965 | 788 | 577 | 400 | −59% |
| Bladder | 12921 | 7977 | 667 | 512 | −96% |
| Lean muscle | 2673 | 2386 | 2451 | 2377 | −11% |
| Fat | 14834 | 14550 | 12923 | 13440 | −13% |

TABLE 9

Change in $T_2$-weighted MRI signal intensity signal intensity (arbitrary units of voxel intensity) in various tissues following injection of 6.

| | Minutes | | | | Max. intensity change |
|---|---|---|---|---|---|
| | −10 | 1 | 16 | 29 | |
| Renal cortex | 7718 | 4270 | 4640 | 2963 | −62% |
| Renal medulla | 12041 | 7869 | 7063 | 2770 | −77% |

TABLE 9-continued

Change in $T_2$-weighted MRI signal intensity signal intensity (arbitrary units of voxel intensity) in various tissues following injection of 6.

| | Minutes | | | | Max. intensity change |
|---|---|---|---|---|---|
| | −10 | 1 | 16 | 29 | |
| Liver | 739 | 588 | 498 | 408 | −45% |
| Bladder | 16247 | 14484 | 13169 | 10727 | −34% |
| Lean muscle | 3053 | 2707 | 2399 | 2063 | −32% |
| Fat | 15094 | 9718 | 10027 | 8525 | −44% |

The invention claimed is:

1. A method of enhancing contrast in a magnetic resonance image of a subject, the method comprising:
   (a) administering to the subject, a compound of Formula I(b) or a hydrate thereof:

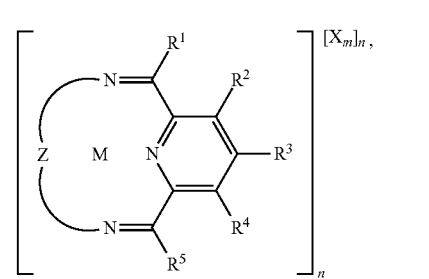

wherein
$R^1$ and $R^5$ are each independently $C_{1-6}$alkyl or aryl;
$R^2$ and $R^4$ are each independently H, —OH, halo, $C_{1-6}$alkyl, aryl or $C_{1-3}$alkyleneC(O)OR$^6$, wherein $R^6$ is H or $C_{1-6}$alkyl;
n is 1 or 2;
when n is 1, $R^3$ is H, —OH, halo, $C_{1-6}$alkyl, aryl or $C_{1-3}$alkyleneC(O)OR$^6$, wherein $R^6$ is H or $C_{1-6}$alkyl;
when n is 2, $R^3$ represents a single bond;
X is a pharmaceutically acceptable counteranion;
Z is —(CR$^7$R$^8$ ═══ CR$^9$R$^{10}$-A)$_p$-(CR$^{11}$R$^{12}$ ═══ CR$^{13}$R$^{14}$)—;
wherein
A is O;
p is 2, 3 or 4;
═══ represents a single or double bond;
when ═══ is a double bond, one of R$^7$/R$^8$ and R$^9$/R$^{10}$ or R$^{11}$/R$^{12}$ and R$^{13}$/R$^{14}$, as applicable, is not present; and
$R^7$ to $R^{14}$ are each independently H, $C_{1-6}$alkyl or aryl; or
one of R$^7$/R$^8$ and R$^9$/R$^{10}$ and/or R$^{11}$/R$^{12}$ and R$^{13}$/R$^{14}$, together with the carbon atoms to which they are attached, form a 5-6 membered carbocycle;
the N and A atoms in the compound of Formula I(b) form an N$_3$A$_p$ donor set for coordinating with M;
M is selected from $Fe^{3+}$, $Fe^{2+}$, $Co^{2+}$, $Zn^{2+}$, $Mn^{3+}$, $Mn^{2+}$ and $Gd^{3+}$ and is coordinated in an equatorial fashion by at least three atoms of the N$_3$A$_p$ donor set;
when M is $Fe^{2+}$, $Co^{2+}$, $Zn^{2+}$ or $Mn^{2+}$, m is 2; and
when M is $Fe^{3+}$, $Mn^{3+}$ or $Gd^{3+}$, m is 3; and
(b) obtaining a magnetic resonance image of the subject.

2. The method of claim 1, wherein the compound of Formula I(b) is

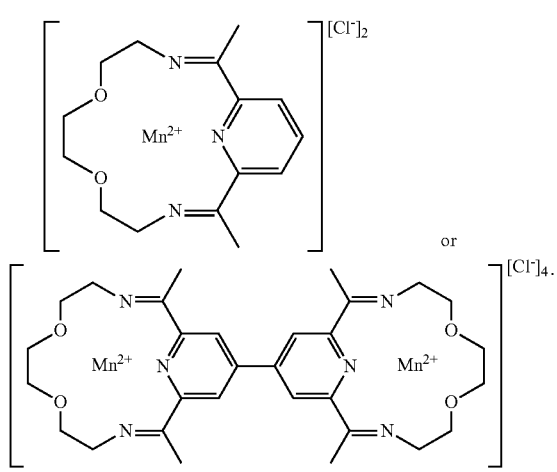

or

3. The method of claim 1, wherein $R^1$ and $R^5$ are each independently $C_{1-6}$alkyl or phenyl.

4. The method of claim 3 wherein $R^1$ and $R^5$ are each independently $C_{1-4}$alkyl.

5. The method of claim 1, wherein $R^2$ and $R^4$ are each independently H, —OH, Cl, Br, I, $C_{1-4}$alkyl, phenyl or $C_{1-3}$alkyleneC(O)OR$^6$, wherein $R^6$ is H or $C_{1-4}$alkyl.

6. The method of claim 5, wherein $R^2$ and $R^4$ are each H.

7. The method of claim 5, wherein $R^2$ and/or $R^4$ is $C_{1-3}$alkyleneC(O)OR$^6$, wherein $R^6$ is H or $C_{1-6}$alkyl.

8. The method of claim 1, wherein n is 1 and $R^3$ is H, —OH, halo, $C_{1-6}$alkyl, aryl or $C_{1-3}$alkyleneC(O)OR$^6$, wherein $R^6$ is H or $C_{1-6}$alkyl.

9. The method of claim 8, wherein $R^3$ is H.

10. The method of claim 8, wherein $R^3$ is $C_{1-3}$alkyleneC(O)OR$^6$, wherein $R^6$ is H or $C_{1-6}$alkyl.

11. The method of claim 5, wherein n is 2 and $R^3$ represents a single bond.

12. The method of claim 5, wherein X is selected from $Cl^-$, $HCO_3^-$, $CO_3^{2-}$, $H_2PO_4^-$, $HPO_4^{2-}$ and $PO_4^{3-}$.

13. The method of claim 1, wherein p is 2 or 3.

14. The method of claim 1, wherein $R^7$ to $R^{14}$ are each independently H, $C_{1-4}$alkyl or phenyl.

15. The method of claim 5, wherein one of $R^7/R^8$ and $R^9/R^{10}$ and/or $R^{11}/R^{12}$ and $R^{13}/R^{14}$, together with the carbon atoms to which they are attached, form a phenyl.

16. The method of claim 1, wherein Z is selected from —(CH$_2$CH$_2$O)$_2$—(CH$_2$CH$_2$)—,

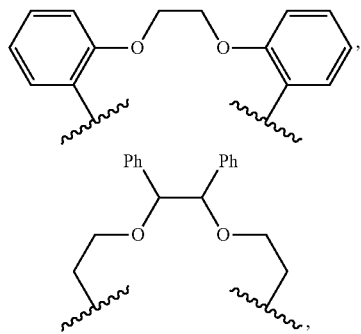

—(CH$_2$CH$_2$O)$_3$—(CH$_2$CH$_2$)— and

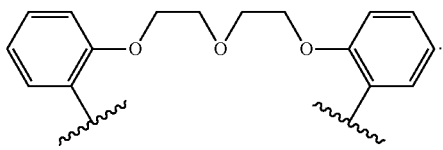 [SMILES: *c1ccccc1OCCOCCOc1ccccc1*]

17. The method of claim 1, wherein Z is selected from —(CH$_2$CH$_2$O)$_2$—(CH$_2$CH$_2$)—,

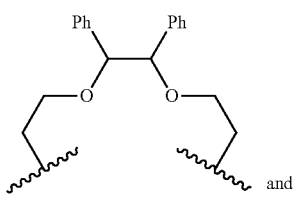

and

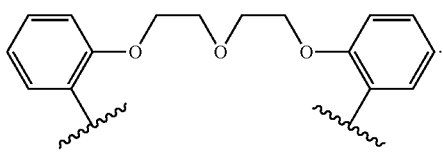

18. The method of claim 1, wherein M is Mn$^{2+}$ and m is 2 or M is Gd$^{3+}$ and m is 3.

19. The method of claim 1, wherein the compound of Formula I(b) is selected from:

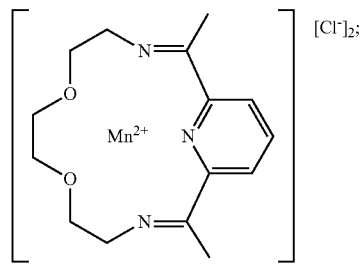

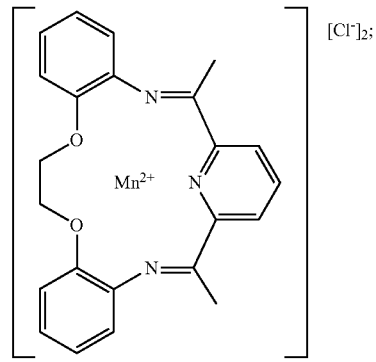

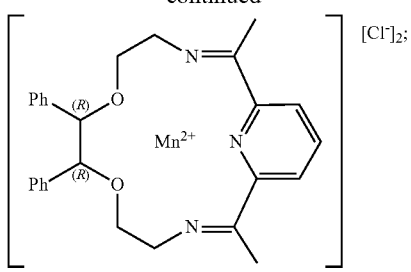
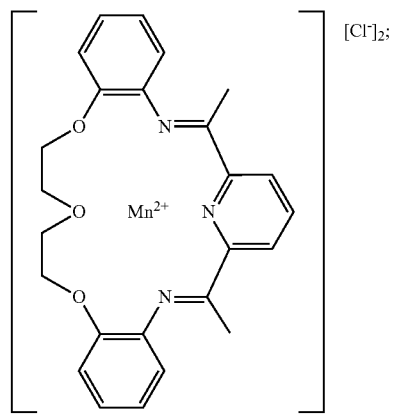
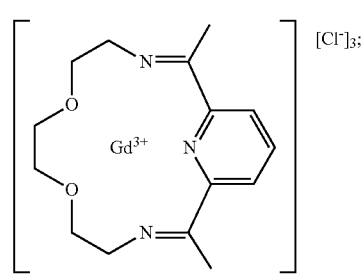
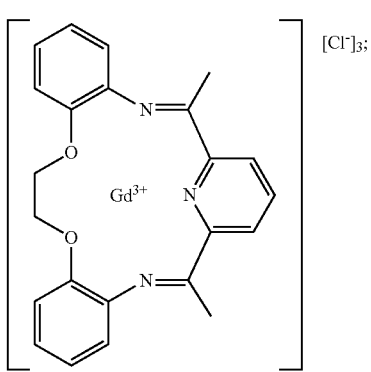
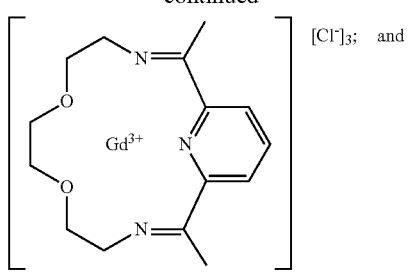
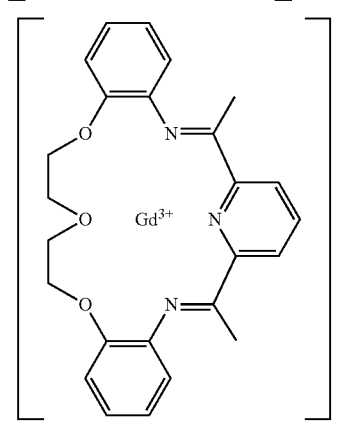
20. The method of claim 1, wherein the compound of Formula (Ib) is selected from:
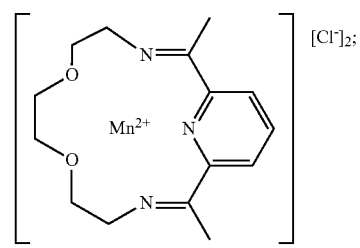
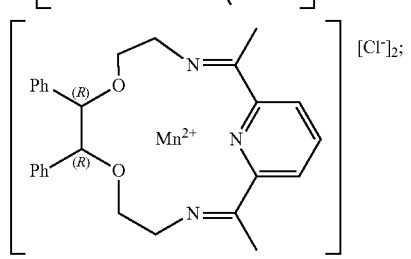
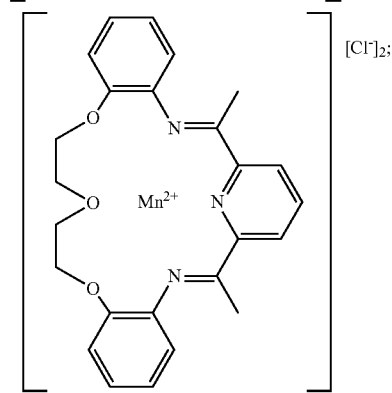

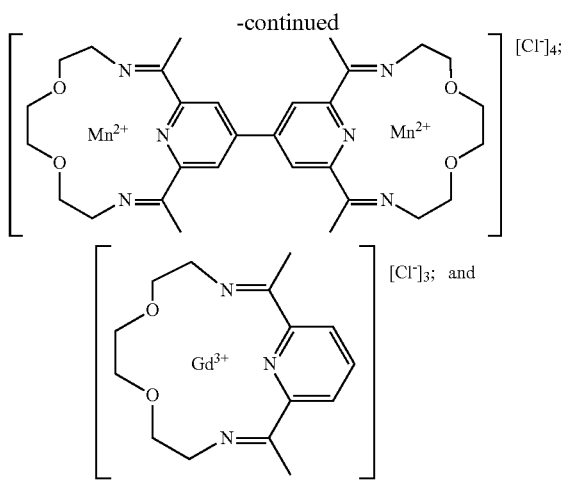
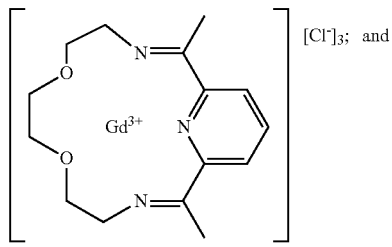
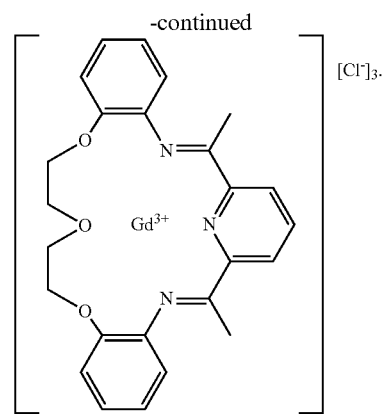
* * * * *